(12) United States Patent
Chen et al.

(10) Patent No.: US 10,754,928 B2
(45) Date of Patent: *Aug. 25, 2020

(54) METHODOLOGIES LINKING PATTERNS FROM MULTI-MODALITY DATASETS

(71) Applicant: Banner Health, Phoenix, AZ (US)

(72) Inventors: Kewei Chen, Chandler, AZ (US); Eric M. Reiman, Scottsdale, AZ (US)

(73) Assignee: BANNER HEALTH, Phoenix, AZ (US)

( * ) Notice: Subject to any disclaimer, the term of this patent is extended or adjusted under 35 U.S.C. 154(b) by 1080 days.

This patent is subject to a terminal disclaimer.

(21) Appl. No.: 15/207,478

(22) Filed: Jul. 11, 2016

(65) Prior Publication Data

US 2017/0091418 A1 Mar. 30, 2017
US 2017/0300658 A9 Oct. 19, 2017

Related U.S. Application Data

(63) Continuation of application No. 11/242,820, filed on Oct. 3, 2005, now Pat. No. 9,471,978.

(Continued)

(51) Int. Cl.
*A61B 5/00* (2006.01)
*G06F 19/00* (2018.01)
(Continued)

(52) U.S. Cl.
CPC .......... *G06F 19/3456* (2013.01); *A61B 5/165* (2013.01); *G06T 7/0012* (2013.01);
(Continued)

(58) Field of Classification Search
CPC .................... G06T 7/0012; G06T 7/97; G06T 2207/10088; G06T 2207/10104;
(Continued)

(56) References Cited

U.S. PATENT DOCUMENTS

| 5,617,861 A | 4/1997 | Ross et al. |
| 6,377,833 B1 | 4/2002 | Albert |

(Continued)

FOREIGN PATENT DOCUMENTS

| WO | WO 2006/009887 | 1/2006 |
| WO | WO 2006/041816 | 4/2006 |
| WO | WO 2007/134123 | 11/2007 |

OTHER PUBLICATIONS

Mosconi et al., "Age and ApoE genotype interaction in Alzheimer's disease: an FDG-PET study" Psychiatry Research: Neuroimaging, vol. 130, Issue 2, Feb. 15, 2004, pp. 141-151 (Year: 2004).*

(Continued)

*Primary Examiner* — Boniface N Nganga
(74) *Attorney, Agent, or Firm* — Lewis Roca Rothgerber Christie LLP

(57) ABSTRACT

A method is disclosed to acquire imaging and non-imaging datasets from like objects. A linkage is found using a partial least squares (PLS) technique between imaging and non-imaging datasets. The linkage is then reduced to an expression of a single numerical assessment. The single numerical assessment is then used as an objective, quantified assessment of the differences and similarities between the objects. The data each dataset can be aspects of performance, physical characteristics, or measurements of appearance.

20 Claims, 14 Drawing Sheets

Related U.S. Application Data

(60) Provisional application No. 60/615,767, filed on Oct. 4, 2004.

(51) Int. Cl.
*G06T 7/00* (2017.01)
*G16H 15/00* (2018.01)
*A61B 5/16* (2006.01)

(52) U.S. Cl.
CPC .............. *G06T 7/97* (2017.01); *G16H 15/00* (2018.01); *A61B 5/00* (2013.01); *G06T 2207/10088* (2013.01); *G06T 2207/10104* (2013.01); *G06T 2207/20104* (2013.01); *G06T 2207/30016* (2013.01); *G06T 2207/30096* (2013.01)

(58) Field of Classification Search
CPC . G06T 2207/20104; G06T 2207/30016; G06T 2207/30096; A51B 5/00; A51B 5/165; G16H 15/00
See application file for complete search history.

(56) References Cited

U.S. PATENT DOCUMENTS

| | | | |
|---|---|---|---|
| 6,448,221 | B1 | 9/2002 | Sheppard et al. |
| 6,560,354 | B1 | 5/2003 | Maurer, Jr. et al. |
| 6,917,845 | B2 | 7/2005 | Hsiung et al. |
| 7,239,908 | B1 | 7/2007 | Alexander et al. |
| 7,374,536 | B1 | 5/2008 | Taylor |
| 9,471,978 | B2 * | 10/2016 | Chen ..................... G06T 7/0012 |
| 2002/0113787 | A1 | 8/2002 | Ray et al. |
| 2003/0092980 | A1 | 5/2003 | Nitz |
| 2003/0225717 | A1 | 12/2003 | Keefer et al. |
| 2004/0066956 | A1 | 4/2004 | Ashton |
| 2004/0126892 | A1 | 7/2004 | Bogomolov et al. |
| 2005/0014997 | A1 | 1/2005 | Ruchti et al. |
| 2005/0078869 | A1 | 4/2005 | Kim |
| 2005/0080330 | A1 | 4/2005 | Masuzawa et al. |
| 2005/0084145 | A1 | 4/2005 | Pelletier et al. |
| 2005/0207631 | A1 | 9/2005 | Martens et al. |
| 2005/0209785 | A1 | 9/2005 | Wells et al. |
| 2005/0283054 | A1 | 12/2005 | Reiman |
| 2015/0080703 | A1 | 3/2015 | Reiman |

OTHER PUBLICATIONS

Abdi, Herve, "Partial Least Squares (PLS) Regression," Encyclopedia for research methods for the social sciences (Lewis-Beck Met al., eds) (2003), Thousand Oaks (CA): Sage.
Alexander et al., "Longitudinal PET Evaluation of Cerebral Metabolic Decline in Dementia: A Potential Outcome Measure in Alzheimer's Disease Treatment Studies", Am J. Psychiatry 2002; 159: 738-745.
Alexander G.E. et al., "Abnormalities in gray matter density in young adults at genetic risk for late-onset Alzheimer's disease", Presented at the 8th Internat. Conf. on AD and Related Dis, Stockholm, Jun. 2002 [abstract].
Alexander, G.E. et al., "APOE e4 dose effect on gray matter atrophy in cognitively normal adults", Society for Neuroscience, 2003.
Alexander, G.E. et al., "Application of the scaled subprofile model to functional imaging in neuropsychiatric disorders: A principal component approach to modeling brain function in disease," Human Brain Mapping 2:79-94 (1994).
Alexander, G.E. et al., "Evaluation of gray matter atrophy in cognitively normal apoe E e-4 homozygotes and heterozygotes with voxel-based MRI morphometry," 1st Annual meeting of Society for neuroscience, Nov. 10-15, 2001, San Diego.
Alexander, G.E. et al., "Individual differences in attentional performance predict verbal learning in healthy elderly", Arizona Alzheimer's Research Consortium, 2005.
Alexander, G.E. et al., "Interactive effects of APOE e4 and physical fitness on gray matter in cognitively normal adults", Society for Neuroscience, 2004.
Alexander, G.E. et al., "Longitudinal declines of gray matter in cognitively normal apolipoprotein E 4 homozygotes and heterozygotes evaluated by voxel based MRI Morphometry", Presented at the 8th Internal Conf. on AD and Related Dis, Stockholm, 2002 [abstract].
Alexander, G.E. et al., "Longitudinal PET Evaluation of Cerebral Metabolic Decline in Dementia: A Potential Outcome Measure in Alzheimer's Disease Treatment Studies," Am. J. Psychiatry 159:738-745, May 2002.
Alexander, G.E. et al., "Neuroimaging", The Dementias: Diagnosis, Treatment, and Research, 3rd Edition, 2003, pp. 103-136.
Alexander, G.E. et al., "Regional network analysis of gray matter atrophy in healthy aging", Abstract presented at the annual meeting of the International Neuropsychological Society, Baltimore, MD, 2004.
Alexander, G.E. et al., "Regional network pattern of MRI gray matter volume in Alzheimer's dementia", Alzheimer's & Dementia, The Journal of the Alzheimer's Association, vol. 2, Issue 3, 2006, S665.
Alexander, GE et al., "Regional network of magnetic resonance imaging gray matter volume in healthy aging", NeuroReport, Jul. 17, 2006, pp. 951-956.
American Psychiatric Association, "Diagnostic and statistical manual of mental disorders", 4th ed. Washington, DC: American Psychiatric Association, 1994.
Anderson, N.D et al., "The effects of divided attention on encoding- and retrieval-related brain activity: A PET study of younger and older adults," J. Cogn Neurosci, 12:775-792, Massachusetts Institute of Technology (2000).
Archibald, R. et al., "Improving tissue segmentation of human brain MRI through preprocessing by the Gegenbauer reconstruction method", NeuroImage 20, 2003, pp. 489-502.
Arfanakis, K. et al., "Combining independent component analysis and correlation analysis to probe interregional connectivity in fMRI task activation datasets," Magn Reson. Imaging 18:921-930 (2000).
Ashburner, J. et al., "Multimodal image coregistration and partitioning—a unified framework," Neuroimage. 6:209-217 (1997).
Ashburner, J. et al., "Voxel-based morphometry—the methods", Neuroimage 2000;11 :805-821.
Barga, Magnus et al., "A unified approach to PCA, PLS, MLR and CCA," Report LiTH-ISY-R-.1992, ISY, SE-581 83 (1997).
Baxter, L.C. et al., "Apolipoprotein E e4 affects new learning in cognitively normal individuals at risk for Alzheimer's disease", Neurobiol. Aging 24, 2003, pp. 947-952.
Beckmann, C.F. et al., "Probabilistic independent component analysis for functional magnetic resonance imaging," IEEE Trans. Med. Imaging 23:137-152, Feb. 2004.
Bierer, L.M. et al., "Neocortical neurofibrillary tangles correlate with dementia severity in Alzheimer's disease", Arch. Neurol. 1995;52:81-88.
Bobinski, Maciek et al., "MRI of entorhinal cortex in mild Alzheimer's disease", The Lancet, Jan. 2, 1999, vol. 353, pp. 38-40.
Bokde, A. et al, "Discrimination between Alzheimer's disease patients and healthy subjects: Resting FDG-PET data", International Conference on Alz. Dis. Related Disord., Madrid, Spain, 2006.
Cagnin, A. et al., "In-vivo measurement of activated microglia in dementia", Lancet. 2001; 358:461-467.
Calhoun, V.D. et al., "Latency (in)sensitive ICA, Group independent component analysis of fMRI data in the temporal frequency domain," Neuroimage. 20:1661-1669 (2003).
Calhoun, V.D. et al., "Spatial and temporal independent component analysis of functional MRI data containing a pair of task-related waveforms," Hum. Brain Mapp. 13:43-53 (2000).
Caselli, R.J. et al., "A distinctive interaction between chronic anxiety and problem solving in asymptomatic APOE e4 homozygotes", The Journal of Neuropsychiatry and Clinical Neurosciences 16, 2004, pp. 320-329.
Caselli, R.J. et al., "A preliminary fluorodeoxyglucose positron emission tomography study in healthy adults reporting dream-enactment behavior", Sleep 29, 2006, pp. 927-933.

(56) References Cited

OTHER PUBLICATIONS

Caselli, R.J. et al., "Alzheimer's disease: A century later", J Clin Psychiatry 67, 2006, pp. 1784-1800.
Caselli, R.J. et al., "Brain imaging and cognitive studies of asymptomatic APOE e4 carriers", International Neuropsychological Society Abst., 2003.
Caselli, R.J. et al., "Changes in personality during mid-life may correlate with risk for Alzheimer's disease", NeuroBiology of Aging 25, No. S2, 2004, p. 112.
Caselli, R.J. et al., "Cognitive domain decline in healthy apolipoprotein E e4 homozygotes before the diagnosis of mild cognitive impairment", Arch Neurol 64, 2007, pp. 1306-1311.
Caselli, R.J. et al., "Longitudinal changes in cognition and behavior in asymptomatic carriers of the APOE e4 allele", Neurology 62, 2004, pp. 1990-1995.
Caselli, R.J. et al., "Longitudinal Neuropsychological and behavioral study of presymptomatic ApoE e4 carriers and noncarriers", Annual meeting of the American Acad. of Neurology, 2003.
Caselli, R.J. et al., "Presymptomatic longitudinal decline in frontally mediated cognitive skills and memory in cognitively normal late middle aged APOE e4 carriers", Alzheimer's and Dementia, Feb. 2006, S292.
Caselli, R.J. et al., "The degenerative dementias", Textbook of Clinical Neurology, 2nd Edition, 2003, pp. 681-711.
Caselli, R.J. et al., "Therapeutic Interventions: Drug treatments and other therapies", Radin L, Radin G, editors. What if it's not Alzheimer's? 2nd edition. Amherst: Prometheus Books, 2007, pp. 73-89.
Chau, W. et al., "Multi-modality imaging data analysis with partial least squares, Brain and Cognition," 54:140-142, (2004).
Chen, H. et al., "A method based on independent component analysis for processing fMRI data," Sheng Wu Yi. Xue.Gong.Cheng Xue.Za Zhi. 19:64-66, Jan. 19, 2002.
Chen, K. et al., "A monte-carlo simulation package for the calculation of statistical power, familywise type I error of various global indices associated with neuroimaging studies", Society of Nuclear Medicine 51st Annual Meeting, 2004, 9th International Conference of Alzheimer's Dis Related Disord. 2004.
Chen, K. et al., "A monte-carlo simulation package, multiple comparison corrections and power estimation incorporating secondary supportive evidence", Proceedings of Complex Medical Engineering, IEEE, 2007, pp. 907-913.
Chen, K. et al., "Accounting for multiple comparisons using concurrences of the presence of activation and absence of deactivation in neuroimaging studies", Human Brian Mapping, Annual Meeting, 2003.
Chen, K. et al., "An automated algorithm for the computation of brain volume change from sequential MRIs using an iterative principal component analysis and its evaluation for the assessment of whole-brain atrophy rates in patients with probable Alzheimer's disease", NeuroImage 22, 2004, pp. 134-143.
Chen, K. et al., "An automated, normative-based fluorodeoxyglucose positron emission tomography image-analysis procedure to aid Alzheimer's disease diagnosis using statistical parametric mapping and interactive image display", Acad. Molecular Imaging Annual Conference, 2005.
Chen, K. et al., "Automated method using interactive principle component analysis for detecting brain atrophy rates from sequential MRI in persons with Alzheimer's disease", Soc. Neurosci. Abstr., 2001 [abstract].
Chen, K. et al., "Characterization of the image-derived carotid artery input function using independent component analysis for the quantitation of [18F] fluorodeoxyglucose positron emission tomography images", Phys. Med. Biol. 52, 2007, pp. 7055-7071.
Chen, K. et al., "Correlations between apolipoprotein E e4 gene dose and whole brain atrophy rates", Am J. Psychiatry, 2007, pp. 916-921.
Chen, K. et al., "Detection of gray matter atrophy from sequential MRI in AD patients", World Congress of Medical Physics and Biomedical engineering, 2003.
Chen, K. et al., "Estimation of whole-brain atrophy accounting for increased variability due to MRI scanner changes in our longitudinal neuroimaging Alzheimer's risk study", Soc. for Neurosci., 2006.
Chen, K. et al., "Evaluation of an iterative principal component analysis for detecting whole brain volume change in small animal magnetic resonance imaging", Presented at the 8th Internal. Conf. on AD and Related Dis, Stockholm, 2002 [abstract].
Chen, K. et al., "Gray tissue segmentation and voxel based morphometry in detecting gray matter atrophy from successive MRI: a preliminary study", Neuroimage 14, 2001, pp. 1238-1243.
Chen, K. et al., "Inter-frame co-registration of dynamically acquired fluoro-deoxyglucose positron emission tomography human brain data", Proceedings of Complex Medical Engineering, IEEE, 2007, pp. 901-906.
Chen, K. et al., "Linking Functional and Structural Brain Images with Multivariate Network Analyses: Description and Preliminary Application Using the Partial Least Square Method," World Congress on Medical Physics and Biomedical Engineering, Sydney, (2003).
Chen, K. et al., "Monte-carlo based neuroimaging set-level multiple-comparison correction", J Int. Federation of Automated Control Cont., 2003.
Chen, K. et al., "Noninvasive quantification of the cerebral metabolic rate for glucose using positron emission tomography, 18F-fluoro-2-deoxyglucose, the Patlak method, and an image-derived input function," J.Cereb. Blood Flow Metab 18:716-723, (1998).
Chen, K. et al., "Six-month cerebral metabolic declines in Alzheimer's disease, amnestic mild cognitive impairment and elderly normal control groups: Preliminary findings from the Alzheimer's disease neuroimaging initiative", Internal. Cont. AD Prevention, Washington, DC, 2007.
Chen, K. et al., "The noninvasive quantification of FDG PET using the input function derived over an automatically defined carotid artery region", Society for Neuroscience, 2004.
Chen, K. et al., "The pattern and severity of FDG PET abnormalities in Alzheimer's disease and amnestic mild cognitive impairment: Preliminary findings from the Alzheimer's disease neuroimaging initiative", Internal. Cont. AD Prevention, Washington, DC, 2007.
Chen, K. et al., "Using partial-least squares to demonstrate a correlation between combined PET/MRI scores and apolipoprotein E e4 gene dose", International Conference on Alz. Dis. Related Disord., Madrid, Spain, 2006. Alzheimer's and Dementia, May 2006, S672-S673.
Chen, K. et al., "Whole brain atrophy rates in cognitively normal persons at genetic risk for Alzheimer's disease", Presented at the 8th Internat. Conf. on AD and Related Dis, Stockholm, Jun. 2002 [abstract].
China Application No. 200580041489.6; Office Action dated Apr. 8, 2011.
China Application No. 200580041489.6; Office Action dated Mar. 1, 2010.
Coffey, CE et al., "Quantitative cerebral anatomy of the aging human brain: a cross-sectional study using magnetic resonance imaging", Neurology 1992; 42:527-536.
Cohen, D. et al., "Depression in family members caring for a relative with Alzheimer's disease", J Am Geriatr Soc Dec. 1988;36:885-889.
Convit, A. et al, "Specific hippocampal volume reduction in individuals at risk for Alzheimer's disease", Neurobiol Aging 1997;18:131-138.
Convit, A. et al., "Hippocampal volume losses in minimally impaired elderly", Lancet 1995; 345:266.
Coon, K.D. et al., "A High-density whole-genome association study reveals that APOE is the major susceptibility gene for sporadic late-onset Alzheimer's disease", J Cline Psychiatry 68, 2007, pp. 613-618.
Coon, K.D. et al., "A novel resequencing technique allows quantitation of heteroplasmy in MTDNA sequence variants 42 found in AD patients", Alzheimer's and Dementia, Feb. 2006, S199.
Coon, K.D. et al., "Peripheral mitochondrial DNA defects and enzyme functions as a mechanism for Alzheimer's disease", Neurobiol. Aging 25, S497, 2004.

(56) References Cited

OTHER PUBLICATIONS

Coon, K.D. et al., "Preliminary demonstration of an allelic association of the IREB2 gene with Alzheimer's disease", Journal of Alzheimer's Disease, Sep. 2006, pp. 225-233.
Coon, K.O. et al., "Quantitation of heteroplasmy of mtDNA sequence variants identified in a population of AD patients and controls by array-based resequencing", Mitochondrion, Jun. 2006, pp. 194-210.
Corder, E.H. et al. "Gene dose of apolipoprotein E type 4 allele and the risk of Alzheimer's disease in late onset families", Science 1993;261:921-924.
Corder, E.H. et al., "No difference in cerebral glucose metabolism in patients with Alzheimer disease and differing apolipoprotein E genotypes", Arch Neurol 1997;54:273-277.
Corder, E.H. et al., "Protective effect of apolipoprotein E type 2 allele for late onset Alzheimer disease", Nature Genetics 1994;7:180-184.
Csernansky, J.G. et al., "Early DAT is distinguished from aging by high-dimensional mapping of the hippocampus. Dementia of the Alzheimer type", Neurology Dec. 12, 2000;55(11):1636-1643.
Davis, D.A. et al., "Voxel-based network analysis of regional glucose metabolism in Alzheimer's disease", Society for Neuroscience, 2006.
de Leon, M.J. et al., "Computed tomography and positron emission transaxial evaluations of normal aging and Alzheimer's disease", J Cereb Blood Flow Metab 1983;3:391-394.
de Leon, M.J. et al., "Early marker for Alzheimer's disease: the atrophic hippocampus", Lancet 1989; 672-673.
de Leon, M.J. et al., "The radiologic prediction of Alzheimer's disease: the atrophic hippocampal formation", Am J Neuroradiol 1993;14:897-906.
DeCarli, C. et al., "Lack of age-related differences in temporal lobe volume of very healthy adults," AJNR Am. J. Neuroradiol. 15:689-696, (1994).
Demaerschalk, B.M. et al. "Dementia treatment: let the evidence lead us, Evidence-Based Neurological Management", Candelise L, Editor, Blackwell Publishing, 2007, pp. 184-198.
Deweer, B. et al., "Memory disorders in probable Alzheimer's disease; the role of hippocampal atrophy as shown in MRI", J.Neurol Neurosurg Psychiatry, 1995:58:590-597.
Div Neuropharrnacological Drug Products, US Food and Drug Administration. Background Document for Joint Advisory Committee Meeting of Nov. 18, 2002: Issues Related to the Role of Brain Imaging as an Outcome Measure in Phase Trials of Putative Drugs for Alzheimer's Disease. 2002 [Memo].
U.S. Appl. No. 11/155,711; Final Office Action dated Jan. 15, 2014.
U.S. Appl. No. 11/155,711; Office Action dated Aug. 5, 2013.
U.S. Appl. No. 11/155,711; Office Action dated Jun. 19, 2014.
U.S. Appl. No. 14/510,049; Office Action dated Oct. 27, 2015.
Du, A.T. et al., "Atrophy rates of entorhinal cortex in AD and normal aging", Neurology 2003; 60:481-486.
Du, A.T. et al., "Higher atrophy rate of entorhinal cortex than hippocampus in Alzheimer's disease", Neurology 2003 (in press).
Du, A.T. et al., "Magnetic resonance imaging of the entorhinal cortex and hippocampus in mild cognitive impairment and Alzheimer's disease", J Neurol Neurosurg Psychiatry 2001; 71:441-447.
Duann, J.R. et al., "Single-trial variability in event-related BOLD signals," Neuroimage. 15:823-835, (2002).
Duara, R. et al., "Positron emission tomography in Alzheimer's disease", Neurology 1986; 36:879-887.
Dunckley, T. et al., "Gene expression correlates of neurofibrillary tangles in Alzheimer's disease", Neurobiology of Aging 27,2006, pp. 1359-1371.
Dunckley, T. et al., "Mechanism of neurofibrillary tangle-induced neuronal degeneration leading to AD", NeuroBiology of Aging 25, S2, 2004, p. 427.
Esbensen, K. et al., "Fermentation monitoring using multisensor systems: feasibility study of the electronic tongue," Anal. Bioanal. Chem. 378:391-395 (2003).
Esposito, F. et al., "Real-time independent component analysis of fMRI time-series," Neuroimage. 20:2209-2224 (2003).

Etnier, J.L. et al., "ApoE-4 genotype and aerobic fitness as predictors of cognitive performance by older women", Arizona Alzheimer's Research Consortium, 2004.
Etnier, J.L. et al., "Cognitive performance in older women relative to ApoE-e4 genotype and aerobic fitness", Medicine & Science in Sports & Exercise 39, 2007, pp. 199-207.
Etnier, J.L. et al., "The differential benefits of aerobic fitness for cognitive performance as a function of ApoE genotype", Medicine & Science in Sports & Exercise 37, 2005, S462-S463.
European Application No. 05 77 2647, Search Report dated Apr. 14, 2008, 5 pages.
Evans, D.A. et al., "Prevalence of Alzheimer's disease in a community population of older persons: higher than previously reported", JAMA 1989; 262: 2551-2556.
Farrer, L.A. et al., "Effects of age, sex, and ethnicity on the association between apolipoprotein E genotype and Alzheimer disease. A meta-analysis", APOE and Alzheimer Disease Meta Analysis Consortium. JAMA 1997;278(16):1349-1356.
Fleming, T.R. et al., "Surrogate end points in clinical trials: are we being misled?", Ann Intern Med 1996; 125:605-613.
Foster, N.L. et al., "Alzheimer's disease: Focal cortical changes shown by positron emission tomography", Neurology 1983; 33: 961-965.
Fox, N.C. et al., "Atrophy of the hippocampal formation in early familial Alzheimer's disease. A longitudinal MRI study of at-risk members of a family with an amyloid precursor protein 717Val-Glymutation", Ann NY Acad Sci 1996; 777: 226-232.
Fox, N.C. et al., "Brain atrophy progression measured from registered serial MRI", J Magn Reson Imaging 1997;7:1069-1075.
Fox, N.C. et al., "Imaging of onset and progression of Alzheimer's disease with voxel-compression mapping of serial magnetic resonance images", Lancet 2001; 358: 201-205.
Fox, N.C. et al., "Presymptomatic hippocampal atrophy in Alzheimer's disease: a longitudinal MRI study", Brain 1996; 119: 2001-2007.
Fox, N.C. et al., "Using serial registered brain magnetic resonance imaging to measure disease progression in Alzheimer disease: power calculations and estimates of sample size to detect treatment effects", Arch Neurol 2000: 57: 333-444.
Fox, N.C. et al., "Visualization and quantification of rates of atrophy in Alzheimer's disease", Lancet 1996; 348: 94-97.
Freebourough, P.A. et al., "The boundary shift integral: an accurate and robust measure of cerebral volume changes from registered repeat MRI", IEEE Trans Med Imaging 1997; 16: 623-629.
Frisoni, G.B. et al., "Hippocampal and entorhinal cortex atrophy in frontotemporal dementia and Alzheimer's disease", Neurology 1999; 52: 91-100.
Friston, K.J. et al., "Dynamic causal modeling," Neuroimage. 19:1273-1302 (2003).
Friston, K.J., "Functional and Effective connectively in Neuroimaging: A Synthesis", Human Brain Mapping. 1994, vol. 2, pp. 56-78.
Games, D. et al., "Alzheimer-type neuropathology in transgenic mice overexpressing V717F—amyloid precursor protein", Nature 1995; 373: 523-527.
Gerkin, R. et al., "A person's reported history of hypothyroidism is related to apolipoprotein E e4 gene dose", NeuroBiology of Aging 25, S2, 2004, p. 511.
Gerlach, R.W., et al., "Partial least-squares path modeling with latent variables," Anal. Chim. Acta 112:417-421 (1979).
Golomb, J. et al., "Hippocampal atrophy in normal aging—an association with recent memory impairment", Arch Neurol 1993; 50: 967-973.
Golomb, J. et al., "Hippocampal formation size in normal human aging: a correlate of delayed secondary memory performance," Learn. Mem. 1:45-54, May-Jun. 1994.
Golub G, et al. (1989) Matrix Computations, Baltimore, The Johns Hopkins University Press.
Gonzalez-Lima F. et al., "Reduced corpus callosum, fornix and hippocampus in PDAPP transgenic mouse model of Alzheimer's disease", NeuroReport 2001; 12: 2375-2379.
Good, C.D. et al., "A voxel-based morphometric study of ageing in 465 normal adult human brains," Neuroimage, 14:21-36, May 11, 2001.

(56) References Cited

OTHER PUBLICATIONS

Guo, H. et al., "An input function estimation method for FDG-PET human brain studies", Nucl. Med. Biol. 34, 2007, pp. 483-492.
Guo, H. et al., "Clustering huge data sets for parametric PET imaging", Biosystems 71, 2003, pp. 81-92.
Habib, R. et al., "Memory encoding and hippocampally-based novelty/familiarity discrimination networks," Neuropsychologia 41 :271-279 (2003).
Hammers, A. et al., "Implementation and application of a brain template for multiple volumes of interest," Hum. Brain Mapp. 15:165-174 (2001).
Hanson, K.D. et al., "Relation of regional MRI white matter reductions to gray matter in Alzheimer's disease", Society for Neuroscience, 2006.
Hauss-Wegrzyniak, B. et al., "Detecting an experimentally induced reduction in mouse brain volume using sequential high-resolution MRI's and the iterative PCA method", Presented at the 8th Internat Conf on AD and Related Dis, Stockholm, 2002 [abstract].
Haxby, J.V. et al., "Longitudinal study of cerebral metabolic asymmetries and associated neuropsychological patterns in early dementia of the Alzheimer type", Arch Neurol 1990; 47: 753-760.
He, T. et al., "The computation of mannitol-induced changes in mouse brain volume using sequential MRI and an iterative principal component analysis", NeuroBiology of Aging 25, S2, 2004, p. 283.
Higuchi, M. et al., "Regional cerebral glucose utilization is modulated by the dosage of apolipoprotein E type 4 allele and alpha1-antichymotrypsin type A allele in Alzheimer's disease", Neuroreport 1997; 8: 2639-2643.
Hirono, N. et al., "Lack of association of apolipoprotein E epsilon 4 allele dose with cerebral glucose metabolism in Alzheimer disease", Alzheimer Dis Assoc Disord 1998; 12: 362-367.
Hoegaerts, L. et al., "Kernel PLS variants for regression," Proc. of the 11th European Symposium on Artificial Neural Networks 203-208, Apr. 23-25, 2003.
Hoffman, J.M. et al., "FDG PET imaging in patients with pathologically verified dementia", J Nucl Med 2000; 41: 1920-1928.
Holcomb, L. et al., "Accelerated Alzheimer-type phenotype in transgenic mice carrying both mutant amyloid precursor protein and presenilin 1 transgenes", Nature Med 1998; 4: 97-100.
Horwitz, B. et al., "Network analysis of PET-mapped visual pathways in Alzheimer type dementia," Neuroreport 6:2287-2292, Nov. 27, 1995.
Horwitz, B. et al., "Neural modeling, functional brain imaging, and cognition," Trends Cogn Sci. 3:91-98, Mar. 1999.
Horwitz, B., "Functional Interactions in the Brain: Use of Correlations Between Regional Metabolic Rates," Journal of Cerebral Blood Flow and Metabolism 11:A114-A120 (1991).
Höskuldsson, A., "PLS Regression and the Covariance," Chemometrics http://www.acc.umu.se/-tnkjtg/Chemometrics/Editorial, Jul. 2004.
Hsiao, K. et al., "Correlative memory deficits, A elevation, and amyloid plaques in transgenic mice", Science 1996; 274: 99-102.
Huentelman, M. et al., "Calmodulin-binding transcription activator 1 (CAMTA1) alleles predispose human episodic memory performance", Human Molecular Genetics 16, 2007, pp. 1469-1477.
Hwang, D. et al., "Inverse modeling using multi-block PLS to determine the environmental conditions that provide optimal cellular function," Bioinformatics. 20:487-499 (2004).
Hyvarinen, A., et al., "Independent Component Analysis," New York, John Wiley & Sons, Inc. (2001).
Ibanez, V. et al., "Resting state brain glucose metabolism is not reduced in normotensive healthy men during aging, after correction for brain atrophy", Brain Research Bulletin 63, 2004, pp. 147-154.
Ibanez, V., et al., "Regional glucose metabolic abnormalities are not the results of atrophy in Alzheimer's disease," Neurology 50:1585-1593, Jun. 1998.
Jack, C.R. et al., "Medial temporal atrophy on MRI in normal aging and very mild Alzheimer's disease", Neurology 1997;49:786-794.
Jack, C.R. et al., "Prediction of AD with MRI-based hippocampal volume in mild cognitive impairment", Neurology 1999;52:1397-1403.
Jack, C.R. et al., "Rate of medial temporal lobe atrophy in typical aging and Alzheimer's disease", Neurology 1998;51 :993-999.
Jack, C.R. et al., "Rates of hippocampal atrophy correlate with change in clinical status in aging and AD", Neurology 2000;55(4):484-489.
Jack, C.R. et al., "Tangalos EG. MR-based hippocampal volumetry in the diagnosis of Alzheimer's disease", Neurology 1992;42:183-188.
Jagust, W.J. et al., "Longitudinal studies of regional cerebral metabolism in Alzheimer's disease", Neurology, Jun. 1988, 38:909-912.
Jernigan, T. L. et al., "Cerebral structure on MRI, Part I: Localization of age-related changes," Biol. Psychiatry 29:55-67 (1991).
Johnson, S.C. et al., "Activation of brain regions vulnerable to Alzheimer's disease: The effect of mild cognitive impairment", Neurobiology of Aging 27, 2006, pp. 1604-1612.
Johnson, S.C. et al., "Hippocampal adaptation to face repetition in healthy elderly and mild cognitive impairment", Neuropsychologia 42, 2004, pp. 980-989.
Juottonen K. et al., "Volumes of the entorhinal and perirhinal cortices in Alzheimer's disease", Neurobiol Aging 1998;19:15-22.
Juottonen, K. et al., "Comparative MR analysis of the entorhinal cortex and hippocampus in diagnosing Alzheimer disease", AJNR Am J Neuroradiol 1999;20:139-144.
Katzman, R. et al., "The epidemiology of dementia and Alzheimer disease", Terry RD, Katzman R, and Bick KL, eds. Alzheimer Disease. New York: Raven Press, 1994;105-122.
Kaye, J.A. et al., "Volume loss of the hippocampus and temporal lobe in the healthy elderly persons destined to develop dementia", Neurology 1997;48:1297-1304.
Keightley, M.L. et al., "An fMRI study investigating cognitive modulation of brain regions associated with emotional processing of visual stimuli," Neuropsychologia 41 :585-596 (2003).
Kesslak, J. et al., "Quantification of magnetic resonance scans for hippocampal and parahippocampal atrophy in Alzheimer's disease", Neurology 1991;41:51-54.
Khachaturian, Z.S., "The five-five, ten-ten plan for Alzheimer's disease", (editorial). Neurobiol Aging 1992;13:197-198.
Khalil, Z. et al., "Sensory peptides as neuromodulators of wound healing in aged rats", J. Gerontol. Series A: Bio. Sci. and Med. Sci. 1996, vol. 51, No. 5, pp. B354-B361.
Khodr, B., "Effect of short-term and long-term antioxidant therapy on primary and secondary ageing neurovascular processes", J. Gerontol. Series A: Biol. Sci. and Med. Sci. 2003, vol. 58, pp. B698-B708.
Kiebel, S.J. et al., "MRI and PET coregistration—a cross validation of statistical parametric mapping and automated image registration," Neuroimage. 5:271-279 (1997).
Killiany, R. et al., "Temporal lobe regions on magnetic resonance imaging identify patients with early Alzheimer's disease", Arch Neurol 1993;50:949-954.
Killiany, R. et al., "Use of structural magnetic resonance imaging to predict who will get Alzheimer's disease", Ann Neurol 2000;47:430-439.
Klunk, W.E. et al., "Imaging brain amyloid in Alzheimer's disease with Pittsburgh Compound-B," Ann.Neurol. 55:306-319 (2004).
Krasuski, J.S. et al., "Volumes of medial temporal lobe structure in patients with Alzheimer's disease and mild cognitive impairment (and in healthy controls)", Biol Psychiatry 1998;43:60-69.
Kuhl, D.E. et al., "Effects of human aging on patterns of local cerebral glucose utilization determined by the 18F-fluorodeoxyglucose method", J Cereb Blood Flow Metab 1982;2:163-171.
Kuhl, D.E. et al., "In vivo mapping of cerebral acetylcholinesterase activity in aging and Alzheimer's disease", Neurology. 1999;52:691-699.
Laakso, M. et al., "Hippocampal volumes in Alzheimer's disease, Parkinson's disease with and without dementia, and in vascular dementia: an MRI study", Neurology 1996;46:678-681.
Laakso, M. et al., "Volumes of hippocampus, amygdala and frontal lobes in the MRI-based diagnosis of early Alzheimer's disease: correlation with memory functions", J Neural Transm Park Dis Dement Sect 1995;9:73-86.

(56) References Cited

OTHER PUBLICATIONS

Lee, P.C. et al., "Impaired wound healing and angiogenesis in eNOS-deficient mice", Am. J. Physiol. Heart Circ. Physiol. 1999, vol. 277, pp. 1600-1608.

Lehericy, S. et al., "Amygdalohippocampal MR volume measurements in the early stages of Alzheimer disease", Am JNeuroradiol 1994;15:927-937.

Leow, A.D. et al., "For the ADNI preparatory phase study: Longitudinal stability of MRI for mapping brain change using tensor-based morphometry", NeuroImage 31, 2006, pp. 627-640.

Liang, W.S. et al., "Gene expression profiles in anatomically and functionally distinct regions of the normal aged human brain", Physiol Genomics 28: pp. 311-322, 2007.

Iidaka, T. et al., "The effect of divided attention on encoding and retrieval in episodic memory revealed by positron emission tomography," J.Cogn Neurosci. 12:267-280 (2000).

Lin, F.H. et al., "Multivariate analysis of neuronal interactions in the generalized partial least squares framework: simulations and empirical studies," Neuroimage. 20:625-642 (2003).

Lin, L. et al., "MRI template and atlas toolbox for the C57BL/6J Mouse Brain, IEEE EMBS Special Topic Conference on Neural Engineering", Arlington, Virginia, Mar. 16-19, 2005.

Lin, L. et al., "Template based region of interest strategies for measuring ventricular volume in mouse brain MR images: Empirical validation with pharmaceutical-induced ventricular increases", NeuroBiology of Aging 25, S2, 2004, p. 267.

Lobaugh, N.J. et al., "Spatiotemporal analysis of experimental differences in event-related potential data with partial least squares," Psychophysiology 38:517-530 (2001).

Loessner, A. et al., "Regional cerebral function determined by FDG-PET in healthy volunteers: normal patterns and changes with age," J. Nucl. Med. 36:1141-1149, Jul. 1995.

Lopes, J.A. et al., "Multiblock PLS analysis of an industrial phannaceutical process." Biotechnol. Bioeng. 80:419-427, Nov. 20, 2002.

Magistretti, P.J. et al., "Cellular bases of brain energy metabolism and their relevance to functional brain imaging: evidence for a prominent role of astrocytes", Cereb Cortex 1996;6:50-61.

Mahley, R.W., "Apolipoprotein E: cholesterol transport protein with expanding role in cell biology", Science 1988; 240:622-630.

Mark, R.J. et al., "Amyloid-Peptide Impairs Glucose Transport in Hippocampal and Cortical Neurons: Involvement of Membrane Lipid Peroxidation", J Neurosci 1997;17:1046-1054.

Mathis, C.A. et al., "A lipophilic thioflavin-T derivative for positron emission tomography (PET) imaging of amyloid in brain", Biorg Med Chem Lett 2002;12:295-298.

McGeer, E.G. et al., "18Fluorodeoxyglucose positron emission tomography studies in presumed Alzheimer cases, including 13 serial scans", Can J Neurol Sci 1990;17:1-11.

Mcintosh, A.R. et al., "Recruitment of unique neural systems to support visual memory in normal aging," Curr. Biol. 9:1275-1278 (1999).

Mcintosh, A.R. et al., "Spatial pattern analysis of functional brain images using partial least squares," Neuroimage. 3:143-157 (1996).

Mcintosh, A.R. et al., "Structural equation modeling and its application to network analysis in functional brain imaging." Human Brain Mapping 2-22 (1994).

Mcintosh, A.R., "Mapping cognition to the brain through neural interactions," Memory. 7:523-548, (1999).

Mcintosh, A.R., "Understanding neural interactions in learning and memory using functional neuroimaging," Ann. N.Y. Acad. Sci. 855:556-571 (1998).

McKeown, M.J. et al., "Analysis of fMRI data by blind separation into independent spatial components," Hum. Brain Mapp. 6:160-188 (1998).

McKhann, G. et al., "Clinical diagnosis of Alzheimer's disease: report of the NINCDS-ADRDA Work Group under the auspices of the Department of Health and Human Services Task Force on Alzheimer's Disease", Neurology 1984;34:939-944.

Mega, M.S. et al., "Mapping histology to metabolism: coregistration of stained whole-brain sections to premortem PET in Alzheimer's disease", Neuroimage 1997;5:147-153.

Meguro, K. et al., "Neocortical and hippocampal glucose hypometabolism following neurotoxic lesions of the entorhinal and perirhinal cortices in the non-human primate as shown by PET. Implications for Alzheimer's disease", Brain 1999; 122: 1519-1531.

Meltzer, C.C. et al., "Does cerebral blood flow decline in healthy aging? A PET study with partial-volume correction," J. Nucl. Med. 41:1842-1848, Nov. 2000.

Mielke, R. et al., "Apolipoprotein E polymorphism influences the cerebral metabolic pattern in Alzheimer's disease", Neurosci Lett 1998;254:49-52.

Mielke, R. et al., "Clinical deterioration in probable Alzheimer's disease correlates with progressive metabolic impairment of association areas", Dementia 1994;5:36-41.

Minoshima, S. et al., "Posterior cingulate cortex in Alzheimer's disease", Lancet 1994;344:895.

Minoshima, S., et al., "A diagnostic approach in Alzheimer's disease using three-dimensional stereotactic surface projections offluorine-18-FDG PET," J.Nucl.Med. 36:1238-1248 (1995).

Miyata, M. et al., "A polipoprotein E allele-specific antioxidant activity and effects on cytotoxicity by oxidative insults and bamyloid peptides", Nat Genet 1996; 14:55-61.

Moeller, J.R., et al., "Scaled subprofile model: a statistical approach to the analysis of functional patterns in positron emission tomographic data," J. Cereb. Blood Flow Metab. 7:649-658 (1987).

Moritz, C.H. et al., "Whole-brain functional MR imaging activation from a finger-tapping task examined with independent component analysis," AJNR Am. J. Neuroradiol. 21:1629-1635, Oct. 2000.

Morris, J.C. et al., "Cerebral amyloid deposition and diffuse plaques in "normal" aging: Evidence for presymptomatic and very mild Alzheimer's disease", Neurology 1996;46:707-719.

Morris, J.C. et al., "Role of biomarkers in studies of presymptomatic Alzheimer's disease", Alzheimer's & Dementia, Jan. 2005, pp. 145-151.

Murphy, D.G. et al., "Age-related differences in volumes of subcortical nuclei, brain matter, and cerebrospinal fluid in healthy men as measured with magnetic resonance imaging," Arch. Neural. 49:839-845 (1992).

Nestor, P.G. et al., "A new statistical method for testing hypotheses of neuropsychological/MRI relationships in schizophrenia: partial least squares analysis," Schizophr. Res. 53:57-66 (2002).

O'Donnell, B.F. et al., "Identification of neural circuits underlying P300 abnormalities in schizophrenia," Psychophysiology 36:388-398 (1999).

Panza, F. et al., "Cognitive frailty: Predementia syndrome and vascular risk factors", Neurobiology of Aging 27, 2006, pp. 933-940.

Panza, F. et al., "Current epidemiology of mild cognitive impairment and other predementia syndromes", Am J Geriatr Psychiatry 13, 2005, pp. 633-644.

Papassotiropoulos, A. et al., "Common Kibra alleles are associated with human memory performance", Science 314, 2006, pp. 475-478.

Papassotiropoulos, A. et al., "Genetics, transcriptomics and proteomics of Alzheimer's disease", Journal Clinical Psychiatry 67, 2006, pp. 652-670.

PCT Application No. PCT/US2005/021557, International Search Report and Written Opinion dated Sep. 18, 2006.

PCT Application No. PCT/US2005/035608, International Search Report and Written Opinion dated Nov. 22, 2006.

PCT Application No. PCT/US2007/068590, International Search Report and Written Opinion dated Nov. 21, 2007.

Pearson, J.V. et al., "Identification of the Genetic Basis for Complex Disorders by Use of Pooling-Based Genomewide Single-Nucleotide-Polymorphism Association Studies", Am. J. of Human Genetics, vol. 80, pp. 126-139.

Petersen, R.C. et al., "Mild cognitive impairment: clinical characterization and outcome", Arch Neurol. 1999;56:303-308.

Pierce, G.F. et al., "Pharmacologic enhancement of Wound Healing", Annu. Rev. Med. 1995, vol. 46, pp. 467-481.

(56) References Cited

OTHER PUBLICATIONS

Piert, M. et al., "Diminished glucose transport and phosphorylation in Alzheimer's disease determined by dynamic FDG-PET", J Nucl Med 1996;37:201-208.
Pietrini, P. et al., "Regional Glucose Metabolic Abnormalities are not the result of atrophy in Alzheimer's Disease," Neurology 1585-1593, Jun. 1998.
Rajah, M. N. et al., "Frontotemporal interactions in face encoding and recognition," Brain Res. Cogn Brain Res. 8:259-269 (1999).
Rajah, M.N. et al., "Overlap in the functional neural systems involved in semantic and episodic memory retrieval," J. Cogn Neurosci. 17:470-482, Mar. 2005.
Reiman, E.M. et al., "Abnormalities in regional brain activity in young adults at genetic risk for late-onset Alzheimer's disease", Presented at the 8th Internat Conf on AD and Related Dis, Stockholm, Jun. 2002 [abstract].
Reiman, E.M. et al., "Alzheimer's Disease", Maturitas 1999;31:185-200.
Reiman, E.M. et al., "Brain imaging and genomics in the study of cognitively normal persons at differential risk for Alzheimer's disease", Cold Springs Harbor Laboratory Neurodegenerative Diseases Meeting, 2006.
Reiman, E.M. et al., "Cholesterol-Related Genetic Risk Scores are Associated with Hypometabolism in Alzheimer's-Affected Brain Regions", Neuroimage, Apr. 15, 2008; 40(3): pp. 1214-1221.
Reiman, E.M. et al., "Correlations between apolipoprotein E e4 gene dose and brain-imaging measurements of regional hypometabolism", Proceedings of Nat'l Academy of Sciences of the USA, vol. 102, No. 23 (Jun. 2005) pp. 8299-8302.
Reiman, E.M. et al., "Correlations between cholestertol-related genetic risk scores and lower brain-imaging measurements of regional glucose metabolism", Sociology for Neuroscience, 2005.
Reiman, E.M. et al., "Declining brain activity in cognitively normal apolipoprotein E epsilon 4 heterozygotes: A foundation for using positron emission tomography to efficiently test treatments to prevent Alzheimer's disease," Proc. Natl. Acad. Sci. U.S.A 98:3334-3339, Mar. 13, 2001.
Reiman, E.M. et al., "Effects of age on cerebral glucose metabolism in APOE E 4 carriers and noncarriers", Presented at the 8th Internat Conf on AD and Related Dis, Stockholm, Jun. 2002 [abstract].
Reiman, E.M. et al., "FDG PET in cognitively normal persons at genetic risk for Alzheimer's dementia", Arizona Alzheimer's Consortium Annual Meeting, 2003.
Reiman, E.M. et al., "Functional brain abnormalities in young adults at genetic risk for late-onset Alzheimer's dementia," Proc. Natl. Acad. Sci. U.S.A 101:284-289, Jan. 6, 2004.
Reiman, E.M. et al., "Hippocampal volumes in cognitively normal persons at genetic risk for Alzheimer's disease", Ann Neurol 1998;44:288-291.
Reiman, E.M. et al., "Neuroimaging in geriatric psychiatry", Comprehensive Textbook of Psychiatry, 8th Edition, 2005.
Reiman, E.M. et al., "PET Measurements of Posterior Cingulate Glucose metabolism are Superior to MRI Measurements of Hippocampal Volume in Distinguishing Cognitively Normal Persons at Differential Genetic Risk for Alzheimer's Disease", Oral Jan. 5, 2003, Early Detection and Diagnosis 2 p. S177.
Reiman, E.M. et al., "Positron Emission Tomography and Magnetic Resonance Imaging in the Study of Cognitive Normal Persons at Differential Genetic Risk for Alzheimer's Dementia", pp. 1-30.
Reiman, E.M. et al., "Positron emission tomography studies of cognitively normal persons at genetic risk for Alzheimer's disease", Presented at the IPSEN Foundation Conference on the Living Brain and Alzheimer's Disease, Paris, 2003.
Reiman, E.M. et al., "Preclinical evidence of Alzheimer's disease in persons homozygous for the epsilon 4 allele for apolipoprotein E", New England Journal of Medicine 334:752-758, Mar. 21, 1996.
Reiman, E.M. et al., "Preclinical evidence of Alzheimer's disease in persons homozygous for the epsilon 4 allele for apolipoprotein E," N. Engl. J. Med. 334:752-758, Mar. 21, 1996.
Reiman, E.M. et al., "Tracking Alzheimer's disease in transgenic mice using fluorodeoxyglucose autoradiography", NeuroReport 2000;11 :987-991.
Reiman, E.M. et al., "Tracking the decline in cerebral glucose metabolism in persons and laboratory animals at genetic risk for Alzheimer's disease", Clinical Neuroscience Research 2001; 1: 194-206.
Reiman, E.M. et al., "Neuroimaging in the study of amnestic mild cognitive impairment", ICAD, Madrid, 2006.
Reiman, E.M., "Linking Brain Imaging and Genomics in the Study of Alzheimer's Disease and Aging", Ann. N.Y. Acad. Sci. 1097: 94-113 (2007).
Reiman, E.M., "Linking Brain Imaging and Genomics in the Study of Alzheimer's Disease and Aging", Ann. N.Y. Acad. Sci. 1097, pp. 94-113 (2007).
Reiman, E.M., "Proposition: Two Imaging Techniques are Better than One for the Evaluation of Putative Alzheimer's Disease-Slowing Treatments", Preconference—Imaging IM p. S94.
Reiman, EM et al., "Positron emission tomography and magnetic resonance imaging in the study of cognitively normal persons at differential genetic risk for Alzheimer's dementia", The Living Brain and Alzheimer's Disease, 2004, pp. 151-177.
Rusinek, H. et al., "Alzheimer disease: measuring loss of cerebral gray matter with MRI imaging", Radiology 1991 ; 178: 109-114.
Ryan, L. et al., "Neuroimaging: Overview of methods and application", Handbook of Physiological Research Methods in Health Physiological Research Methods in Health Psychology, L.J. Luecken and L.C. Gallo (Eds.), Thousand Oaks, California: Sage Press 2008, pp. 371-394.
Salmon, E. et al., "Decrease of frontal metabolism demonstrated by positron emission tomography in a population of healthy elderly volunteers," Acta Neurol. Belg. 91 :288-295 (1991).
Saunders, A.M. et al., "Association of apolipoprotein E allele e4 with late-onset familial and sporadic Alzheimer's disease", Neurology 1993;43:1467-1472.
Saunders, A.M. et al., "Specificity, sensitivity, and predictive value of apolipoprotein-E genotyping for sporadic Alzheimer's disease", Lancet 1996; 348:90-93.
Scahill, R.I. et al., "Mapping the evolution of regional atrophy in Alzheimer's disease: unbiased analysis of fluid-registered serial MRI", Proc Natl Acad Sci USA 2002;99:4703-4707.
Schaffer, M. et al., "Neuropeptides", Arch. Surg. 1998, vol. 133, pp. 1107-1116.
Schmithorst, V.J. et al., "Comparison of three methods for generating group statistical inferences from independent component analysis of functional magnetic resonance imaging data," J. Magn Reson. Imaging 19:365-368 (2004).
Schneider, L.E. et al., "Metabolic mapping of glucose uptake in PSAPP mouse model of AD: Sensorimotor hyperarousal correlated with auditory amyloid pathology", Neurobiology Aging 25, 2004, S250.
Schott, J.M. et al., "Assessing the onset of structural change in familial Alzheimer's disease", Ann Neurol 2003;53:181-188.
Schuff, N. et al., "Change of hippocampal N-acetyl aspartate and volume in Alzheimer's disease", Neurology 1997;49:1513-1521.
Schwartz, W.I. et al., "Metabolic mapping of functional activity in the hypothalamic neurohypophysial system of the rat", Science 1979;205:723-725.
Seab, J. et al., "Quantitative NMR measurements of hippocampal atrophy in Alzheimer's disease", Magn Reson Med 1988;8:200-208.
Seshadri, S. et al., "Plasma Homocysteine as a Risk Factor for Dementia and Alzheimer's Disease", New Engl J Med; 346: 476-483, Feb. 14, 2002.
Shi, H.P. et al., "Supplemental dietary arginine enhances wound healing in normal but not inducible nitric oxide synthase knockout mice", Surgery, Aug. 2000, vol. 128, No. 2, pp. 374-378.
Shoghi-Jadid, K. et al., "Localization of neurofibrillary tangles (NFTs) and beta-amyloid placques (APs) in the brains of living patients with Alzheimer's disease", Am J Geriatr Psychiatry, Jan.-Feb. 2002; 10, pp. 24-35.

(56) References Cited

OTHER PUBLICATIONS

Silverman, D. et al., "Positron Emission Tomography in Evaluation of Dementia Regional Brain Metabolism and Long-term Outcome," JAMA 286:2120-2127, Nov. 7, 2001.
Small, G.W. et al., "Apolipoprotein E type 4 allele and cerebral glucose metabolism in relatives at risk for familial Alzheimer disease", J Am Med Assoc 1995;273:942-947.
Small, Gary, "Cerebral metabolic and cognitive decline in persons at genetic risk for Alzheimer's disease," Proceedings of the National Academy of Sciences of the United States of America, May 23, 2000, vol. 97, No. 11, pp. 6037-6042, PNAS, Washington D.C., (Category X document, the whole document, abstract, and p. 6037, col. 2, para 3, and p. 6041, col. 2, para 3, relevant to claims 1-23).
Smith, G.S. et al., "Topography of cross-sectional and longitudinal glucose metabolic deficits in Alzheimer's disease", Pathophysiologic implications. Arch Neurol 1992;49:1142-1150.
Smith, J.F. et al., "Network analysis of single-subject fMRI during a finger opposition task", NeuroImage 32, 2006, pp. 325-332.
Snowdon, D.A. et al., "Serum folate and the severity of atrophy of the neocortex in Alzheimer disease: findings from the nun study", Am J Clin Nutr 2000;71 :993-998.
Soininen, H. et al., "Decreased hippocampal volume asymmetry on MRIs in nondemented elderly subjects carrying the apolipoprotein 4 allele", Neurology 1995; 45:391-392.
Solfrizzi, V. et al., "Vascular risk factors, incidence of MCI, and rates of progression to dementia", Neurology 63, 2004, pp. 1882-1891.
Strittmatter, W.J. et al., "Binding of human apolipoprotein E to synthetic amyloid B peptide isoform-specific effects and implications for late-onset Alzheimer disease", Proc Natl Acad Sci USA 1993;90:98-8102.
Strittmatter, W.J. et al., "Hypothesis: microtubule instability and paired helical filament formation in the Alzheimer disease brain are related to apolipoprotein E genotype", Exp Neurol 1994;125:163-171.
Tang, Y. et al., "Introduction: Human Brain Function", Edition II, Frakowiak, RSJ, Friston, KJ, Frith, CD et al.(Eds)., Beijing:China Press, 2006, pp. 790-791.
Teipel, S.J. et al., "Age related cortical gray matter reductions in non-demented Down's syndrome adults determined by MRI with voxel-based morphometry", Brain 127, 2004, pp. 811-824.
Teipel, S.J. et al., "Cortical and sub-cortical changes in preclinical and clinical stages of Alzheimer's disease assessed with magnetic resonance imaging", International Conference on Alz. Dis. Related Disord., Madrid, Spain, 2006.
Teipel, S.J. et al., "Regional pattern of hippocampus and corpus callosum atrophy in Alzheimer's disease in relation to dementia severity: Evidence for early neocortical degeneration", Neurobiol Aging 24, 2003, pp. 85-94.
Teipel, S.J. et al., "Relation of corpus callosum and hippocampal size to age in nondemented adults with downs syndrome", American Journal of Psychiatry 160, 2003, pp. 1870-1878.
Templ,e R., "A regulatory authority's opinion about surrogate endpoints", Nimmo WS, Tucker GT, eds. Clinical Measurement in Drug Evaluation. New York, NY: John Wiley & Sons, Ltd; 1995:3-22.
Terry, R.D. et al., "Neocortical cell counts in normal human adult aging", Ann Neurol 1987; 21:530-539.
Terry, R.D. et al., "Physical basis of cognitive alterations in Alzheimer's disease: synapse loss is the major correlate of cognitive impairment", Ann Neurol 1991;30:572-580.
Terry, R.D. et al., "The Neuropathology of Alzheimer Disease and the Structural Basis of its Cognitive Alterations", Terry RD, Katzman R, Bick KL, and Sisodia SS, eds. Alzheimer Disease, 2nd Ed. Philadelphia: Lippincott Williams & Wilkins 1999; 187-206.
Thal, L. et al., "The role of biomarkers in clinical trials for Alzheimer disease", Alzheimer Dis Assoc Disord 20, 2006, pp. 6-15.
Thompson, P.M. et al., "Cortical change in Alzheimer's disease detected with a disease-specific population-based brain atlas", Cereb Cortex 2001;11:1-16.
Thompson, P.M. et al., "Dynamics of Gray Matter Loss in Alzheimer's Disease", J Neurosci. 2003, 23:994-1005.
U.S. Appl. No. 11/155,711; Final Office Action dated Aug. 4, 2011.
U.S. Appl. No. 11/155,711; Final Office Action dated Mar. 19, 2010.
U.S. Appl. No. 11/155,711; Office Action dated Dec. 7, 2010.
U.S. Appl. No. 11/155,711; Office Action dated Jul. 2, 2009.
Valla, J. et al., "Effects of image resolution on autoradiographic measurements of posterior cingulate activity in PDAPP mice: Implications for functional brain imaging studies in transgenic mouse models of Alzheimer's disease", NeuroImage 2002; 16:1-6.
Valla, J. et al., "Energy hypometabolism in posterior cingulate cortex of Alzheimer's patients: superficial laminar cytochrome oxidase associated with disease duration", J Neurosci. 2001;21:4923-4930.
Valla, J. et al., "Impaired platelet mitochrondrial activity in Alzheimer's disease and mild cognitive impairment", Mitochondrion, Jun. 2006, pp. 323-330.
Valla, J. et al., "Metabolic mapping of cytochrome oxidase activity demonstrates abnormalities in learning/memory circuits in PSAPP double-transgenic mice", Neurobiol. Aging 25, 2005, S246.
Valla, J. et al., "No evidence of significant white matter disruption in the TG2576 mouse model of Alzheimer's disease: Implications for in vivo microimaging", Presented at the 8th Internal Cont on ADd and Related Dis, Stockholm, Jun. 2002 [abstract].
Valla, J. et al., "Nonprogressive transgene-related callosal and hippocampal changes in PDAPP mice", NeuroReport 17, 2006, pp. 829-832.
Visser, P.J. et al., "Medial temporal lobe atrophy and memory dysfunction as predictors for dementia in subjects with mild cognitive impairment", J Neurol 1999;246:477-485.
Webster, J.A. et al., "Sorl1 as an Alzheimer's disease predisposition gene?", Neuro-dengenerative Diseases, 2007, pp. 1-5.
Westerhuis, J.A. et al., "Deflation in multiblock PLS," Journal of Chemometrics 15:485-493 (2001).
Westerhuis, J.A. et al., "Multivariate modelling of the tablet manufacturing process with wet granulation for tablet optimization and in-process control," Int. J. Pharmaceut. 156:109-117 (1997).
Westerhuis, J.A. et al., "Optimization of the composition and production of mannitol/microcrystalline cellulose tablets", Int. J. Pharmaceut, 143:151-162 (1996).
Wheeler-Rice, L. et al., "Individual differences in attentional performance predict verbal learning in healthy elderly", Society for Neuroscience, 2005.
Wisniewski, T. et al., "Acceleration of Alzheimer's Fibril formation by apolipoprotein E in vitro", Am J Pathol 1994;145:1030-1035.
Worsley, K.J. et al., "Characterizing the response of PET and fMRI data using multivariate linear models," Neuroimage. 6:305-319 (1997).
Wu, X. et al., "A variant of logistic transfer function in Infomax and a postprocessing procedure for independent component analysis applied to fMRI data", Magn. Reason. Med., 2007, pp. 703-711.
Xu, Y. et al., "Usefulness of MRI measures of entorhinal cortex versus hippocampus in AD", Neurology, 2000;54:1760-1767.
Young, A.A. et al., "Dose response characteristics for the hyperglycemic, hyperlactemic, hypotensive and hypocalcemic actions of amylin and calcitonin gene-related peptide—I (CGRP alpha) in the fasted, anesthetized rat", Life Sci. 1993, vol. 52, No. 21, pp. 1717-1726.

\* cited by examiner

| Mother X | | | | Daughter Y | | | |
|---|---|---|---|---|---|---|---|
| Height (m) | Weight (kg) | Triglicerides | %Body Fat | Skill #1 (%) | Skill #2 (%) | Skill #3 (1-10) | Skill #4 (1-9) |
| 1.6 | 60 | 111 | 17 | 90 | 88 | 9 | 9 |
| 1.8 | 76 | 131 | 21 | 88 | 77 | 6 | 5 |
| ... | ... | ... | ... | ... | ... | ... | ... |
| ... | ... | ... | ... | ... | ... | ... | ... |
| 2.0 | 90 | 135 | 26 | 60 | 72 | 5 | 4 |

Figure 3

Non-agnostic PLS: PET and MRI

Figure 10

METHODOLOGIES LINKING PATTERNS FROM MULTI-MODALITY DATASETS

CROSS REFERENCES TO RELATED APPLICATIONS

This application is a continuation of and claims the priority benefit of U.S. patent application Ser. No. 11/242,820 filed on Oct. 3, 2005, which claims priority to U.S. Provisional Application No. 60/615,767 filed on Oct. 4, 2004, titled "Neuroimaging Methods and Systems", the entire contents of which are incorporated herein by reference.

FIELD OF INVENTION

This invention relates to imaging, and more particularly relates to general computational mathematical methodologies linking multi-modality imaging and non-imaging datasets for valuating an effect upon objects from which data in the datasets is obtained, and most particularly related to biomathematical methodologies linking multi-modality neuroimaging and non-imaging datasets for characterizing patient group differences and for valuating the efficacy of treatments for neurological, psychiatric, and related disorders upon human subjects from whom data in the datasets is obtained.

BACKGROUND

Neuroimaging researchers frequently acquire multi-modality image data and various non-imaging measurements. For example, FDG-PET and structural (e.g., volumetric) MRI brain images as well as a complete battery of neuropsychological tests are acquired from each healthy subject every two years in our NIH sponsored longitudinal APOE-ε4 study. In their study of imaging neurofibrillary tangles and beta amyloid plaques using 2-(1-[6-[(2-[18 F]fluoroethyl)(methyl)amino]-2-naphthyl]ethyli-dene)Malononitrile (FDDNP) (Shoghi-Jadid, K. et al. 2002), Researchers from UCLA acquired triple imaging datasets, FDG-PET, FDDNP-PET and T1 weighted volumetric MRI. Similarly, Researchers at the University of Pittsburgh used dual PET tracers, FDG and PIB in their study of imaging brain amyloid in AD (Klunk, W. E. et al. 2004). The availability of multi-modality imaging datasets provides researchers an opportunity to examine multi-processes simultaneously and yet poses a methodological challenge in having the multi-datasets optimally integrated and utilized for the understanding of the underlining biological system.

There have existed methods that make use of data from one image modality for the analysis of another. People have long used image fusion technique for localizing functional findings with the anatomical map provided by structural images (as an example, see (Reiman, E. M. et al. 2004)). Similarly, region of interest (ROI) defined on the anatomical images can be used to extract data from functional dataset to investigate experimental condition manipulated brain responses. Taking the advantage of high resolution, volumetric MRI has also been routinely used to correct the combined effects of partial volume average and atrophy related to the functional images (Pietrini, P. et al. 1998). In the FDG-PET study, this correction allows researchers to determine if the underlining cause of the observed brain functional alternations is purely glucose metabolic pathway or mostly the structural relate (Reiman, Chen, Alexander, Caselli, Bandy, Osborne, Saunders, and Hardy 2004). Besides these procedures listed here and used in mostly structural-functional studies, findings from one imaging modality are often correlated with the that from another imaging modality or from non-imaging measurement using conventional correlation analysis (Shoghi-Jadid, Small, Agdeppa, Kepe, Ercoli, Siddarth, Read, Satyamurthy, Petric, Huang, and Barrio 2002). Overall, the approaches listed here are relative straightforward and mostly in the context of analyzing primarily the data from one single-modality using another, supportive and secondary. In contrast, our approach proposed in the current study, multi-modality, inter-networks and multivariate in nature, is to establish the optimal way to link multi-datasets and to combine the information from each of the datasets for enhancing researcher's ability to detect alternations related to the experimental conditions or the onset, progress or treatments related to the study of diseases.

As mentioned above, our approach will be multivariate in nature. Multivariate analysis has been long used in single-modality studies complementary to univariate analysis. These single-modality, intra-network and multivariate analysis, model-based or data-driven, are to characterize brain inter-regional covariances/correlations. These methods, voxel- or ROI-based, included principal component analysis (PCA) (Friston, K. J 1994), the PCA-based Scaled Subprofile Model (SSM) (Alexander, G E and Moeller, J R 1994), independent component analysis (McKeown, M. J. et al. 1998; Duann, J. R. et al. 2002) (McKeown, Makeig, Brown, Jung, Kindermann, Bell, and Sejnowski 1998; Arfanakis, K. et al. 2000; Moritz, C. H. et al. 2000; Calhoun, V. D. et al. 2001; Chen, H. et al. 2002; Esposito, F. et al. 2003; Calhoun, V. D. et al. 2003; Schmithorst, V. J. and Holland, S. K. 2004; Beckmann, C. F. and Smith, S. M. 2004) and the Partial Least Squares (PLS) method (McIntosh et al. 1996; Worsley, K. J. et al. 1997). Also included are Multiple correlation analysis (Horwitz, B 1991; Horwitz, B. et al. 1999), structure equation model (Mcintosh, A. R. and Gonzalez-Lima, F 1994; Horwitz, Tagamets, and McIntosh 1999), path analysis (Horwitz, B. et al. 1995; Worsley, K. J. et al. 1997), and dynamic causal modeling (Friston, K. J. et al. 2003). These methods have typically been used to characterize regional networks of brain function (and more recently brain gray matter concentration (Alexander, G et al. 2001)) and to test their relation to measures of behavior. No one of these multivariate methods, however, has been used to identify patterns of regional covariance among multi-imaging datasets.

Motivated by the availability of the multi-neuroimaging datasets and encouraged by the success of single-modality network analysis, especially the PLS works, we set out searching for tools that allow us to seek for the maximal linkage among the multi-datasets or to optimally combine them for increased statistical powers. We believe dual-block PLS (DBPLS) as well as multi-block PLS (MBPLS) should be the first set of tools we would like to explore for such purpose. We will list the challenges and difficulties in performing inter-modality analysis using PLS and our very own plan for further methodological development later. First, however, a review is in demand for the general PLS methodology, the success of DBPLS in the neuroimaging field (mainly by McIntosh and his colleagues) and that of MBPLS mainly in the chemometrics and bioinformatics areas.

Review of the PLS Method

Citing from the *Encyclopedia for research methods for the social sciences*, PLS regression is a relative recent technique that generalizes and combines features from PCA and multiple regressions. It is particularly useful when one needs to predict a set of dependent variables from large set(s) of independent variables (Abdi, H. 2003).

The traditional use of PLS regression is to predict (not to link) dependent dataset Y from c (c≥1) independent datasets $X_1, \ldots X_c$, hence the term of PLS regression. Note that in this writing the variables in each dataset are arranged column-wise in the data matrix. In addition to the PLS regression, we are also interested in its use to describe the linkages among multi-dataset without the labeling of dependent or independent. With details of the PLS linkage methodology developments to be described later, we provide here a review of the PLS regression methodology. In a sense, PLS is not needed when Y is a vector (single variable dataset) and X is full rank (assuming c=1) as the Y-X relationship could be accomplished using ordinary multiple regression. For our neuroimaging studies, especially our inter-network analysis, the number of voxels/variables is greater than one, and in fact much larger than the number of subjects/scans, multicollinearity exists for each dataset. Several approaches have been developed to cope with this problem when Y is a vector (which is not the case in our neuroimaging study). The approach, called principal component regression, has been proposed to perform a principal component analysis (PCA) of the X matrix and then use the principal components of X as regressors on Y. Though the orthogonality of the principal components eliminates the multicollinearity problem, nothing guarantees that the principal components, which explain X, are relevant for Y (Abdi 2003). By contrast, PLS regression finds components from X that are also relevant for Y. Specially, PLS regression searches for a set of components that performs a simultaneous decomposition of X and Y with the constraint that these components explain as much as possible of the covariance between X and Y (Abdi 2003). The procedure of finding the first PLS regressor is equivalent to maximize the covariance between a linear combination of the variables in Y and a linear combination of the variables in X (the paired linear combinations are referred to as the first latent variable pair). This maximal covariance is symmetrical for Y and X for this first latent variable pair. Symmetry here is referred to as the irrelevancy of the fact which dataset is designated as dependent. The symmetry is lost for subsequent latent pairs, however, as is demonstrated below.

DBPLS Algorithm:

As mentioned above, DBPLS uncovers the sequential maximal covariance between two datasets by constructing a series of latent variable pairs. Starting from original data matrices X and Y (with standardization necessary), the first latent variable pair is constructed as follows. The latent variable of X is $t=\Sigma w_i x_i$ where $w_i$ is scalar, and $x_i$ is the $i^{th}$ column of X (i=1, 2, . . . ). In matrix form, t=Xw where $w=(w_1, w_2, \ldots)^T$ with $\|w\|=1$. Similarly, the Y latent variable can be expressed as u=Yc ($\|c\|=1$). In the context of dual-imaging datasets and for matter of convenience, we will refer w and c as singular image of X and Y respectively. The covariance of the two latent variables, t and u, is therefore cov(t,u)=w'X'Yc (assuming zero mean for variables in both datasets). The maximal covariance value with respect to w and c can be proven to be the square root of the largest eigenvalue of the matrix $\Omega=[X'YY'X]$ with w being the corresponding eigenvector of $\Omega$, and c being the corresponding eigenvector of Y'XX'Y. Prior to the second latent variable pair, the effects of the first latent variable pair needs to be regressed out from X and Y, referred as deflation in the chemometrics PLS literature:

Express and $$p_1 = \frac{X't}{\|t\|^2}, q_1 = \frac{Y'u}{\|u\|^2}, r_1 = \frac{Y't}{\|t\|^2}$$

and calculate new $X_1$ and $Y_1$ as $X_1=X-tp_1'$ $Y_1=Y-tr_1'$

The same calculating procedure will then be repeated for the new $X_1$ and $Y_1$ matrix pair to construct the second latent variable pair. The third and remaining latent variable pairs (up to the rank of X) will be calculated similarly.

MBPLS Algorithm:

The calculation of MBPLS is based on the DBPLS procedure described above, with some kind scheme of deflation to take care of the presence of more than one independent block. Westerhuis et al described the following numerical procedure (Westerhuis, J. A. and Smilde, A. K. 2001):

1, Calculate the first latent variable pair of the DBPLS model between $X=[X_1, \ldots, X_c]$ and Y. The scores t and u, weight w and loadings p and q are obtained. From these, the multiblock PLS block weights $w_b$, the super weights ws and the block scores $t_b$ are obtained.

2, $w_b=w(b)/\|w(b)\|^2$
3, $t_b=X_b w_b$
4, $ws(b)=t_b^T u/u^T u$
5, $ws=ws/\|ws\|^2$

Block score deflation

6a, $p_b=X_b^T t_b/t_b^T t_b$
7a, $E_b=X_b-t_b p_b$
8a, F=Y-tq

Super score deflation

6b, $E_b=X_b-tp(b)^T$
7b, F=Y-tq

For additional components, set $X=[E_1, \ldots, E_c]$ and Y=F and go back to step 1.

Different deflation step can be used playing a crucial part in MBPLS calculation. The block score deflation, suggested by Gerlach and Kowalski (Gerlach, R. W. and Kowalski, B. R. 1979), led to inferior prediction. Westerhuis et al. showed that super score deflation gave the same results as when all variables were kept in a large X-block and a DBPLS model was built. The super scores summarize the information contained in all blocks, whereas the block scores summarize the information of a specific block. However, the super score deflation method mixes variation between the separated blocks and therefore leads to interpretation problems. In order to overcome the mixing up of the blocks, deflating only Y using the super scores was proposed (Westerhuis and Smilde 2001). This leads to the same predictions as with super score deflation of X, but because X is not deflated, the information in the blocks is not mixed up.

Review of DBPLS in the intra-modality neuroimaging studies

McIntosh and his colleagues first introduced DBPLS into the neuroimaging field in 1996 (McIntosh, Bookstein, Haxby, and Grady 1996) for the intra-modality spatial pattern analysis in relationship to behavior or experimental conditions. Consequent to this study, Worsley considered an alternative PLS procedure, what he referred to as the ortho-normalized PLS (Worsley, Poline, Friston, and Evans 1997) to account for the issue of being invariant to arbitrary linear transformations. Ever since, DBPLS works have been extended, improved and introduced extensively to various brain studies mainly by McIntosh and his group. Their efforts included further methodological developments such as the extension from PET to functional MRI studies, from the original PLS to seed-PLS (McIntosh, A. R. et al. 1999) or spatiotemporal-PLS (Lobaugh, N. J. et al. 2001; Lin, F. H. et al. 2003) and numerous applications in brain function/disease studies (McIntosh, A. R. 1998; McIntosh, A. R. 1999; Rajah, M. N. et al. 1999; O'Donnell, B. F. et al. 1999; Anderson, N. D. et al. 2000; Iidaka, T. et al. 2000; Lobaugh, West, and McIntosh 2001; Nestor, P. G. et al. 2002; Keightley, M. L. et al. 2003; Habib, R. et al. 2003). Another significant contribution from McIntosh's group is the introduction of the non-parametric inference procedures, permutation or Bootstrapping for intra-modality PLS neuroimaging studies (for example, see the initial introduction paper (McIntosh, Bookstein, Haxby, and Grady 1996)).

Review of DBPLS in the Inter-Modality Neuroimaging Studies

Presented on the World Congress on Medical Physics and Biomedical Engineering at Sydney, Australia in 2003 (Chen, K et al. 2003), our group reported the inter-network preliminary results linking FDG-PET to MRI segmented gray matter overcoming a huge computing obstacle related to the size of the covariance matrix between two imaging datasets (number of voxel in one image data set x the number of voxels in another). Our aim is to seek direct linkage or regression between dual-modality imaging datasets (MB-PLS regression or MBPLS linkage analysis).

One year later, researchers from McIntosh's group reported alternative approaches for analyzing multi-modality imaging data at 13th Annual Rotman Research Institute Conference Mar. 17-18, 2004 (Chau, W et al. 2004). They used the same operational procedure as in their intra-modality PLS studies in attempting to answer the same question: the experimental condition or behavior related neuroimaging covarying patterns. In other words, the roles of neuroimaging datasets are only and always the X's blocks in the PLS regression notation above with the experimental conditions or behavior data as the dependent Y block (Chau, Habib, and McIntosh 2004). Since the direct linkage between/among multi-modality datasets is not the purpose of their investigation, there exist no needs to computationally deal with the issue of the covariance matrix sizes. Also, since the number of X blocks is more than one, investigation on the deflation scheme is needed, but not was considered in their study.

Review of DBPLS and MBPLS in Chemometrics and Bioinformatics

Though the successes of the DBPLS in the neuroimaging field have been indeed impressive, the application of MBPLS in this field is yet to be matured, its success demonstrated, and new algorithms developed. Numerous successful applications of both DBPLS and MBPLS, however, have been reported in the field of fermentation and granulation for food or pharmacological industries. The importance of PLS in Chemometrics field is evidenced by the online editorial in the Journal of Chemometrics (Hiskuldsson, A 2004). An incomplete MBPLS review in these fields is provided here together with some discussion on their relevance to our intended neuroimaging applications.

Esbensen at al., analyzed data of the electronic tongue (an array of 30 non-specific potentiometric chemical sensors) using PLS regression for qualitative and quantitative monitoring of a batch fermentation process of starting culture for light cheese production (Esbensen, K. et al. 2004). They demonstrated that the PLS generated control charts allow discrimination of samples from fermentation batches run under "abnormal" operating conditions from "normal" ones at as early as 30-50% of fully evolved fermentations (Esbensen, Kirsanov, Legin, Rudnitskaya, Mortensen, Pedersen, Vognsen, Makarychev-Mikhailov, and Vlasov 2004). Relevant to our proposal, this study is a clear demonstration of the MBPLS prediction power based on multi historical datasets, the power that a physician dreams to duplicate for early diagnosis of a disease.

In another study (Lopes, J. A. et al. 2002), the performance of an industrial pharmaceutical process (production of an active pharmaceutical ingredient by fermentation) was modeled by MBPLS. With the multiblock approach, the authors were able to calculate weights and scores for each independent block (defined as manipulated or quality variables for different process stage). They found that the inoculum quality variables had high influence on the final active product ingredient (API) production for nominal fermentations. For the non-nominal fermentations, the manipulated variables operated on the fermentation stage explained the amount of API obtained. As demonstrated in this study, the contributions of individual data blocks to the final output can be determined. The neuroimaging analog of their study is to use PLS to evaluate the relative contribution of various datasets (MRI, FDG-PET, neuro-psychological tests) in accurately predicting the onset of AD or in evaluating the effects of treatments.

Hwang and colleagues discussed the MBPLS application to the field of tissue engineering in one of their recent publications (Hwang, D. et al. 2004). They used MBPLS model to relate environmental factors and fluxes to levels of intracellular lipids and urea synthesis. The MBPLS model enabled them to identify (1) the most influential environmental factors and (2) how the metabolic pathways are altered by these factors. Moreover, the authors inverted the MBPLS model to determine the concentrations and types of environmental factors required to obtain the most economical solution for achieving optimal levels of cellular function for practical situations. The multi datasets (or multi-groups as referred by them) included the group of environmental factors and C groups, each of them consisting of a number of metabolites and fluxes that have similar metabolic behaviors. Like the one by Lopes et al., this study illustrates the power of MBPLS to assess the relative importance of each independent dataset in predicting the behavior of interests. Moreover, this study showcases the use of MBPLS to determine the variable combinations that give rise to the optimal level of the dependent variables.

Note that the MBPLS applications reviewed above are all in the framework of multiple-independent (predictor) blocks and a single dependent block, all consisting of no more than N number of variables, where N is a ten-thousand times smaller than the number of voxels/variables in the neuroimaging datasets.

Relative to neuroimaging, a major challenge to the multivariate analysis of regional covariance with multiple imaging modalities is the extremely high dimensionality of the data matrix created by including relatively high-resolution neuroimaging datasets. What is needed is a strategy to make computation of high dimensional datasets using multivariate methods feasible.

SUMMARY

Mathematical methodologies are disclosed to find a linkage between imaging and non-imaging datasets. The linkage is used to find relationships among datasets, to combine, summarize information from multi-datasets, and to construct new numerical surrogate markers for increased statistical power in the evaluation of the status of objects, both manmade and biological, such as for the evaluation of humans and possible early treatment and prevention strategies in the fights against a disease (such as Alzheimer Disease).

Implementations disclose a request to acquire a plurality of datasets from each of a plurality of objects. A linkage exists between these datasets, where each dataset is potentially a different modality (e.g., imaging and non-imaging datasets). The linkage between datasets can be found using a partial least squares (PLS) technique, including Dual Block (DB) PLS or Multi-block (MB) PLS with the conventional criterion or the one established as disclosed herein. Moreover, we also disclose other analytical techniques for finding the linkage. The linkage is then reduced to an expression of a single numerical assessment. Alternatively, the linkage can be reduced to a unique solution that can be characterized by several numbers for each of the assessed modalities.

The single numerical assessment is then used as an objective, quantified assessment of the differences and similarities between the objects. The data in the plurality of datasets, as mentioned, can be acquired either by an imaging modality or a non-imaging modality. The data in each dataset can be an index, such as an aspect of performance, a physical characteristic, a measurement of appearance, or numerical representation of the inner status of the objects such as the glucose uptake rates/gray matter concentrations from various human brain regions.

BRIEF DESCRIPTION OF THE DRAWINGS

A more complete understanding of the implementations may be had by reference to the following detailed description when taken in conjunction with the accompanying drawings wherein:

FIG. 3 illustrates the potential use of a PLS method, where one is interested in investigating a debatable relationship between mothers' fitness and daughters' cognitive skills, where the X matrix X lists the mothers' physical characteristics measurements, and the Y matrix lists the daughter's cognitive skill measurements;

FIG. 10 shows the PLS singular images obtained by the non-agnostic partial least squares processing, where this is for the preliminary PET and MRI human brain studies, where similarities of the singular images are apparent in comparison to the results of the agnostic approach as seen in FIG. 2B;

DETAILED DESCRIPTION

Figure 1:
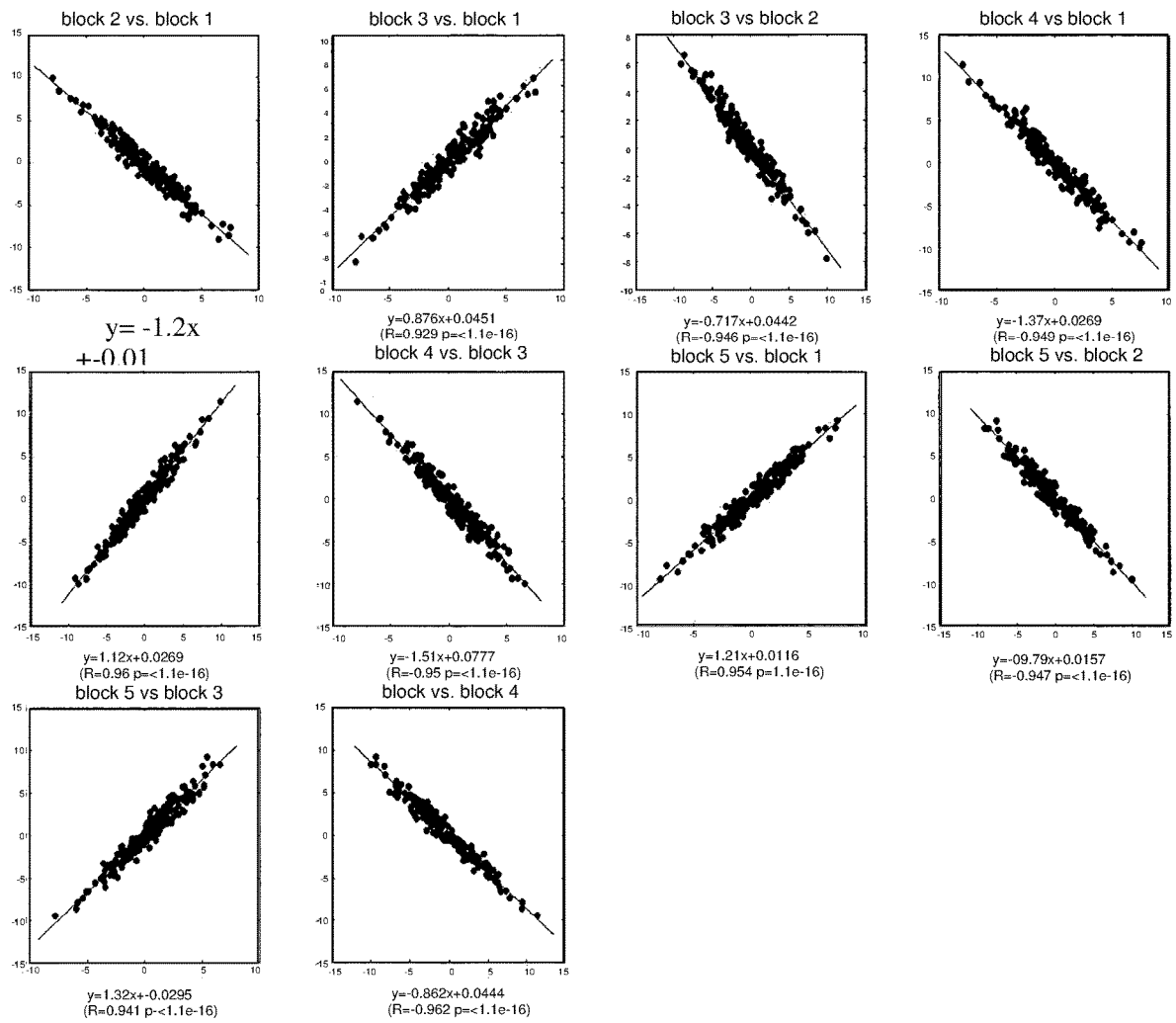
FIG. 1 shows close correlation between each of 10 possible pairs in a 5 block PLS analysis using our newly defined criteria which do not need labels of dependent or independent datablocks.

Mathematical methodologies are developed and implemented to seek linkage first between dual-modality and then extended to among multi-modality neuroimaging and non-imaging datasets. The methodologies allow researchers to find relationships among datasets, to combine, summarize information from multi-datasets, and to construct new numerical surrogate marker of neuroimaging for increased statistical power in the evaluation of possible early treatment and prevention strategies in the fights against a disease (such as Alzheimer Disease).

The idea of multi-modality inter-network analysis using partial least square (PLS) technique. Our group is the first suggesting to investigate the direct linkage among multi-imaging datasets, and to combine information from multi-datasets for increase statistical power with the use of PLS.

The numerical strategy to make the calculation of PLS with covariance matrix of huge size feasible on a personal desktop/laptop computer. We come out the way to divide into small pieces a huge matrix that no computer can just simply hold it in memory. Thus, the computation the inter-network PLS becomes feasible on a modern desktop/laptop computer. See C.1 Implementation of DBPLS for voxel-based neuroimaging data.

The special application of the algorithm to seek covarying patterns among multi-modality neuroimaging datasets for the study of Alzheimer disease (AD), risk of AD, evaluation of early treatment or prevention of AD. We propose to look the covaried-pattern changes across multi-modalities, and to use latent variable pairs as multivariate index (indices) for the calculation of statistical power via Monte-Carlo simulation and believe the indices are with improved sensitivity and without the need to correct for multiple comparisons. See C.2. Assessment of Statistical Significance, D. 1 and D. 3

The idea and application of the algorithm to seek covarying patterns between imaging and non-imaging datasets as a tool for diagnosis. We proposed to generalize our initial PLS AD application to other disease diagnosis such breast cancer with mammography and breast MRI, and to other research areas such as the search of linkage between neuroimaging data and genomic information. See III.3 of A, specific aims. D. 1.5

The re-definition of the multi-block PLS as a procedure to seek covarying patterns among all blocks without designating one block as dependent block and others as independent blocks. The conventional PLS is in the frame work of predicting a single dependent block based on the observation of one or more independent blocks. We ask the question of seeking relationship among inter-dependent multi-blocks. With that redefinition, we introduce various alternative object functions and algorithms to seek the solution of the newly defined multi-block PLS. See D.4.1

The theoretical findings of mathematical and theoretical discussions on the multi-block PLS re-definition for the existence and uniqueness of its solution. We will discuss conditions under which there exists one and only one solution for the newly introduced object function. See the Appendix.

The applications of the newly defined multi-block PLS approach to study the inter-network relationship between multi-modality neuroimaging datasets especially in the study of AD.

The conceptual introduction of inter-system independent component analysis (inter-ICA) and inter-system structural equation modeling (inter-SEM). ICA has been widely used in constructing a set of statistical independent components for a single dataset (one system). We put forward the idea of inter-system ICA and proposed algorithm to have that realized. Similar comments can be made for inter-system SEM. See D. 4.3

A. Specific Aims

The overall goal is to develop multivariate analysis algorithms for analyzing multi-modality neuroimaging and non-imaging datasets in a systematic inter-network approach. With this analytical tool, we aim to a) study the linkage among imaging/non-imaging datasets, b) to investigate relevant importance of each dataset, as a whole, in contributing to the predictability of brain functions, brain disease onset, clinical outcomes in general or treatment evaluation, and c) to apply the developed algorithms to various neuroimaging studies including especially our longitudinal study of the genetic risks of Alzheimer disease (AD) associated with the apolipoprotein ε4 (APOE-ε4) alleles.

Two versions of partial least square (PLS) technique, dual-block PLS (DBPLS) and multi-block PLS (MBPLS) will be investigated for our inter-modality methodology endeavor. It is worth to note that DBPLS has successful applications in intra/single-modality neuroimaging studies (McIntosh, A. R. et al. 1996).

The specific aims can be categorized as methodological developments, general biomedical applications and the special application to AD neuroimaging studies:

I: Answer the Methodological Development Challenges

I.1, Developing/Implementing inter-modality and voxel based or region of interest based DBPLS/MBPLS algorithm. Strategies will be planned to overcome the difficulty associated with the extremely high size of the dual-imaging dataset covariance matrix.

I.2, Assessing the statistical power and type-I errors of the PLS uncovered inter-modality networks. Efficient non-parametric procedure and Monte-Carlo simulation will be proposed for such purposes.

I.3, Maximizing the linkage strength among datasets based on newly proposed MBPLS object functions. In addition to the fact that MBPLS only seeks the maximal linkage between the dependent dataset and the set of independent datasets, we propose to investigate the simultaneous maximization of covariances (or other index of linkage strength) of each of all possible dataset pairs.

II: Answer the Data Analysis Challenges in General Biomedical Neuroimaging/Non-Imaging Studies II.1, Providing a tool to study the inter-network relationship among multi-datasets. With this tool, for example, one could examine how the glucose uptake pattern over various brain regions measured by F-18 fluoro-2-deoxyglucose (FDG) and positron emission tomography (PET) is related to the spatial distribution of segmented gray matter volume measured by magnetic resonance imaging (MRI). Another example, one can use this tool to study the global pattern linkage among cerebral glucose uptake (by FDG-PET), the distribution of amyloid plaques (by N-methyl-[C-11]2-(4'-methylaminophenyl)-6-hydroxybenzothiazole (PIB)-PET), and gray matter spatial pattern (by MRI).

II.2, Making available a means to combine and integrate the information from multi systems/datasets for increased statistical power for treatment evaluation, risk assessment or clinical diagnosis.

II.3, Offering a procedure to assess relative importance of each dataset in predicting the clinical outcomes and in evaluating treatments.

II.4, Initiating our efforts to study other mathematical algorithms for inter-network relationship in addition to PLS. Among the alternative multi-dataset analysis tools are the inter-network independent component analysis (ICA) and the inter-network structural equation modeling (SEM).

III: Answer the Data Analysis Challenges Especially in the Neuroimaging Studies of Ad and AD Risk, and in Other Medical Research Areas III.1, developing a prediction scheme using cross sectional and longitudinal FDG-PET and MRI data (and possibly together with neuropsychological data) to assess the risk for the symptomatic onset of the clinical AD for healthy individuals carrying 0, 1 or 2 copies of APOE-ε4 allele (PLS application to data acquired with the support of NIMH MH057899-06)

III.2, constructing a clinical diagnostic scheme using cross sectional and longitudinal FDG-PET and MRI data (and possibly together with neuropsychological data) to calculate the probability and average time duration an MCI patient converts to AD III.3, exploring the possibility of applying PLS to other medical research and clinical areas where the multi-modality [non-]imaging datasets need to be combined or evaluated. An example would be the mammography and breast MRI.

Methodological Challenges

With our specific aims in mind, our focuses will be to propose, implement and evaluate strategies to conquer challenges listed here.

I. Demonstrate the need and the power of the inter-network analysis in neuroimaging studies. Please see the Significance session and the Preliminary Results session for details.

II. Make the computation feasible for the inter-network neuroimaging PLS analysis To illustrate the computational challenge using dual-imaging dataset DBPLS as an example, let us consider the size of images used in a typical Statistical Parametric Mapping (SPM) PET analysis with 2 mm cubic voxel. Note that Statistical Parametric Mapping refers to the construction and assessment of spatially extended statistical processes used to test hypotheses about functional imaging data, such by the use of software also called SPM (http://www.fil.ion.ucl.ac.uk/spm/). SPM software can be used for the analysis of brain imaging data sequences. The sequences can be a series of images from different cohorts, or time-series from the same subject. SPM software can be for the analysis of fMRI, PET, SPECT, EEG, and MEG.

The number of brain voxels could be 246,082 (almost a quarter millions). If this number is for both datasets in a dual-network PLS analysis, then the covariance matrix will be 246,082 by 246,082. The same calculation difficulty exists for the newly introduced object function in this study (more on this below). Implementation feasibility is important not only for the inter-network PLS itself, but more for its type-I error and statistical power computation (below).

III. Further develop PLS procedure in answering challenges in the neuroimaging research area.

Type-I error and statistical power assessment: For assessing the statistical significance (type-I error) of various aspects related to the uncovered covarying patterns and correlations between two datasets or among multi-datasets, non-parametric approaches such as Jacknife, bootstrap and permutations (permissible with experimental designs) resampling techniques as well as Monte-Carlo simulations will be adopted which, except our own proposed Monte-Carlo simulation, have been demonstrated their usefulness in the DBPLS intra-modality neuroimaging studies (McIntosh, Bookstein, Haxby, and Grady 1996). Moreover, in order to propose a single PLS index or a set of PLS indices as surrogate marker in designing new studies such as treatment evaluations, we need to calculate the statistical power.

New MBPLS linkage strength indices establishment: For the MBPLS case where no meaningful dependent/independent labels can be assigned to each dataset, we intend to institute a new object function in finding the maximum linkage strength among these multi-datasets. This is in addition to the MBPLS algorithm that seeks the maximal linkage between the dependent dataset and the set of independent datasets. We will investigate the feasibility of simultaneously maximizing all covariances (or other index of linkage strength), one for each possible dataset pair among all datasets. Mathematically, the existence and uniqueness of this new object function's global maxima will be discussed.

Additional alternative inter-network analysis tool investigation: In addition to PLS, other methodologies will be explored for analyzing multi-modality neuroimaging/non-imaging datasets. See Experimental design & Methods section for more.

Significance:

Bio-mathematical methodology development: To our knowledge, our proposed multi-modality inter-network analysis approach is the first of this kind. It is our attempt to answer the call of analyzing multi-datasets of unusual sizes simultaneously and in a systematic manner. Aside from its relevancy to the biomedical especially neuroimaging studies, methodological questions raised in this endeavor are mathematically challenging. They will for sure initiate and stimulate necessary theoretical discussions which in turn will provide insights on the proposed approach's application and further development. Though our primary focuses of the current proposal will not be mathematical theorem oriented, we will be just as rigorous in introducing various alternative object functions for MBPLS, in proposing related optimization strategies, and in defining small probability events in the calculation of the type-I errors and statistical powers. Furthermore, our logically constructed Monte-Carlo simulations will be inspiring for the further pursue of mathematical theorem oriented discussions. In this study, we will not only attempt to define these biomedically relevant challenges, but also actively initiate the communication with theoretically oriented mathematician/statisticians to advance the developments.

Neuroimaging multi-biological process analysis procedure: We believe our inter-network multi-modality PLS is not a simple extension of the intra-modality PLS method. Rather it is novel in several facets. First, the inter-network PLS seeks direct linkage among images of different modalities. The linkage strengths and the singular images provide information complementary to that given by analysis of each image dataset alone, univariate or multivariate. With this direct linkage approach, different multi-physiological/metabolic processes and anatomical structural information can be investigated and cross-referenced. Moreover, this multiple process investigation can be performed with or without in reference to experimental conditions or behavior measurement (i.e., all under rest condition). Secondly, the proposed global index (or a set of global indices) combined with some pre-specified nodes on the singular image set as surrogate markers is innovative together with the Monte-Carlo simulation for the statistical power and type-I error calculation (see Research Plan). Finally, computation strategies will be developed to make the proposed multi-modality inter-network analysis procedure feasible.

Inter-network multi-modality analysis tool for Alzheimer disease study: With this inter-network analysis tool, the relationship between brain structure and brain function, for example, can be investigated helping us to evaluate differential genetic risks of AD associated with 0, 1 or 2 copies of APOE-ε4 allele in our NIH sponsored on-going longitudinal neuroimaging study. Similarly, this tool can also be very helpful to understand the progression of AD disease, the conversion from mild cognitive impairment (MC) to AD in the other NIH-sponsored Alzheimer Disease Neuroimaging Initiative (ADNI) study (see D.1 data section for more).

Potential applications to other biomedical research/clinical areas: We believe that PLS is a tool not only for the imaging datasets, but also for others as well such as those from genomics or bioinformatics. For example, the linkage among the brain structure, brain function and the genomic makeup can be characterized and explored with the use of MBPLS. Efforts will be made so the implementation of the algorithm as generic and applicable as to data not only from the neuroimaging studies but from multi-fields.

Finally, it is worth to note the need for us to consider the alternative MBPLS object function for the study of the linkage among them without designating one dataset as dependent dataset and others as predictors. To study the PIB-FDG pattern in relation to FDG-PET and volumetric MRI, for example, one can certainly treat PIB-FDG dataset as dependent datablock. However, a relationship among these three datasets with same labeling could provide fair view of the data.

C. Preliminary Studies

C.1 Implementation of DBPLS for Voxel-Based Neuroimaging Data

C.1.1 the Iterative Way to Compute PLS: Power Algorithm

With the notation introduced earlier, it is obvious that the size of the square matrix $\Omega$ is the number of voxels within the brain volume (assuming the same number of voxels for both imaging datasets).

To make the computation possible, we partition each of the huge matrices (X, Y, $\Omega$ and other intermediate ones) into a series of small matrices which are only read in, one at a time, into the computer memory when needed. To make this strategy works, the only allowed matrix operations are those that can act separately on sub-matrices and result in sub-matrix form. One example of such operation is the multiplication of X' by Y. To use the strategy outlined above for the singular value decomposition (SVD) calculations related to DBPLS, we adopted the so-called power algorithm which is iterative in nature (Golub, GH and Van Loan, C F 1989). The operations involved at each of the iterations are only matrix×vector, vector×matrix, and vector×scalar which are all separable onto the sub-matrices.

The MATLAB code for SVD calculation using power algorithm in comparison to MATLAB routine svds.m is given in the Appendix. Note both the example power algorithm code and svds.m need the whole matrix to be in memory. In implementing power algorithm in our PLS analysis, all the matrix by vector, vector by scalar multiplications are done by reading in one sub-matrix a time.

C.1.2 Efficient DBPLS Implementation Via Matrix Size Reduction

Assume the data matrix X is n by $P_X(X_{n \times P_X})$ with n<<Px and rank(X)≤n. Without losing generality, we assume rank (X)=n. The row space of X is with an orthornorm basis, $e=(e_1^T\ e_2^T\ \ldots\ e_n^T)^T$ each as a row vector satisfying: $e_i e_j = \{^{1,\ i=j}_{0,\ i \neq j}$.

This basis, for example, can be the one via principal component analysis on the matrix X. Note that there are infinite many such bases. X can be expressed as $X=X_1 e$ where $X_1$ is a full-rank n×n matrix.

Similarly, $Y=Y_1 f$ with $f=(f_1^T\ f_2^T,\ \ldots\ f_n^T)^T$ being orthornorm basis of the space spanned by the rows of Y. Thus, $X^T Y = e^T X_1^T Y_1 f$. On the other hand, SVD gives $X^T Y = USV^T$ $X_1^T Y_1 = U_1 S_1 V_1^T$, where U, V, $U_1$ and $V_1$ are, in general, unitary matrices. Thus, we have $USV^T = e^T U_1 S_1 V_1^T f$ Motivated by this derivations, we implemented the calculation of $X_1$, $Y_1$, and svd of $X_1^T Y_1$ (i.e., the calculation of $U_1$, $S_1$ and $V_1$). Then we used matrix e or f to transform the solutions back to the space of the original matrices X and Y. Theoretically, however, we are not claiming that the first n diagonal elements of S equal the n diagonal elements of $S_1$ and we are not claiming that there exists an equal relationship between the first n columns of U with the first n columns of $e^T U_1$ or between the first n rows of V and the first n rows of $V_1^T f$.

In any case, we will further explore these relationships described here (see research plan below) and seek the possibilities to take the advantages of the efficient computing for the reduced matrices (as initial value for the iterative power algorithm, for example).

C.2. Assessment of Statistical Significance and Reliabilities

C.2.1. Jacknife Procedure

Experimental design permitting, the leave-one-out procedure is an economic way to empirically validate our inter-network analysis strategy using available data. The Jacknife cross-validation procedure could be an efficient way to demonstrate the latent variable pair as powerful discriminators (in discriminate analysis in C.3) or indices of longitudinal decline (in power analysis).

C.2.2. Bootstrap

Bootstrap resampling technique can be used to estimate the voxel-wise standard errors of the singular images (for imaging data) or the element-wise standard error of the vector w and c in general. The singular image can be scaled by voxel-wise standard error for statistical significance assessment.

C.3. Preliminary Empirical Validation and Application

C.3.1 Subjects and Imaging data

To empirically validate the proposed DBPLS method for examining the functional/structural linkage between FDG-PET and MRI datasets in this preliminary study, FDG-PET/MRI data from 15 young adults (31.3±4.8 years old) and 14 elder adults (70.7±3.5 years old) were used. All of them are participants of our on-going longitudinal study of Apolipoprotein ε4 (APOE-ε4), a generic risk factor of Alzheimer disease, and all are non-carriers of APOE-ε4 (i.e., they have 0 copies of APOE-ε4 alleles). Subjects agreed that they would not be given information about their apolipoprotein E genotype, provided their informed consent, and were studied under guidelines approved by human-subjects committees at Good Samaritan Regional Medical Center (Phoenix, Ariz.) and the Mayo Clinic (Rochester, Minn.).

The subjects denied having impairment in memory or other cognitive skills did not satisfy criteria for a current psychiatric disorder and did not use centrally acting medications for at least two weeks before their PET/MRI session. All had a normal neurological examination. Investigators who were unaware of the subjects' APOE-ε4 type obtained data from medical and family histories, a neurological examination, and a structured psychiatric interview. All of the subjects completed the Folstein modified Mini-Mental State Examination (MMSE) and the Hamilton Depression Rating Scale and all but one subject completed a battery of neuropsychological tests.

PET was performed with the 951/31 ECAT scanner (Siemens, Knoxville, Tenn.), a 20-minute transmission scan, the intravenous injection of 10 mCi of 18F-fluorodeoxyglucose, and a 60-min dynamic sequence of emission scans as the subjects, who had fasted for at least 4 hours, lay quietly in a darkened room with their eyes closed and directed forward. PET images were reconstructed using the back projection with Hanning filter of 0.40 cycle per pixel and measured attenuation correction, resulting 31 slices with in-plane resolution of about 8.5 mm, full width at half maximum (FWHM) and axial resolution of 5.0-7.1 mm FWHM, 3.375 slice thickness and 10.4 cm axial field of view. The rate of glucose metabolism (milligrams per minute per 100 g of tissue) was calculated with the use of an image-derived input function, plasma glucose levels, and a graphic method (Chen, K. et al. 1998). Glucose metabolism in the whole brain was calculated in each subject as the average measurement from all intracerebral voxels (including those of ventricles) inferior to a horizontal slice through the mid-thalamus.

MRI data was acquired using a 1.5 T Signa system (General Electric, Milwaukee, Wis.) and T1 weighted, three-dimensional pulse sequence (radio-frequency-spoiled gradient recall acquisition in the steady state (SPGR), repetition time=33 msec, echo time=5 msec, $\alpha$=300, number of excitations=1, field of view=24 cm, imaging matrix=256 by 192, slice thickness=1.5 mm, scan time=13:36 min). The MRI data set consisted of 124 contiguous horizontal slices with in-plane voxel dimension of 0.94 by 1.25 mm.

The example data set was analyzed by PLS having two group subjects pooled together (group membership information is not used in the analysis). We also refer this group membership blind PLS analysis as agnostic PLS C.3.2 Data Pre-Processing Image pre-processing was performed using the computer package SPM99 (http://www.fil.ion.ucl.ac.uk/spm, Wellcome Department of Cognitive Neurology, London). Improved procedure for optimal MRI segmentation and normalization was used to discount the effect of non-brain tissue in generating gray tissue probability map for each subject on the MNI template space (created by Montreal Neurological Institute). Briefly, this optimal procedure first segments the MRI data on each subject's brain space, masks the segmented gray tissue map with careful reviewing the mask first to eliminate any non-brain part. Then, the procedure estimates the deformation parameters comparing the masked gray matter map to the one on the MNI template coordinate space, and subsequently deforms the raw MRI data which was then segmented to create the gray matter map on the MNI template space. Both modulated and un-modulated gray matter maps were created. The gray tissue maps were also re-sampled to 26 slices (thickness of 4 mm), each slice is a matrix with 65 by 87 voxels of 2 mm. Finally, a common mask was created containing only those voxels whose gray matter intensity values is 0.2 or higher on all subjects. PET data was also deformed to the MNI template space with the same voxel size and slice thickness. The same 20% common mask was applied to the PET data as well. Finally, PET and MRI data were smoothed respectively to make their final resolutions compatible.

C.3.3 Preliminary Results

The PLS algorithm was implemented using MATLAB (MathWorks, MA) on an IBM A31 laptop running linux operating system.

First, the accuracy and reliability of the sub-matrix based Power algorithm was tested against the MATLAB SVD implementation (svd.m and svds.m) using randomly generated matrix of varying sizes (100 by 100 up to 6500 by 6500). It was found that the implementation of power algorithm was equivalent to its MATLAB counterpart. However, for a computer with 1 GB RAM and 1 GB swap space, MATLAB svds.m crashed for a matrix of a moderately large size (6500 by 6500), speaking for the need to divide huge matrices into smaller ones.

For the example MRI/PET datasets, each row of the matrix X was formed by arranging the voxels of one subject's brain into a row vector. Thus, the number of rows in matrix X is the number of subjects and the number of columns is the number voxels in the brain mask.

When no attempt was made to first reduce the matrix size, the computing of the first singular image pair and the associated singular value took about 70 hours after some code optimization.

Figure 2A:
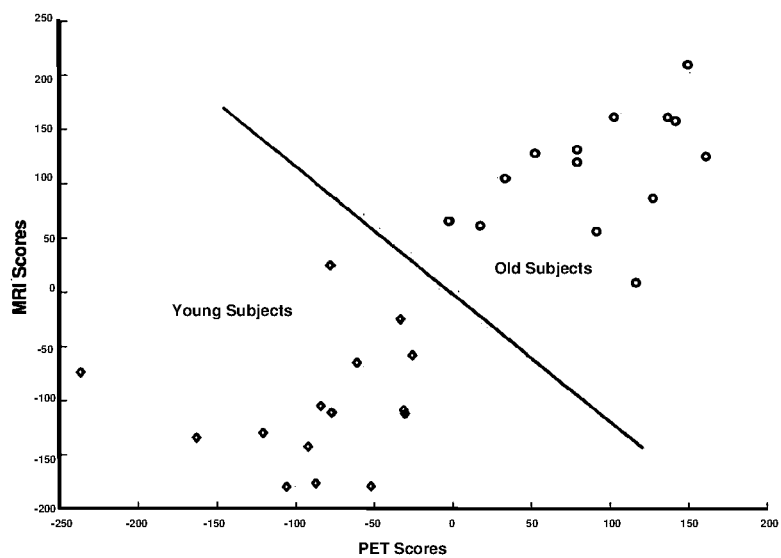
FIG. 2A illustrates the use of Partial List Squares (PLS) to discriminate 14 from 15 young subjects in a preliminary PLS validation study, where the x-axis is the PET-PLS subject scores, and the y-axis is the MRI-PLS subject scores.

Not surprisingly, it was found that the PET-PLS subject scores and the MRI-PLS subject scores are closed correlated (R=0.84, p<7.17e-09). More interestingly, as shown in FIG. 2A, there is a total separation between the young and old subject group (open circles: old subjects; closed circles: young subjects).

Figure 2B:
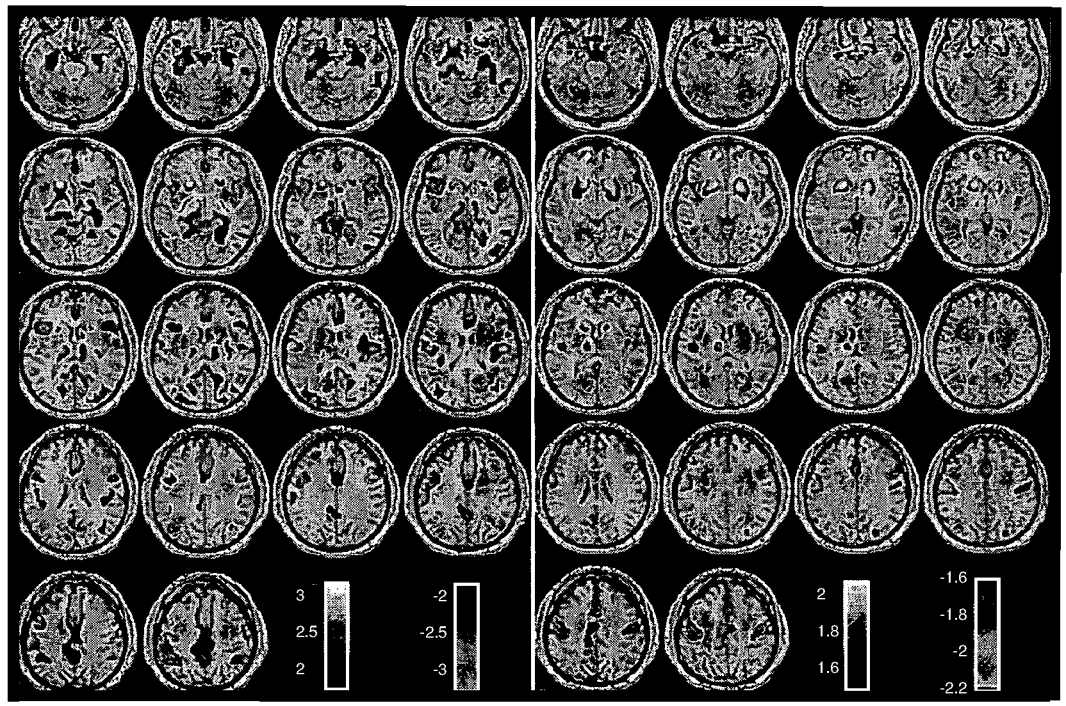
FIG. 2B shows the first singular images for PET on the left panel and for MRI on the right panel for the same preliminary PLS validation study.
Figure 4:
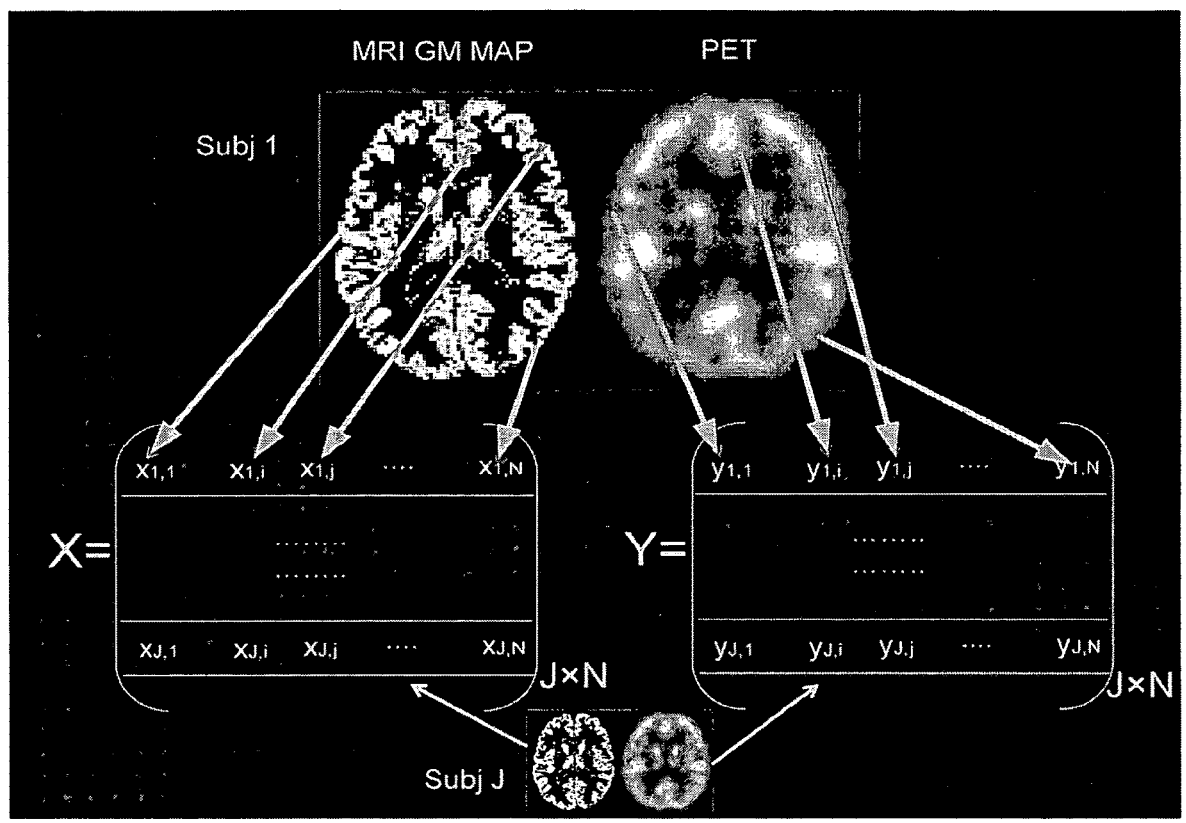
FIG. 4 demonstrate a procedure to form matrix X and Y for J human subjects' dual FDG-PET and MRI data, where each row of X/Y is for one subject's MRI/PET data rearranged as a row vector.
Figure 5:
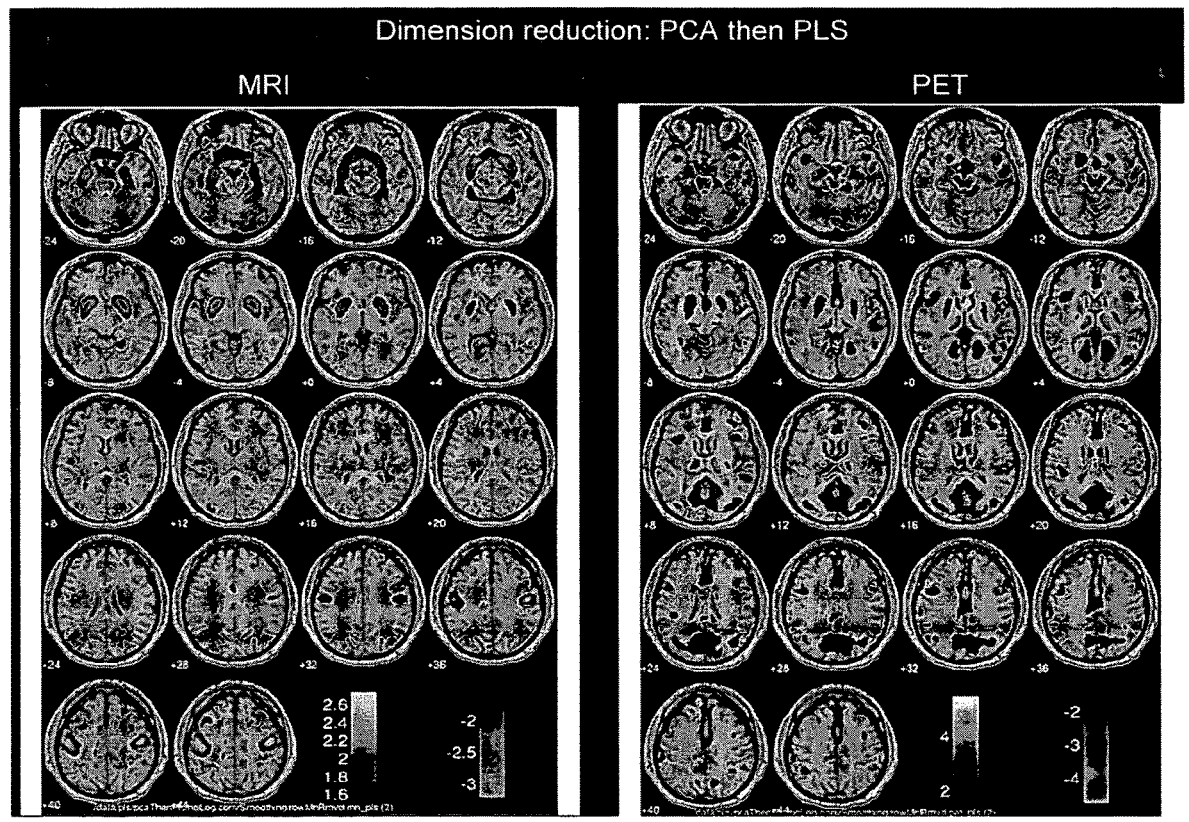
FIG. 5 shows the singular images (MRI on the right panel and PET on the left panel) generated by first applying data dimension reduction technique (PCA) followed by PLS procedure, where it can be noted that there is a striking similarity between the PLS with a power algorithm and the present one.

The first singular images for PET and MRI, as shown in FIG. 2B (left panel PET, right panel: MRI), were created with an arbitrary threshold of p=0.05 to both positive and negative values of the singular images after normalization by the bootstrap estimated standard error (p=0.05 is justified as there is no need for multiple comparisons). Realizing that the signs of the singular images are relative and that the interpretation of the PLS results is an unfamiliar territory, our current bio-physiological understanding of the dual-patterns is as follows: The combined pattern indicated consistent lower gray matter concentrations and lower cerebral metabolic rate for glucose (CMRgl) occurred concurrently in medial frontal, anterior cingulate, bilateral superior frontal and precuneus regions; posterior cingulate and bilateral inferior frontal regions were only seen (with negative pattern weights) on the PET but not on the MRI; some white matter regions, caudate substructure, and occipital regions were shown to be concurrently preserved or on the gray matter distribution along. These cross-sectional young and old group MRI/PET findings indicate that, in very healthy adults, age group difference is associated with regionally distributed and interlinked dual network patterns of brain gray matter concentration and CMRgl changes, as measured with MRI voxel-based morphometry and FDG-PET.

It is also worth to compare the PLS results against the SPM findings. SPM was performed contrasting the young and old subject groups separately for the PET dataset and the MRI gray matter dataset (voxel-based morphometry analysis). We found overall pattern similarities between the PLS singular images and the SPM T-score maps as well as multiple apparent focused differences. In contrast to SPM, however, inter-network PLS combines information from both modalities and provides a global index (pair) for which can be used as a powerful discriminator. For example, the multiple comparison corrected global maxima of the PET or MRI is significant at p=0.005 (corrected), the PET/MRI PLS latent variable is p<2.32e-18 contrasting young and old subjects without the need to correct multiple comparisons.

The matrix size reduction technique improved the computing speed significantly. In fact, the PLS took less than a minute to finish, with one time overhead effort (in couple of hours) to construct the orthonorm basis, e and f, respectively for X and Y. We found striking similarities PLS results with or without reducing the matrix sizes first. However, differences existed between these two approaches both in terms of the spatial patterns of the singular images and in terms of the latent variable numerical values and empirical distributions.

The differences were also evident when we performed Jacknife analysis. Our purpose of the Jacknife analysis is to examine the accuracy of classifying the subject who was left out at each of 29 runs. A linear classifier was determined first in each run based on the information of the remaining 28 subjects. The classification is to assign the left-out subject to young or old group based on his/her PET and MRI latent variable numerical values against the classifier. 100% accuracy was obtained for the PLS procedure without the matrix size reduction performed. With the matrix size reduction, 3 of 29 subjects were misclassified (89.7% accuracy).

C4. Finding Summary of Preliminary Studies

The findings and their implications of our preliminary study can be summarized as:

(1) Iterative Power algorithm is numerically identical to MATLAB svd routine (2) Though computationally expensive, the PLS is still feasible without matrix size reduced for research settings
(3) The combination of structural and functional imaging data increased sensitivity
(4) The inter-network PLS results are in general consistent with the univariate SPM findings but with more increased statistical power
(5) PLS latent variables could be construction parts for global index for detecting changes, for distinguishing group differences, or for classifications,
(6) There exists potential possibility to improve the computing speed
(7) Non-parametric statistical testing and validation procedure are integrated parts of the PLS implementation.

D. Experimental Design & Methods

D.1: Data

No need for any new data to be acquired under this proposal. Our plan is to use data acquired under the supports of various existing grants or that to be started. Our use of human subjects' data will be strictly obedient by the HIPPA regulation and any requirements from local/institutional IRB.

D.1.1 MRI, FDG-PET Data from Our NIH Sponsored Longitudinal APOE-ε4 Study

With over more than 160 healthy subjects followed longitudinally (some of them have 5 or more visits already), this NIH sponsored project (NIMH MH057899-06), on which Dr. Chen and Dr. Alexander are listed as investigators, Dr. Reiman as PI and Dr. Caselli as co-PI, is unprecedented in many aspects. It will be our first choice of our PLS applications especially with our specific aim of developing a prediction scheme and constructing a clinical diagnostic scheme based on cross sectional and longitudinal FDG-PET and MRI data (to a limited extent, as the data are all from normal subjects. See D.1.3). Thus, both cross sectional and longitudinal datasets will be considered. Moreover, with our implementation of MBPLS and the availability of the neuropsychological (NP) data, PLS application to triple datasets (MRI, PET and NP data) will be on the top of our priority list. The conventional MBPLS application will be aimed for the AD diagnosis, prediction of disease onset or conversion to MCI and treatment evaluation. In addition, the MBPLS with the newly proposed object function will be used to look for inter-linkage among the imaging and non-imaging datasets.

The patient recruitment procedure, MRI/PET imaging data acquisition procedure, neuropsychological measurements, and the IRB regulations (requirement of consent form etc.) are the same or almost identical as the ones described in the preliminary study section.

D.1.2 MRI, FDG-PET Data from Our Alzheimer Association Sponsored APOE-ε4 Study

The preliminary study described in this grant application is actually based on the data from this Alzheimer Association sponsored study. As such, description of the data can be found in the 'Preliminary Studies' section. Again, Dr. Chen and Dr. Alexander are listed as investigators, Dr. Reiman as PI and Dr. Caselli as co-PI.

D.1.3 MRI, FDG-PET Data of AD Patients, MCI Patients and Healthy Subjects Under ADNI The Alzheimer disease neuroimaging initiative (ADNI) is one of the largest projects sponsored by NIH in its history. Dr. Chen, Dr. Alexander and Dr. Caselli are investigator and Dr. Reiman is co-PI on this project which started in the early part of 2005. The PI is Dr. Michael Weiner of UCSF. As many as 800 subjects will be recruited for their participation over two-year interval. Longitudinal MRI data will be obtained for all 800 subjects and half of them will be having FDG-PET as well. Since this project involves AD patients, MCI patients and normal subjects, we will be able to evaluate the use of PLS to characterize the normal aging, the disease progress, and the conversion to MCI and to AD. More importantly, we have more opportunities of developing a prediction scheme and constructing a clinical diagnostic scheme based on cross sectional and longitudinal FDG-PET and MRI data.

D.1.5 PLS Analysis on Non-Imaging Data with or without Neuroimaging Data

We will actively explore the possibility of applying our multi-modality inter-network PLS approach in and out the neuroimaging field. Microarray data from genomics study will be made available through our connection at the Translational Genomics Institute at Phoenix. The PLS application to genomic data will be with and without available neuroimaging data. The multi-dataset PLS analysis of genomic, neuroimaging data (FDG-PET and MRI) and neuropsychological measurements will be performed after analyzing, by Dr. Papassotiropoulos, blood samples from a subset of the participants of our longitudinal APOE-ε4 study to obtain their genomic information which are being planed and supported by other sources.

D.1.6 Optimized Data Pre-Processing

In the preliminary findings section, we introduced some pre-processing steps for the FDG-PET and MRI data. The pre-processing procedure will be studied further especially with in mind that datasets of other types could be part of the PLS analysis. The pre-processing steps that are of common interest to many analyses, such as spatial normalization, smoothing, some issues related to voxel-based morphometry (VBM) etc., will not be the focuses of the current investigation. (We are keenly aware of the debates on VBM, and confident that the new developments implemented in the new version of SPM5 will address that to a satisfaction. Advances on these areas will be followed closely and adopted in our pre-processing steps. Pre-processing steps that are more specific to PLS (or multivariate analysis in general) will be investigated, and their effects evaluated, carefully. Data standardization, for example, was traditionally performed by removing the mean and unitizing the standard deviation. We will consider various ways of incorporating the whole brain measurement into this standardization, such as proportional scaling or analysis of variance (ANOVA). This conventional standardization will also be reviewed for the longitudinal study for the use of baseline average vs. averages at followup times. Other pre-processing issues we will investigate include the assumption of multiplicative modulation of the global on regional measurements (like the one of SSM (Alexander, G. E and moeller, J 1994)) for some or all datasets and the use of baseline data as a priori for followup gray tissue segmentation.

D.2 DBPLS and MBPLS Implementation and Validation

D.2.1 MBPLS Implementation

Our previous PLS implementation focused on only DBPLS. Extensive efforts will be made for voxel-based MBPLS. On a voxel-by-voxel basis, we will first attempt to have the well-established MBPLS algorithm programmed for neuroimaging datasets also taking the presence of non-imaging dataset(s) into considerations. Subsequent validation, non-parametric statistical procedure and its use for real data analysis will follow as described elsewhere in this proposal.

In the methodological development session (see below), we propose to investigate the linkage among multi-datasets without designating one as dependent datablock and the rest as independent (predictor) datablocks. The methodological and theoretical investigation will be accompanied with its implementation first on personal desktop computers. In fact, the test code implementation and evaluation will be an important part of the methodological development. Once (and only after) its mathematical appropriateness and feasibility are fully understood, efforts will be devoted to make it available on the super compute system. Also, completion of the package will be marked as its flexibility of dealing with voxel-based, ROI-based imaging data or non-imaging data in general (see below).

D.2.2 Voxel-Based and ROI Based Implementations

Our current implementation of DBPLS is voxel-based. Though no extra efforts are needed in the computing part for the ROI based data as long as the data are fed to the program in proper format, it is not a trivial task to have a set of ROI chosen which are appropriate for brain functions in general, or designated only to specific brain diseases such as AD. With our primary AD research interest, a list of brain regions affected by AD will be generated based on our own research (Alexander, G. E. et al. 2002) and others (Minoshima, S. et al. 1995; Ibanez, V. et al. 1998; Silverman, D. et al. 2001). These brain regions will be carefully delimitated on the high resolution MRI template in the MNI coordinate space. The reliability of the ROI definition procedure will be examined (intra- and inter-raters test-retest) if some of the ROI need to be manually defined (for this purpose, we plan to use computer package MRIcro by Chris Rorden [www.mricro.com]). We also plan to transform these ROIs over to our customized template (for AD patients or for healthy subjects) using automated template-based ROI generation procedure (Hammers, A. et al. 2002). Published, widely used and well-documented ROI procedure as well as the results (e.g., the up to 200 ROIs that have been carefully defined by UCLA researchers in their efforts to automate the clinical diagnosis of AD) will be actively searched and utilized to minimize our own efforts.

D.2.3 PLS Validation

In the preliminary findings section, we reported the consistency of our PET/MRI PLS findings with SPM analysis results of PET and MRI separately. We plan to validate further our multi-modality inter-network PLS approach in contrasting its results to the results of univariate analysis for individual dataset (such as by SPM). The consistency between inter-modality PLS and intra-modality univariate analysis validated indirectly the PLS approach. More importantly, the increased sensitivity by multi-dataset PLS, as found in our preliminary study, is demonstrated the expected power. The contrast between PLS and the univariate analysis, with the insights to biomedical and biophysiological processes, will also be helpful in understanding and interpreting the PLS results.

Another important aspect of PLS validation is the reproducibility of the uncovered inter-network patterns (singular images) and the latent variable pairs. Though Jacknife leave-one-out procedure is a sound cross-validation in this regard, repeating the analysis of the same biological nature on imaging data acquired from a different group of subjects would be more assuring. The reproducibility study of this kind will be performed for various studies including the young/old subject study reported in the preliminary findings section as data from more subjects are being acquired with the support of our longitudinal APOE-ε4 project and others. (Note the number of subjects in each group prevented us from doing so in our preliminary study). Whenever permitting, subjects will be divided for two identical analyses for validating reproducibility. Exactly like establishing an index for monitoring disease progress or diagnosing disease onset, the group split will be repeated to the maximum number possible to increase the validation efficiency in terms of the use of the data available and programming efforts will be made so the validation can be updated when new data are added to our database.

D.3 Establishment of MBPLS/DMPLS as an Integrated Surrogate Marker for Treatment Evaluation and Disease Progress for AD We will devote a significant effort in developing the multi-modality inter-network PLS as a scheme which can be used in assessing longitudinal changes with or without intervention and in describing disease progressing especially for AD. For treatment evaluation, it is now well recognized that the use of neuroimaging surrogate marker is associated with much increased statistical power, reduced cost, and shortened study duration. More importantly, neuroimaging technique allows the treatment/prevention effects to be observed at the early stage of the interested disease or even before its onset as demonstrated in our APOE-ε4 study. For AD disease progress or the brain alternations before clinical symptoms (Reiman, E. M. et al. 1996; Reiman, E. M. et al. 2001; Reiman, Chen, Alexander, Caselli, Bandy, Osborne, Saunders, and Hardy 2004), it is now more and more common to acquire multi-modality imaging and non-imaging data. On the other hand, the richness of the neuroimaging data has not been used optimally. The lack of full use of neuroimaging data is reflected by the fact that univariate statistics is the dominant analytical tool for almost all neuroimaging studies evaluating the effects of a treatment or disease progress. In other words, a number of selected brain regions or a global index is often used for statistical power calculation, for disease progress monitoring and for clinical diagnosis (often without correcting multiple comparisons).

As a complement to the univariate approach, we propose and attempt to establish intra- and inter-modality multivariate indices as an analytical tool in studying treatment effects, in monitoring disease progress, and potentially in diagnosing AD disease (using cross-sectional as well as longitudinal data). The proposed approach will enable a researcher to use the richness of the neuroimaging data to the fullest. Consequently, increased statistical powers, reduced type-I errors and improved sensitivity and specificity are expected. On the other hand, the approach should not be too complicated and counter-intuitive.

We propose to investigate the inter-network PLS feasibility as a surrogate marker following the procedures described below. Note that the basic idea discussed here are applicable to both single-modality and multi-modality datasets.

D.3.1 Longitudinal PLS Analysis

As our preliminary findings were cross-sectional, we will briefly describe several approaches of dealing with longitudinal data here. A) If the longitudinal data are only for two time points (baseline and followup), then the subtraction image could be created and entered into the inter-network PLS analysis after taking care of variation in the time intervals and in the whole brain measurements; B) data at different time points can be treated as separated datablocks and enter them all into the analysis directly. In doing this, we will need to investigate means to have the longitudinal information incorporated; C) PLS can be performed separately for data from each time point followed by the examinations of changes in latent variable and in singular images using conventional statistical tools; D) Results from univariate analysis (such as SPM) can be the starting point of further PLS analysis. For example, longitudinal voxel-wise regression coefficients (the slope, e.g.,) can be subjected to further PLS analysis (cross patient groups, e.g.). We will focus on A) and D) first in our proposed study. Note the next subsection is with in mind the discussion of this part.

D.3.2 Index Establishment.

An index, or a set of indices, is a measure of longitudinal changes with or without treatments. In the simple univariate index case, the CMRgl decline (the difference between the baseline and followup scans) for a given brain location is such an ideal index. The effects of an evaluated treatment are reflected as a measurable reduction of the decline. The decline without the treatment and the decline reduction with treatment together with their variation are usually the starting point for the determination of the number of subjects needed in a new trial with a desired statistical power.

First, potential candidates for such as an index or a set of indices could be the latent variable pair(s) following the same logic thinking in the well established statistical power procedure, but also taking the inter-voxel covariance and inter-network covariance into considerations. With the directionality of the latent variable made consistent with longitudinal decline (sign of the latent variable and the weights is relative, and will not affect the linkage assessment), for example, the first latent variable pair can be combined to form a single index or can be used as a bivariate indices to enter into power calculation (note the maximum covariance does not imply maximal correlation). Since the latent variables themselves summarize both intra-modality and inter-modality linkages, the power calculated is not based on selecting a few voxel/ROI locations and ignoring the relationship among them and with the rest of the brain. The same idea can be applied to the use of up to 2nd, 3rd or more latent variable pairs, or an optimal combination of them, which is optimally pre-determined in correlating to clinical outcomes, for example.

Secondly, the singular-image within each dataset (the weights w in the first dataset, for example) can be used to construct indices for subsequent statistical power or disease progress analysis. This is possible because of the availability of the bootstrap estimated variance for each weight (at each voxel). Again, with the establishment of the weight directionality (positive or negative) consistent with the univariate voxel-wise CMRgl decline, a collection of the singular-image voxels where the weight are of significance (p<0.005, e.g.,) can be chosen. Note the selection of the voxel can also be guided with the results of the voxel-based analysis.

Third and finally, the directional singular-image differences between AD patients and MCI patient (AD research as our major application area of the current methodology proposal) can be utilized together with the Bootstrap approach estimated voxel-wise variances. Like the individual voxel CMRgl decline and the decline reduction in univariate power analysis for a single-modality PET study, the pattern/network differences and their hypothesized reductions (either universal or brain region dependent) could be foundation for determining the number of subjects for desired powers or the powers for given number of subjects for a multi-modality study (dual FDG-PET and MRI, for example) or basis for reporting disease progress/severity.

D.3.3 Power Calculations

Power analysis can be performed for each of the latent variable pairs separately and followed by the combined power (defined as the probability observing at least one of these effects). This combination procedure is partially justified as the latent variable pairs are uncorrelated and are assumed Gaussian, therefore independent. For the chosen voxels over the singular-image (selected significant node-points over the spatial pattern) or itself, we propose to use Monte-Carlo simulation procedure for the type-I error and statistical power calculation since no available software, to our knowledge, exists for such purpose (see B, Appendix for our own preliminary work presented in the annual nuclear medicine meeting, 2004). Using the first latent variable pair in a dual-dataset study as an example, our current primitive thinking of the simulation procedure is provided below.

The Monte-Carlo simulation package is based on the computer package SPM99. The simulation starts with a 3D brain mask (provided by the researcher) over a standard or customized brain space (e.g., MNI template space). Thus, spatial normalization, image alignments, etc. processings are not part of the simulation process. For each of N iterations (N=10000, for example), this Monte-Carlo simulation procedure consists of the following steps: (1) For the type-I error calculation, a 3D brain image of either of the two modalities for each of M subjects is generated as Gaussian random numbers on a voxel-by-voxel basis. The image is then smoothed according to the final image resolution of the analysis. For statistical power calculation, the map generation procedure is identical as above but with the averaged images of the approximations by up to nth eigen-images for all M subjects (linear regression approximation, similar to approximation of the original image by the first several PCA components). The voxel-wise variance and inter-voxel covariance estimated by Bootstrap will be incorporated as the following. Assume E is the covariance matrix within the eigen-image voxels that are significant. This huge matrix is rank deficient due to the fact that the number of voxels (variables) is most likely far more than the number of observations (the number of Bootstrap resamplings). Thus, square matrix $\Omega$ exists such that $\Sigma=Q'\Lambda Q$, where $Q'Q=QQ'=I$ and $\Lambda$ is diagonal with only the first rank($\Sigma$) non-zero elements. Thus, one can quickly generate random vector x of length rank($\Sigma$) with mean zero and covariance matrix $\Lambda$, and random $y=Q'x+a$ will have covariance matrix $\Sigma$, where a is the voxel-by-voxel mean. For power calculation purpose, the covariance matrix can be replaced by correlation matrix so the final y is of unit variance and the mean of $$\frac{a}{\sqrt{diag(\Sigma)}}$$

(effect size). In addition to dealing with the inter-voxel correlations, it is important also to note that the added effects assume that the Gaussian variable is with unit standard deviation. The smoothing process, however, reduced the standard deviation to sub-unity levels. Thus, the original known effect sizes, relative to the smoothed random field, are much larger. Consequently, the statistical power could be significantly over-estimated. To correct the over-estimation of the power, each smoothed Gaussian random field is scaled by its new cross-voxel standard deviation priori to the introduction of the non-zero effect sizes.

(2) The threshold of a given type-I error (5%, e.g.,) can be assessed by (2D) histogram constructed over the N simulations/realizations (2D corresponds to two imaging datasets). The type I error (the significance level) is estimated as the ratio of n over N, where n is the occurrences of the hypothesized event (without effect of interest introduced).

Among several potential alternatives, the threshold of the type-I error, T, can be calculated over the 2D histogram as prob($\sqrt{x^2+y^2} \leq T$)=1−α where α is the type-I error and x and y are the first latent variable pair. T is then used for the power calculation. Apparently, the closeness of singular-image based on the simulated M subjects' data to the true one (or the one from analyzing the real data) should be examined as a part of this study (see reproducibility part in this Research Plan). Other alternatives exist and will be probed further.

D.3.4 Inter-Network PLS Based Disease Progress and Clinical Diagnosis

Independent to the power analysis, the use of the inter-network PLS for examining disease progress and clinical diagnosis should be based on and confirmed with well-established criterion historically and on on-going basis. To illustrate, we will use our NIH sponsored longitudinal APOE-ε4 study as an example. With more and more healthy subjects in our longitudinal APOE-ε4 study converted to AD or MCI, our first attempt will be to establish such criterion using MBPLS with the conversion rate as the dependent block and FDG-PET, MRI as independent blocks. This criterion establishment will be based on a subset of the subjects. The rest will be used for validation purpose. To increase the validation efficiency in terms of the use of the data available, the group split will be repeated to the maximum number possible. Programming efforts will be made so the validation can be updated when new data are added to our database. This procedure also lays the foundation for the use of MBPLS as a predictor on the onset of disease.

D.3.5 Relative Importance of a Datablock in Terms of Statistical Power and in Terms of Clinical Diagnosis We will use the normalized block score as a measure of the datablock importance. Though it is not methodologically challenging, the relative importance in contributing to the diagnosis is of significance of both biologically and financially. New indices of datablock importance will also be looked into proper to the research questions raised.

D.4 Methodological Developments

D.4.1 New Object Function for MBPLS

The calculation of conventional MBPLS is based on distinguishing the datasets as a single dependent dataset and one or more independent (predictor) dataset(s). This setting is ideal if the focus is to predict the performance of the dependent block from the independent blocks (such as for disease progress and clinical diagnosis). However, when there is no clear dependent-independent distinction among the datasets (FDG-PET, PIB-PET and structural MRI from a group of AD patients, e.g.,), or when one's primary interest is to seek the inter-relationship among all datasets, a new approach is needed. There are numerous intuitive ways to setup criterion in terms of defining the inter-dataset covariance. The challenge is to find the ones that are mathematically and logically justified, scientifically meaningful and computationally feasible. We will list a few such criterions here to motivate ourselves and others. In the followings, assume there are c datasets, $X_1, X_2, \ldots, X_c$. $t_k$ is a latent variable representing $X_k$ (k=1, 2, ..., c), $t_k = \Sigma w_i^{(k)} x_i^{(k)}$ where $x_i^{(k)}$ is the ith column of matrix $X_k$ and $w_i^{(k)}$ is the corresponding weights (of unit norm). The following object functions can be defined for the calculation of the latent variables: A) $\max(\min_{k<l}(\text{cov}(t_k, t_l))$, B)

$$\max\left(\prod_{k<l} \text{cov}(t_k, t_l)\right).$$

Notice that the covariance used in these expressions is unconditional (the effects of other datasets are ignored when calculating $\text{cov}(t_k, t_l)$). More complicated schemes will be needed for the object function which uses the conditional covariance instead. We will need to investigate the existence, uniqueness, convergence, and speed of convergence of the solution for the optimization procedure using the above defined object functions or others. Moreover, proper iterative procedure needs to be established for uncovering the second, third, etc. latent variable sets taking care of the effects of previous latent variable sets and orthogonality issue. Section C of the Appendix provides some preliminary results on our alternative MBPLS investigation effort. We demonstrated the uniqueness and existence of the alternative MBPLS solution with some additional constrains.

D.4.2 DBPLS Calculation with and without Matrix Size Reduction

Our previous results given earlier showed DBPLS results differences and similarities between directly calculating the latent variable using iterative Power scheme and reducing the matrix size to their ranks first. Further theoretical examinations and theory-guided computer simulations are needed to unveil the causes of the differences/similarities and to develop procedures, when feasible, to account for the differences. The improved computational speed associated with the reduction of the matrix size is important for the proposed non-parametric statistical resampling procedures as they in general are iterative in nature. The bootstrap procedure can be performed in conjunction with the matrix size reduction technique to estimate the standard deviation of the weight at each voxel location for each image modality. The robustness of the estimated standard deviation in regards to this dataset size reduction technique will be investigated.

D.4.3 Explore Alternatives in Addition to PLS Approach or Based on PLS Results

Though the primary focus of this proposal is to establish DBPLS and MBPLS as a tool for the study of inter-network linkage and a way to combine information from multi-datasets, we realize that there are other approaches to describe various aspects of the relationship among multi-datasets and to maximize the power combining information from each dataset. We view the establishment of MBPLS and DBPLS as 1) one of many tools that will be used to investigate the multi-datasets systematically (i.e., as inter-network approach), and 2) an explorative tool for further applying other methodologies either data-driven, model-based, or hypothesis driven. These methodologies are well established for intra-modality single dataset study with a track record of successful applications. However, they may need to be further generalized for inter-modality, multi-dataset studies. The two methodologies we are interested for such generalization are (inter-datasets) independent component analysis (ICA), and (dual-dataset) structural equation modeling (SEM). At this very early stage, our description here will be only sketchy and conceptual in the context of our future research direction.

Multi-datasets ICA: We will only illustrate the concepts for the dual-dataset case. For the conventional single-dataset, one way to obtain the ICA solution is the minimization of mutual information (Hyvarinen, A. et al. 2001). With the same notations as above, the first inter-dataset independent pair t and u is obtained by minimizing the mutual information between t and u:

$$\min\{H(t)+H(u)-H([tu])\}$$

where $H(x) = \int p(x) \log p(x) dx$ is the entropy for continuous random variable/vector x, and p(x) is the probability density function (pdf) of x. Integration will be replaced by summation for discrete random variable/vector. Note this is not a full procedure by which all independent component pairs are obtained. A conceptually intuitive numerical approach for putting constrains on the mixing matrix in generating the dual-dataset ICA solution is being investigated by our group. Other alternatives are also being investigated but will not be discussed here.

Multi-Datasets SEM:

Results from either voxel-based PLS or ROI-based PLS will provide researchers the covarying pattern within each imaging modality dataset and the linkage among these datasets. These pattern and linkage information can be further understood with the construction of a proper quantitative (mathematical) model such as SEM. The generalization of the well-known SEM to the case of inter-datasets seems natural and straightforward at first. However, one needs to find a way to distinguish and summarize the link strengths between nodes within one datasets and those across multi-datasets.

We again emphasize our current research focus is the inter-dataset PLS. The discussion of these additional techniques (inter-network ICA and inter-network SEM) will serve us as reminder that the development of inter-network PLS is only a start of methodological investigation of the multi-dataset analytical strategy.

D.5 Feasibility Testing of the Proposed Methodologies

Understandably, the proposed procedure is relatively expensive in comparison to the univariate analysis and to the intra-modality multivariate network analysis. However, our previous findings suggested it is feasible computationally to perform DBPLS on dual-imaging dataset even without reducing the matrix size first as an analysis procedure for basic research settings. It is also important to know that number of subjects will only affect the computation time marginally with the calculation of the covariance matrix at the very beginning and the subject scores at the very end. Thus, the reported computation time in our previous findings is of representative for a wide range of numbers of subjects/scans. In the context of computational feasibility, it is worth to note that conventional MBPLS as a clinical diagnostic tool or a marker for treatment evaluation is computationally efficient as its dependent datablock is with single or limited number variable(s). Thus the size of the covariance matrix is not a concern.

We are not satisfied at all with the current computation speed. As can be seen throughout this Research Plan, a major effort is to efficiently implement the algorithm. Computational feasibility testing will be an integrated part in each and every step of the implementation. Like in our preliminary study, this feasibility testing includes the following three parts: (1) algorithm is correct, mathematically sound. The implemented algorithm will be examined carefully against mathematical derivations and compared to well-established computer package that can handle only non-imaging data with sizes that are much smaller than that of neuroimaging datasets. The comparison will use computer simulated datasets of moderate sizes; (2) algorithm is computationally efficient. Each part of the algorithm will be optimized (vectorize all possible operation in MATLAB, e.g.). That optimization will be tested against the dataset with expected sizes in real study (for example, number of voxels). The data sets can be either from real study or via computer simulation; (3) the output of the algorithm is scientifically interpretable. This is exactly the same as D.2.4 PLS validation. See that part for details.

The three-step feasibility testing outlined above will be at each step of each algorithm planned for investigation. This is especially true for the newly proposed methodology development (such as the alternative MBPLS object function described in D.4.1).

OTHER EXAMPLES

Figure 7:
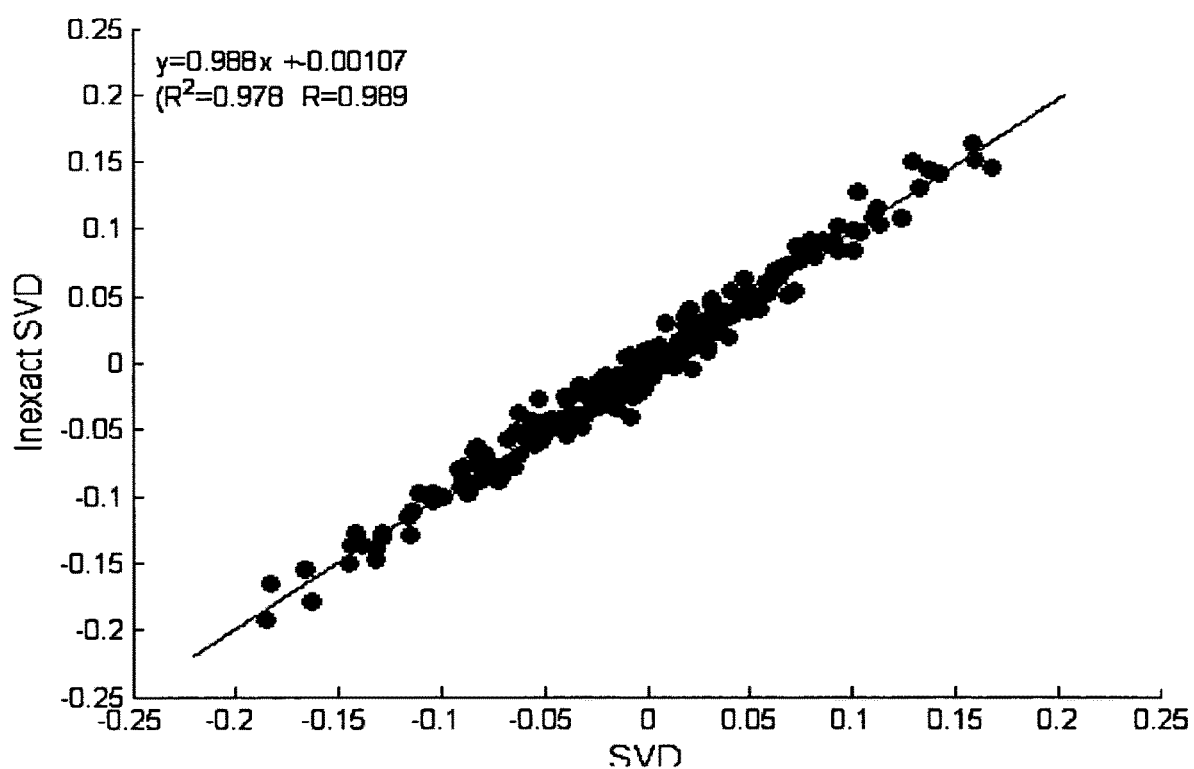
FIG. 7 shows the close result SVD relationship calculated by the exact SVD computation procedure which is with high computational costs and by the proposed method which uses dimension reduction technique first (inexact), where the inexact SVD results is shown on the Y axis, and the exact SVD is shown on the X axis.

FIG. 7 is a graph that depicts a comparison between an exact agnostic PLS operation and the inexact agnostic PLS operation. The graph sets forth eigenvectors of a 29 by 200 random matrix. For this eigenvector, the x-axis is the exact agnostic PLS operation and the y-axis is the inexact agnostic PLS operation.

Figure 6:
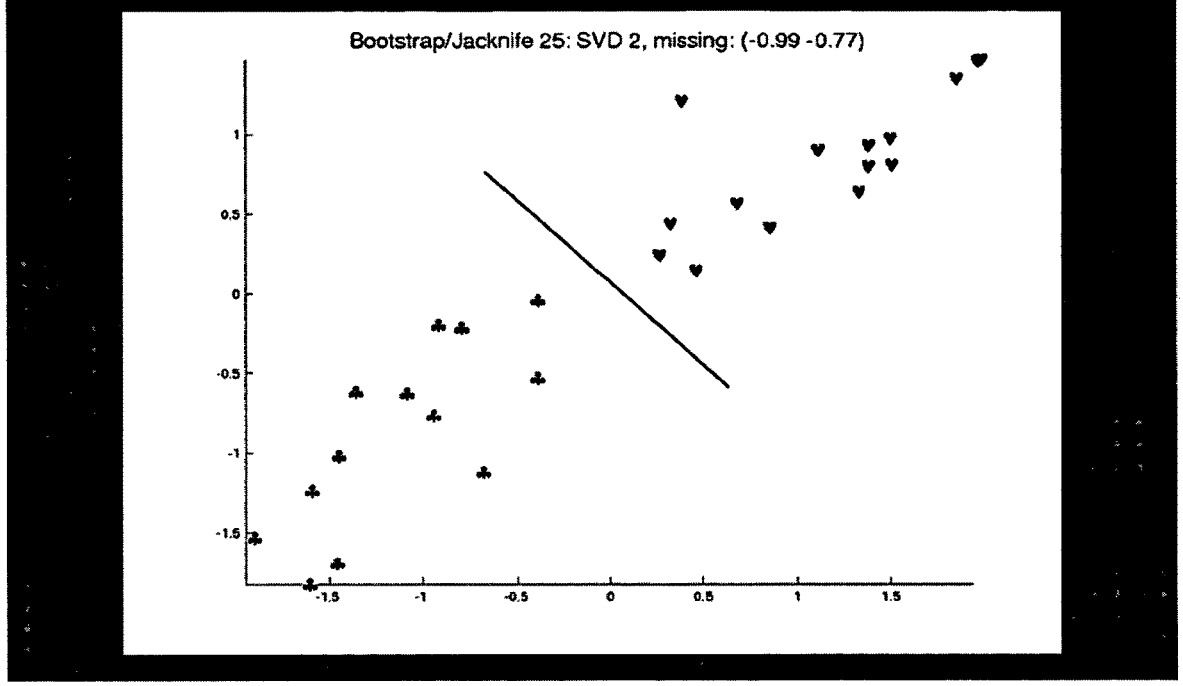
FIG. 6 depicts the use of the PLS derived subject scores as a discriminator in a jackknife procedure which excludes one subject at a time, and then predicts the membership of the subject using the information from the remaining subjects.
Figure 8A:
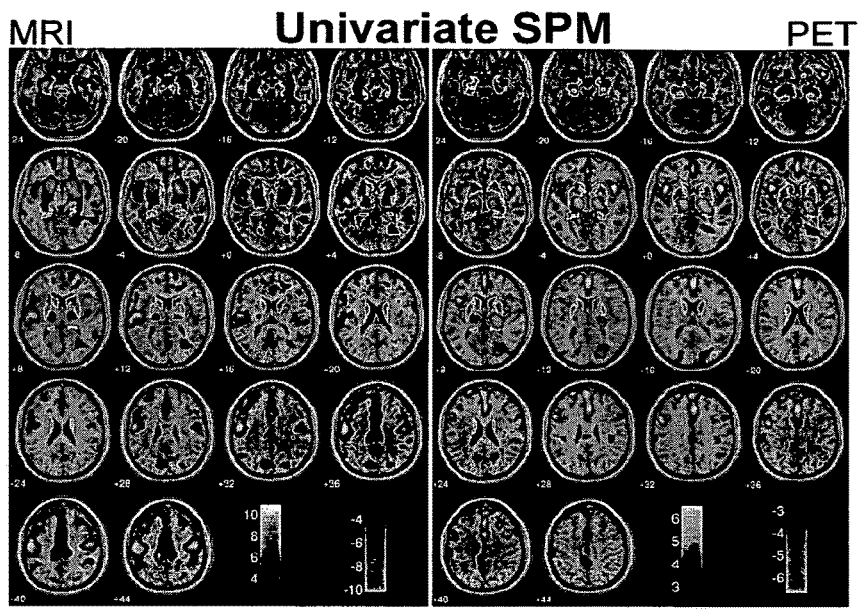
FIG. 8A shows respective MRI and PET univariate SPM findings (T-map) in the preliminary human brain studies, where the results were obtained via SPM voxel-wise univariate analysis (PET and MRI separately), and though with increased power, the PLS results are compatible with these SPM findings.
Figure 8B:
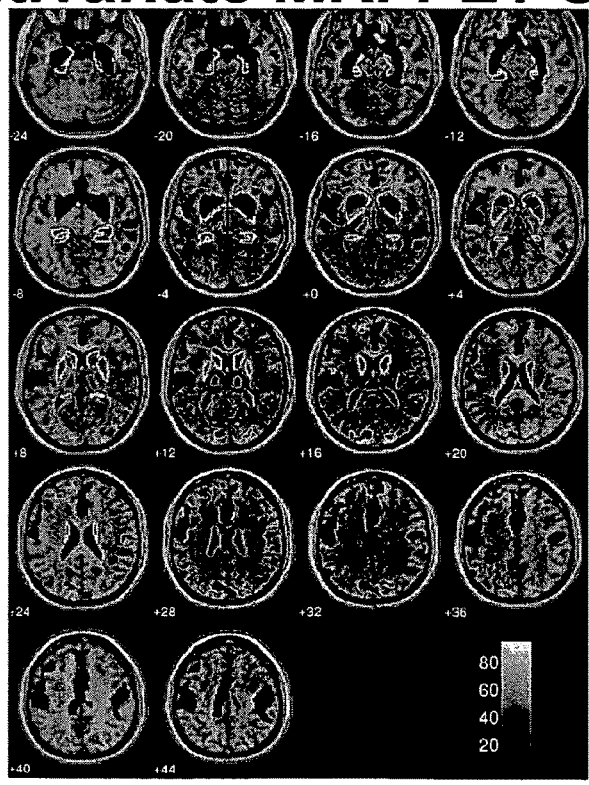
FIG. 8B shows SPM dual-variate findings (F-map) in the preliminary human brain studies, where the results were obtained via SPM voxel-wise multivariate (in this case, each voxel has two variables), and though with increased power, the PLS results are compatible with these SPM findings.

Spatial patterns are shown that were uncovered by inter-modality exact agnostic PLS operations seen in FIG. 2B, by the inexact agnostic PLS operation seen in FIG. 6A, by the standard univariate SPM procedure seen in FIG. 8A, and by the voxel-by-voxel multivariate MRI-PET SPM seen in FIG. 8B. Other than the voxel-wise multivariate SPM seen in FIG. 8B, MRI and PET findings are displayed on the left and on the right respectively.

Motivated by the availability of the multi-neuroimaging datasets and encouraged especially by the success of the single-modality PLS approach, we propose to extend the use of PLS for analyzing dual-imaging datasets. We hypothesize that this inter-modality PLS can seek for the maximal and direct linkage among multi-datasets or optimally combine information from them for increased statistical powers.

More specifically, 1), we explore the use of PLS both agnostically and non-agnostically strategies to analyze dual-modality neuroimaging data. Agnostic PLS is to seek direct linkage between two image-datasets blinded with any subject group membership or scan conditions and to perform subsequent analysis relevant to the condition/group differences. Non-agnostic PLS, on the other hand, is to consider the group/condition differences directly in combining the information from dual-imaging datasets. 2), we propose a computationally feasible approach for the agnostic PLS to overcome the difficulty associated with the huge size of the covariance matrix between two neuroimaging datasets. 3), we put forward an implementation alternative to first reduce the covariance matrix size to improve the computational speed of the agnostic PLS. 4), we will lay out the framework of performing non-parametric inference or cross-validation procedures respectively for agnostic and non-agnostic PLS. Finally, 5), we empirically validate this inter-network PLS approach by applying it to dual MRI/PET datasets from well separated young and old healthy subject group and contrasting the findings in the context of the univariate SPM analysis, and intra-modality PLS approach (i.e., using only one of the two imaging dataset to seek the group/condition differences).

Methods

Subjects and Data

To empirically validate PLS for examining the functional/structural linkage between FDG-PET and MRI datasets, FDG-PET/MRI data from 15 young adults (31.3±4.8 years old) and 14 elder adults (70.7±3.5 years old) were used. All of them are participants of the 'PET, APOE and aging in the Preclinical Course of AD' study supported by the Alzheimer's Association. All are APOE-ε4 non-carriers. Subjects agreed that they would not be given information about their apolipoprotein E genotype, provided their informed consent, and were studied under guidelines approved by human-subjects committees at Banner Good Samaritan Regional Medical Center (Phoenix, Ariz.) and the Mayo Clinic (Scottsdale, Ariz.).

The subjects denied having impairment in memory or other cognitive skills, did not satisfy criteria for a current psychiatric disorder, and did not use centrally acting medications for at least six weeks before their PET/MRI session. All had a normal neurological examination. Investigators who were unaware of the subjects' APOE-ε4 type obtained data from medical and family histories, a neurological examination, and a structured psychiatric interview. All of the subjects completed the Folstein modified Mini-Mental State Examination (MMSE) and the Hamilton Depression Rating Scale and all but one subject completed a battery of neuropsychological tests.

PET was performed with the 951/31 ECAT scanner (Siemens, Knoxville, Tenn.), a 20-minute transmission scan, the intravenous injection of 10 mCi of $^{18}$F-fluorodeoxyglucose, and a 60-min dynamic sequence of emission scans as the subjects, who had fasted for at least 4 hours, lay quietly in a darkened room with their eyes closed and directed forward. PET images were reconstructed using the back projection with Hanning filter of 0.40 cycle per pixel and measured attenuation correction, resulting in 31 slices with in-plane resolution of about 8.5 mm, full width at half maximum (FWHM) and axial resolution of 5.0-7.1 mm FWHM, 3.375 slice thickness and 10.4 cm axial field of view. The rate of glucose metabolism was calculated with the use of an image-derived input function, plasma glucose levels, and a graphic method (Chen et al. 1998). Glucose metabolism in the whole brain was calculated in each subject as the average measurement from all intracerebral voxels (including those of ventricles) inferior to a horizontal slice through the mid-thalamus.

MRI data was acquired using a 1.5 T Signa system (General Electric, Milwaukee, Wis.) and T1 weighted, three-dimensional pulse sequence (radio-frequency-spoiled gradient recall acquisition in the steady state (SPGR), repetition time=33 msec, echo time=5 msec, α=30°, number of excitations=1, field of view=24 cm, imaging matrix=256 by 192, slice thickness=1.5 mm, scan time=13:36 min). The MRI data set consisted of 124 contiguous horizontal slices with in-plane voxel dimension of 0.94 by 1.25 mm.

Data Pre-Processing

SPM99, a software package designed for the analysis of brain imaging data sequences, was used for image pre-processing. The optimal MRI segmentation and normalization procedure (Good et al. 2001) was used to discount the effect of non-brain tissue in generating a gray tissue probability map for each subject on the MNI template space (created by Montreal Neurological Institute). Both modulated and un-modulated gray matter maps were created. The gray tissue maps were also re-sampled to 26 slices (thickness of 4 mm), each slice a matrix with 65 by 87 voxels of 2 mm. Finally, a common mask was created containing only those voxels whose gray matter intensity values is 0.2 or higher on all subjects. PET data was also deformed to the MNI template space with the same voxel size and slice thickness. The same brain mask was applied to the PET data as well. Finally, PET and MRI data were smoothed respectively to make their final resolutions compatible (final full width at half maximum is 15 mm for both smoothed MRI and PET).

PLS with Deflation

We adopted the one that deflates data matrices by projecting information onto the previous latent variable pairs. This guarantees the orthogonality of the extracted component in all data spaces (Hoegaerts et al. 2003). The PLS procedure with deflation scheme is described below.

PLS uncovers the maximal covariance among a pair of latent variables, linearly constructed respectively from each of the two datasets. Starting from original data matrices X and Y (with standardization necessary), the first latent variable pair is constructed as follows: The latent variable of X is $t=\Sigma w_i x_i$ where $w_i$ is a scalar for random variable $x_i$ which is the $i^{th}$ column of X (i=1, 2, . . . ). In matrix form, t=Xw where $w=(w_1, w_2, \ldots)^T$ with $\|w\|=1$. For imaging dataset, index i refers to the $i^{th}$ voxel in the brain volume. Similarly, the Y latent variable can be expressed as u=Yc ($\|c\|=1$). Again, we refer to t and u as the first latent variable pair. In the context of agnostic PLS, we refer to w and c as (the first) singular image of X and Y respectively as w and c can be mapped back to image space and displayed. The covariance of the two latent variables, t and u, is therefore cov(t,u)= w'X'Yc (assuming zero mean). The maximal covariance value with respect to w and c can be proven to be the square root of the largest eigenvalue of the matrix Ω=[X'YY'X] with w being the corresponding eigenvector of Q, and c being the corresponding eigenvector of Y'XX'Y The second latent variable pair can be constructed in a similar way after the contributions of the first latent variable are regressed out (deflated) from X and Y as follow: Express $$p_1 = \frac{X't}{\|t\|^2}, q_1 = \frac{Y'u}{\|u\|^2}, r_1 = \frac{Y't}{\|t\|^2}$$

and calculate new $X_1$ and $Y_1$ as $X_1=X-tp_1'$, $Y_1=Y-tr_1'$. The same procedure will then be repeated for the new X and $Y_1$ matrix pair to construct the second latent variable pair. The third and remaining latent variable pairs will be calculated similarly (up to the $L^{th}$ pair, where L=rank(X)). Note that the deflation scheme described here is a reflection of the fact that Y is designated as the dependent datablock and X as the independent datablock.

Multi-Block PLS

The PLS introduced so far is referred to as dual-PLS (DPLS for dual datasets) and is for our agnostic PLS especially when both X and Y are imaging data. When one is interested in the relationship between a dependent block, Y and more than one independent block, $X_1, X_2, \ldots, X_m$, multi-block PLS (MPLS) is needed. As will be seen, our non-agnostic PLS is actually MPLS in nature. The main difference between the DPLS and MPLS appears when one attempts to uncover the latent variables 2 and up. To start, MPLS uncovers the first latent variable between Y and $X=[X_1 X_2 \ldots X_m]$ exactly the same way as DPLS. The DPLS deflation step described above, however, will mix contributions from various X blocks and makes the result interpretation difficult. Various deflation schemes were proposed. Following the suggestion by (Westerhuis and Smilde 2001), we only deflate Y-block while keeping X-blocks untouched.

Agnostic PLS Versus Non-Agnostic PLS

In performing non-agnostic PLS, the young and old group membership is the matrix Y as our main interest is the difference between these two groups. In this case, Y is actually a column vector with value 1 and 2 for young and old subject respectively. Alternatively, one could also form Y with individual subjects' age. The X block is formed by pooling PET and MRI data together, X=[PET MRI], where PET is $n \times P_x$ data matrix formed from the PET-FDG data. n is equal to the number of subjects and $P_x$ is the number of brain voxels over the brain mask. The data matrix MRI is defined similarly. We referred this as non-agnostic PLS as this MPLS procedure directly uses group membership as the dependent block. Apparently, type-I error assessment coming out directly from this non-agnostic PLS cannot be trusted, and additional procedure is needed to seek the true type-I error (see below).

The agnostic PLS, in contrast, seeks the directly linkage between the dual image datasets, PET and MRI, without referring to the old/young subject differences. Should the difference between the old and young subject be the primary source of variation, the agnostic PLS uncovered maximal covariance will have the power to distinguish the two groups naturally and without too much concern about the type-I error associated with the examination of the group differences (but see Bootstrap and jacknife procedures below).

Agnostic PLS Implementation Via Iterative Power Algorithm: Exact Method

It is obvious that the size of the square matrix $\Omega$ is the number of voxels within the brain volume (assuming the same number of voxels for both imaging datasets). To make the computation possible, we partitioned matrix $\Omega$ and others into a series of small matrices which are only read in, one at a time, into the computer memory when needed. To make this strategy work, the only allowed matrix operations are those that can act on sub-matrices and result in sub-matrix form. An operation of this kind is the matrix multiplication, for example. To use the strategy for the singular value decomposition (SVD) related to PLS calculation, we adopted the so-called power algorithm which is iterative in nature (Golub and Van Loan 1989) (see appendix A for an illustrative piece of MATLAB codes). The operations involved at each of the iterations are only matrix x vector, vector x matrix, and vector x scalar which are all separable onto the sub-matrices.

Agnostic PLS Implementation Via Matrix Size Reduction: Inexact Method

Assume the data matrix X is n by $P_x(X_{n \times P_x})$ with $n \ll P_x$ and $rank(X) \leq n$. Without losing generality, we assume rank $(X)=n$. The row space of X is with an orthonormal basis, $e = (e_1^T e_2^T \ldots e_n^T)^T$ satisfying $e_i e_j = \{0, i \neq j}^{1, i=j}$. This basis, for example, can be the one via PCA on the matrix X (Note that there are an infinite number of such bases). X can be expressed as $X = X_1 e$ where $X_1$ is a full-rank n×n matrix. Similarly, we have $Y = Y_1 f$. Thus, $$X^T Y = e^T X_1^T Y_1 f \quad (1)$$

The singular value decomposition (SVD) of $X^T Y = USV^T$ and $X_1^T Y_1 = U_1 S_1 V_1^T$. In these expressions, the U and $U_1$ are column-wise orthogonal, and V and $V_1$ are orthogonal matrices. Equation (2) above can be re-written as $$USV^T = e^T U_1 S_1 V_1^T f \quad (2)$$

Motivated by (2), we perform SVD on $X_1^T Y_1$ (i.e., the calculation of $U_1$, $S_1$ and $V_1$) instead of $X^T Y$. We then used matrix e and f to transform the solutions back to the space of the original matrices X and Y.

Though this approach is obviously inexact, our interest is to examine how its results are compared to the exact approach (we are only interested in the first n non-zero singular values and the associated columns of U and V anyway).

PET-MRI Linkage Indices Related to Agnostic PLS

Since the agnostic PLS seeks directly the covarying patterns between the dual-image datasets, various scalar and images indices can be defined to examine the relationship between the structural MRI and functional PET. In this current writing, two of them will be introduced and used. The first is the squared correlation coefficient of the latent variable pair between the MRI dataset and the PET dataset. The second one is an image-wise index, referred to as the explanatory power. It is a correlation coefficient map one over the PET image space. For each PET voxel, the corresponding correlation coefficient is between the single latent variable of the X-block (MRI) and the PET measurement from this voxel.

Non-Parametric Statistical Procedure for Non-Agnostic PLS: Permutation

To assess the type-I error in testing the difference between the old and young subjects, 10000 row-wise random permutations were performed on matrix Y and the MPLS procedure was run for each of this permuted Y block and the unchanged X blocks. The histogram of unpaired t-test p-values over the 10000 runs is used to assess the type-I error. Only permutations that switch old/young group membership are counted toward the total number of permutations performed.

Non-Parametric Statistical Procedure for Agnostic PLS Analysis: Jacknife and Bootstrap Jacknife Cross-Validation:

Agnostic PLS analysis (both exact and inexact) was repeated 29 times taking one subject out each time. The resultant latent variable pair from the 28 subjects was used to construct a linear discriminator which was then applied to decide old/young group membership for the left-out subject. This procedure allowed us to assess the classification accuracy.

Bootstrap Assessment of Statistical Significance:

With all 29 subjects included for the agnostic PLS, Bootstrap resampling procedure was run 100 times to estimate the voxel-wise standard deviation of the singular images. The Bootstrap estimated standard deviation was then used to scale the singular image pair for statistical significance assessment.

PLS in Comparison with SPM

The PET and MRI dataset was each analyzed separately by univariate SPM contrasting the old and young subjects (for the MRI data, the analysis is essentially the optimized voxel-based morphometry). To be consistent with the PLS analysis, the global CMRgl and the total intracranial volume (TIV) was accounted for by proportional scaling and the mask for the PLS analysis (see pre-processing) was used in the SPM procedure. In addition to the univariate SPM, MRI gray matter maps and FDG-PET data were run under the SPM multivariate mode with F-statistics. i.e., PET and MRI measurements were treated as bi-variates at each voxel. In both SPM analyses, MRI and PET data from global maximal location(s) were extracted and used jointly to test the young and old group differences.

The dual PET/MRI datasets were analyzed by non-agnostic PLS and by agnostic PLS with or without first reducing the sizes of the matrices of X and Y. Again, the agnostic PLS analysis was conducted having the two group subjects pooled together (i.e., group membership information was not used in the PLS procedure. see Discussion section for more of our rational of practice of this kind). The latent variable pair of the agnostic PLS was used jointly to test the young and old group differences.

The spatial covarying patterns from the 5 analyses, univariate SPM, multi-variate SPM, non-agnostic PLS, agnostic PLS without matrix size reduction, and agnostic PLS with matrix size reduction, were compared. The differences and similarities in the uncovered spatial patterns were visually inspected. The spatial pattern is the single F-score map for the multivariate SPM and the two t-score maps (one for FDG-PET and the other for MRI gray matter VBM) for univariate SPM respectively. The spatial patterns are the singular image pair for the agnostic PLS and the unmixed PET and MRI patterns separated out from the X-block for the non-agnostic PLS. The p-values assessing the difference between the old and young subjects were reported together for the agnostic PLS, SPM. The permutation results for non-agnostic PLS were reported and compared among three non-agnostic PLS analyses: X-block is PET only, X-block is MRI only, and X-block is both PET and MRI.

Results

Equivalence of Power Algorithm with MATLAB SVD:

The Power algorithm was implemented using MATLAB on an IBM A31 laptop running Linux operating system. The accuracy of the algorithm was tested against the MATLAB SVD implementation (svd.m and svds.m) using randomly generated matrices of varying sizes (100 by 100 up to 6500 by 6500). It was found that the implementation of power algorithm was equivalent to its MATLAB counterpart. However, for a computer with 1 GB RAM and 1 GB swap space, MATLAB svds.m crashed for a moderately large size matrix (6500 by 6500).

Numerical Similarities Between Agnostic Exact PLS and Inexact Agnostic PLS:

The inexact PLS implementation (i.e., with matrix size reduction first) was tested and compared to the exact solution again using randomly generated matrices of varying sizes. Though results by the two methods were not identical non-surprisingly, there existed consistent correlations between them. Illustrating this consistency using component 4 calculated from a randomly generated matrix pair with 29 as the number of subjects and 200 as the number of voxels, FIG. 7 shows a very strong correlation between the exact method (x-axis, the column 4 of the matrix U) and the inexact method (y-axis, the column 4 of $e^T U_1$). Over 100 simulated matrix pairs, however, the correlation coefficients fluctuated between 0.73 and 0.99. It was also found that the first component was poorly correlated when both matrices X and Y are non-negative (e.g., uniformly distributed random univariate taking values over the interval [0 1]). In processing our real data, fortunately, both matrices were mean removed.

Individual SPM-PET, SPM-MRI Patterns and the Covarying PET/MRI Patterns of the Agnostic PLS:

The different analytical techniques were first compared by visually inspecting the changes, uncovered by each of them and shown in FIGS. 2A, 6A, and 8A-8B, over the brain volume. FIGS. 2A, 6A, and 8A-8B are for exact and inexact agnostic PLS respectively. The left image on FIG. 8A is for SPM-MRI (VBM) and the right image on FIG. 8A is for SPM-PET. The voxelwise bi-variate SPM is on FIG. 8B. Though they are of distinguished nature (intra-modality and voxel-wise univariate or voxel-wise bi-variate vs. inter-modality and multivariate) and should be interpreted differently, overall they looked very similar to each other.

As an example, FIG. 2A displays agnostic PLS uncovered PET and MRI covariance patterns superimposed on the standard brain anatomical map (left panel MRI gray mater singular image, right panel: PET singular image). They were created with an threshold of p=0.05 to both positive and negative values of the singular images after normalization by the bootstrap estimated standard errors (100 runs). The combined pattern indicated consistent covarying lower gray matter concentrations and lower cerebral metabolic rate for glucose (CMRgl) occurred concurrently in medial frontal, anterior cingulate, bilateral superior frontal and precuneus regions; posterior cingulate and bilateral inferior frontal regions were only seen (with negative pattern weights) on the PET but not on the MRI; some white matter regions, caudate substructure, and occipital regions were shown to be concurrently preserved or on the gray matter distribution alone. These cross-sectional young and old group MRI/PET findings indicate that, in very healthy adults, age group difference is associated with regionally distributed and inter-linked dual network patterns of brain gray matter concentration and CMRgl changes. Unlike the individual SPM PET or SPM MRI/VBM analyses, inter-modality PLS quantified the linkage strength between the two datasets (optimized latent variable pair covariance).

Figure 9A:
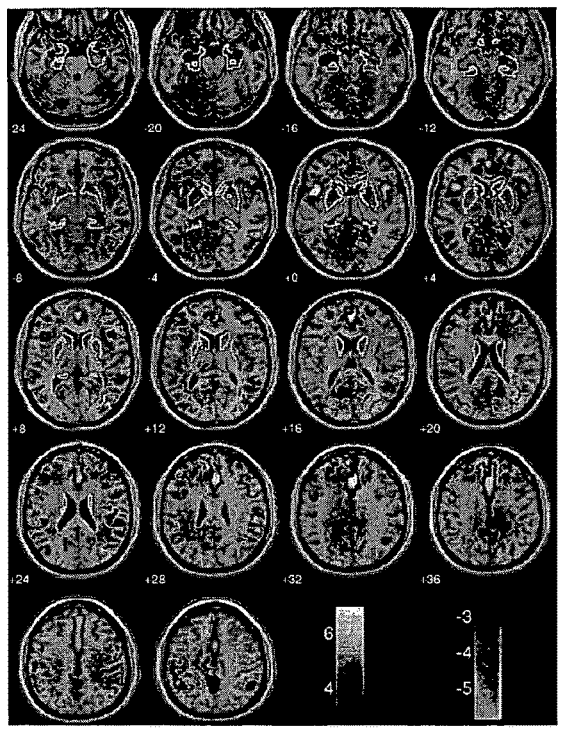
FIG. 9A shows the voxel-by-voxel PET correlation with the overall MRI PLS latent variable for the preliminary human brain study, where the latent variable is representative of the overall MRI data, and thus, the PET pattern displayed in this FIG. 9A reflects that PET voxel-by-voxel variations are related globally to the brain structure measures by MRI.
Figure 9B:
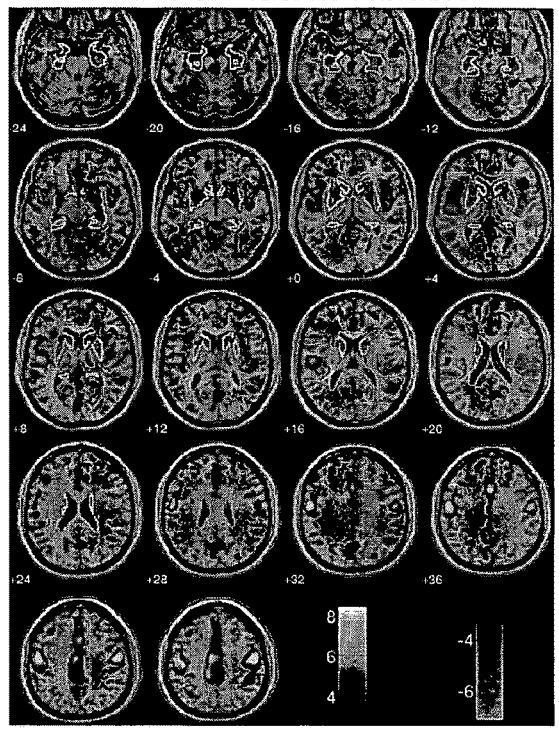
FIG. 9B shows the voxel-by-voxel MRI correlation with the overall PET PLS latent variable for the preliminary human brain study, where the latent variable is representative of the overall PET data, and thus, the MRI pattern displayed in this FIG. 9B reflects that MRI voxel-by-voxel variations are related globally to the brain functions measures by PET.

Linkage between FDG-PET and MRI gray matter concentration revealed by Agnostic PLS: The first overall linkage strength index is the squared correlation coefficient for the latent variable pair, t and u, which is found to be as strong as R2=0.73 (R=0.854 and p<3.77e-9) for the agnostic PLS. This close correlation is the basis for one to interpret the MRI and PET covarying spatial patterns and their interactions. For agnostic PLS, the overall explanatory power of X-block to each individual variable in Y-block was assessed by correlating the X-block latent variable t with y1, y2, y3, . . . in Y-block respectively. In our agnostic PLS in the current study where MRI was treated as X-block, the overall explanatory power is the overall anatomical influence on the FDG-PET spatial pattern (the map formed with correlation coefficients of the MRI gray tissue latent variable with the FDG-PET measurement voxel-by-voxel). This is shown in FIG. 9A as corresponding t-score map (testing if the correlation coefficient is significantly different from 0) with uncorrected p=0.001 threshold. In this map, the maximal positive correlation is in right middle cingulum at location (4 23 32), the correlation coefficient is 0.8 and p=1.97e-7 (T=6.917). The maximal negative correlation is in the left putamen at location (−20 20 −8) R=−0.751 and p=2.63e-6 (T=−5.918). Similarly, FIG. 9B shows the PET latent variable correlation with the voxel-wise MRI-gray tissue concentration. The maximal positive and negative correlation coefficients are 0.851 (p=4.92e-9, T=8.423) and −0.81 (p=9.96e-7, T=7.186) in right precentral at locations (50 −14 48) and right fusiform (34 −48 −4) separately. Note these two maps can be interpreted easily as correlation maps and are very similar to the singular images pair in FIG. 7.

In summary, FIGS. 9A-9B show spatial functional and structural correlation maps. Shown in FIG. 9A is the correlation map between the PET measurements from each brain voxel and the global MRI gray matter latent variable. Shown in FIG. 9B is the correlation map between the MRI measurements from each brain voxel and the global PET latent variable. The significance is p=0.001 uncorrected for multiple comparisons.

Figure 10:
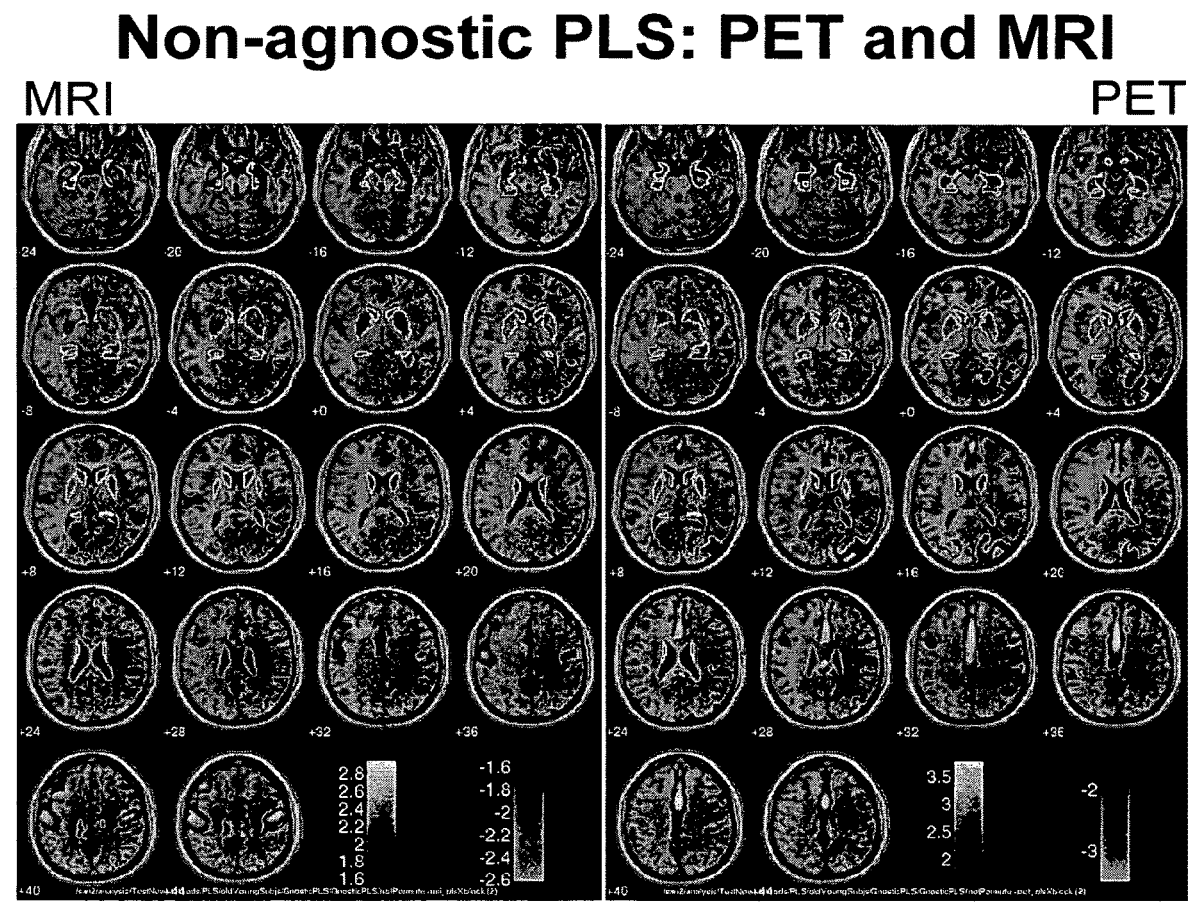

Patterns uncovered in the non-agnostic PLS with both PET and MRI data in the X-block: FIG. 10 shows the PET and MRI spatial distribution patterns that contributed significantly in distinguishing young and old subjects in non-agnostic PLS (i.e., the old young subject group membership is the MBPLS Y-block, and PET and MRI were both used in X-block as predictors). The overall similarities between the agnostic PLS singular images and the non-agnostic results are apparent. That striking similarities speak for the fact that the old young subject differences in our studies are overwhelming and the dominant variations.

Distinguishing old and young subjects by various methods I: Agnostic PLS in comparison with SPM In contrast to SPM, inter-network agnostic PLS combines information from both modalities and provides a more powerful (with smallest type-I error) global index. For example, the multiple comparison corrected type-I error for the global maxima is p=0.005 (local maxima at [48 14 −2] in right insula, uncorrected p=2.37e-7) for PET and p=0.00001 ([50 −18 52] right postcentral, uncorrected p=9.84e-12) for MRI separately. The multivariate (dual-variate in this study) SPM multiple-comparison corrected type-I error is 1.34e-7 (location [10 14 −14] right rectus, uncorrected p=1.06e-12). Note that univariate SPM-PET or SPM-VBM/MRI is one-tailed while that dual-variate SPM is two-tailed. In contrast, the significance is p=9.14e-11 and p=4.443e-12 for inexact and exact agnostic PLS respectively contrasting young and old subjects without the need to correct multiple comparisons (see FIG. 2A for exact agnostic PLS results).

In summary, FIG. 10 shows spatial functional and structural correlation maps with cocavying MRI maps on the left and PET maps of the right, where the patterns were generated by non-agnostic PLS operations, and FIG. 2A is a graph showing the result that the total old and young subjects are separated into respective group by using the latent variable pair obtained by an agnostic PLS operation.

As a further test for the power difference between exact and inexact agnostic PLS, the Jacknife analysis was used to examine the accuracy of classifying the subject who was left out at each of 29 runs. A linear classifier was determined first in each run based on the information of the remaining 28 subjects. The classification was to assign the left-out subject to the young or old group based on his/her PET and MRI latent variable numerical values against the classifier. 100% accuracy was obtained for the exact agnostic PLS procedure. For the inexact agnostic PLS, however, 3 of 29 subjects were misclassified (89.7% accuracy). This comparison is very preliminary as only linear discrimination was considered. Visual inspection of the data plot revealed the existence of a non-linear discriminator which has yet to be further investigated.

Distinguishing old and young subjects by various methods II: Comparison among Non-agnostic PLS with PET only, MRI only, or PET and MRI together. Since the old/young group membership was actually the Y-Block in non-agnostic PLS, and the latent variable of X is formed to best predict the membership, the resulted type-I error distinguishing the two groups has to be estimated using non-parametric permutation. Out the total 10000 random permutations with membership switched each time, two permutations generated group membership distinction as strong as the non-permuted one in non-agnostic PLS with PET alone (occurrence of type-I error=2). For the non-agnostic PLS with MRI alone, the number of type-I errors occurred 30 times. In contrast, the non-agnostic PLS with MRI and PET together serving as X-block, there is no additional occurrence of type-I error (except the non-permutated run). In other word, p=0.0003, 0.0031 or 0.0001 for running non-agnostic PLS with PET alone, MRI alone, or MRI and PET together.

Computational Speeds: Currently, the exact agnostic PLS computation, using the iterative Power algorithm, took about 15-46 hours depending on initial values used in the iteration and with some code optimization on an IBM A31 laptop (with 1 GB memory). See Discussion section for more on its practicality, our proposals and our on-going efforts that will significantly reduce the computation time.

For the inexact agnostic PLS and non-agnostic PLS, the computational speed is compatible to a routine SPM analysis.

Discussions

The use of PLS is proposed to investigate covarying patterns between multi-imaging datasets. With this technique, for example, researchers can seek the function and anatomy linkage information. In addition, it can be used to combine information from multi-dataset agnostically for non-agnostically for subsequent statistical inferences. PLS is one of several tools which can be potentially used for studying the inter-modality multi-imaging datasets. Not only can it be used to explore multi-datasets as a preliminary step for subsequent model based and hypothesis oriented analysis (see (Rajah and McIntosh 2005) for example as in intra-modality PLS), more importantly it can construct latent variable based index which can be used to evaluate group differences, longitudinal changes and potentially treatment effects.

Interpretation of the agnostic PLS covarying pattern of a given latent variable pair requires both the good grasp of the PLS theories and the bio-physiological aspect of the research questions. As a demonstrated in this study, the understanding of the agnostic PLS results can be helped from the individual univariate SPM findings. In any case, however, fundamental differences between intra-modality univariate SPM and multivariate inter-modality PLS should be noticed. Also, it is also worth noting that the covarying pattern was generated with the bootstrap estimated voxel-wise standard deviations as the normalization factors. The difficulty to interpret the dual covarying patterns is also associated with the fact that the PLS seeks the maximal covariances, cov(t,u)=w'X'Yc with respect to w and c (subject to $\|w\|=\|c\|=1$). Thus, the pattern c and w play similar role as the eigen-images of PCA-SSM which is with largest accumulated total variance for FDG-PET and MRI gray matter map respectively. Much more importantly, c and w established the association between the two datasets (via the correlation coefficient between the latent variable pair $t=\Sigma w_i x_i$ and $u=\Sigma c_i y_i$) and enabled the subsequent explanatory power analysis for further understanding of the relationship between the two datasets.

The PLS approach commonly used in the neuroimaging field is actually the dual-block PLS which is the one adopted in our agnostic inter-modality PLS. As seen in the method section, dual-block PLS is a special case, and more importantly, the foundation of the general multi-block PLS (MPLS) which can handle data from more than two data-blocks. Our non-agnostic PLS analysis in the current study in based on MPLS with the old/young group membership as the third (and dependent) dataset. With in mind the success of the multi-block PLS analysis in the field of chemometrics (Lopes et al. 2002; Westerhuis et al. 1996; Westerhuis et al. 1997; Westerhuis and Smilde 2001), more general use of MPLS in neuroimaging study will be the topic of future studies (such as to deal with triple imaging datasets with or without newly defined object function).

One limitation of the Power algorithm for the agnostic PLS is its relatively high computational expense due to the rate of convergence that also depends on the ratio between the first and the second largest eigenvalues (Press et al. 1992). Though efforts are undertaken in our lab to dramatically reduce the computation time as described below, routine agnostic PLS can be accomplished overnights with its current implementation (note the speed is affected mainly by the number of voxels, and only slightly by the number of subjects/scans). This is acceptable in basic research settings where demand for immediate result delivery is not as important as the issues of power or sensitivity which we believe the agnostic PLS is of advantageous as demonstrated by this study. Furthermore, the need to adjust settings and re-run the analysis is unlikely as all the pre-processing steps are standard and performed by SPM. In any event, we are continuously working on the efficient implementation of the inter-modality agnostic PLS. In fact, our initial investigation on the use of the inexact agnostic PLS solution as initial values for the Power algorithm iterative procedure demonstrate that the speed can be significantly improved for routine use. Moreover, other algorithms such as QR and Rayleigh quotient (Borga et al. 1997) with special consideration for implementation efficiency will be evaluated. Finally, we are in the process of evaluating the need to implement the agnostic PLS in a high performance computing system which is locally available to us.

MRI aging findings: Though there is not direct evidence on the hippocampus formation (HF) differences between young and old subjects, it had been reported that head-size adjusted HF volume is strongly associated with delayed memory performance (Golomb et al. 1994). Murphy et al., reported (Murphy et al. 1992) that the caudate and lenticular nuclei were significantly smaller in older than younger men. This significant difference remained when their volumes were expressed as a ratio of cerebral brain matter volume (Murphy et al. 1992). Decline in caudate nuclei, (but not in lenticular nuclei), in anterior diencephalic grey matter structures and association cortices and mesial temporal lobe structures, but no in lenticular nuclei, thalamus and the anterior cingulate were also reported in a separate study (Jernigan et al. 1991). Temporal cortex was found unrelated to aging process but posterior frontal lobe volume (DeCarli et al. 1994). Changes that are certain: ventricle enlargement, HF, caudate, and lenticular nuclei PET aging findings: Frontal metabolism measured with positron emission tomography is shown to be decreased relatively to that in other cortical or sub-cortical areas, in a population of healthy elderly compared to young volunteers (Salmon et al. 1991). Using visual qualitative assessment (Loessner et al. 1995), decreased cortical metabolism, particularly in the frontal lobes were found, but not in basal ganglia, hippocampal area, thalami, cerebellum, posterior cingulate gyrus and visual cortex. With partial volume effects corrected, Melter et al., found only true decline in regional cerebral blood flow in the orbito-frontal cortex (Meltzer et al. 2000).

To validate the newly introduced inter-modality PLS, the data from old and young subject groups with largest possible differences were used in this study. It is no surprising that all methods detected the group differences with statistical significance levels that many neuroimaging researchers desired to have in their studies. For hypothesis testing, it might be pointless to distinguish p=1.34e-7 and p=4.44e-12. In performing power analysis in planning a new study, on the other hand, these differences may translate to reduced costs or increased sensitivity. Moreover, with this first validation accomplished, it is our hope that PLS will be sensitive enough to pick up subtle group/condition differences which other methods might fail to detect.

In conclusion, the proposed inter-modality PLS method can be used to seek the direct linkage between two image datasets, and can be used to examine group differences with increased power.

Figure 11:
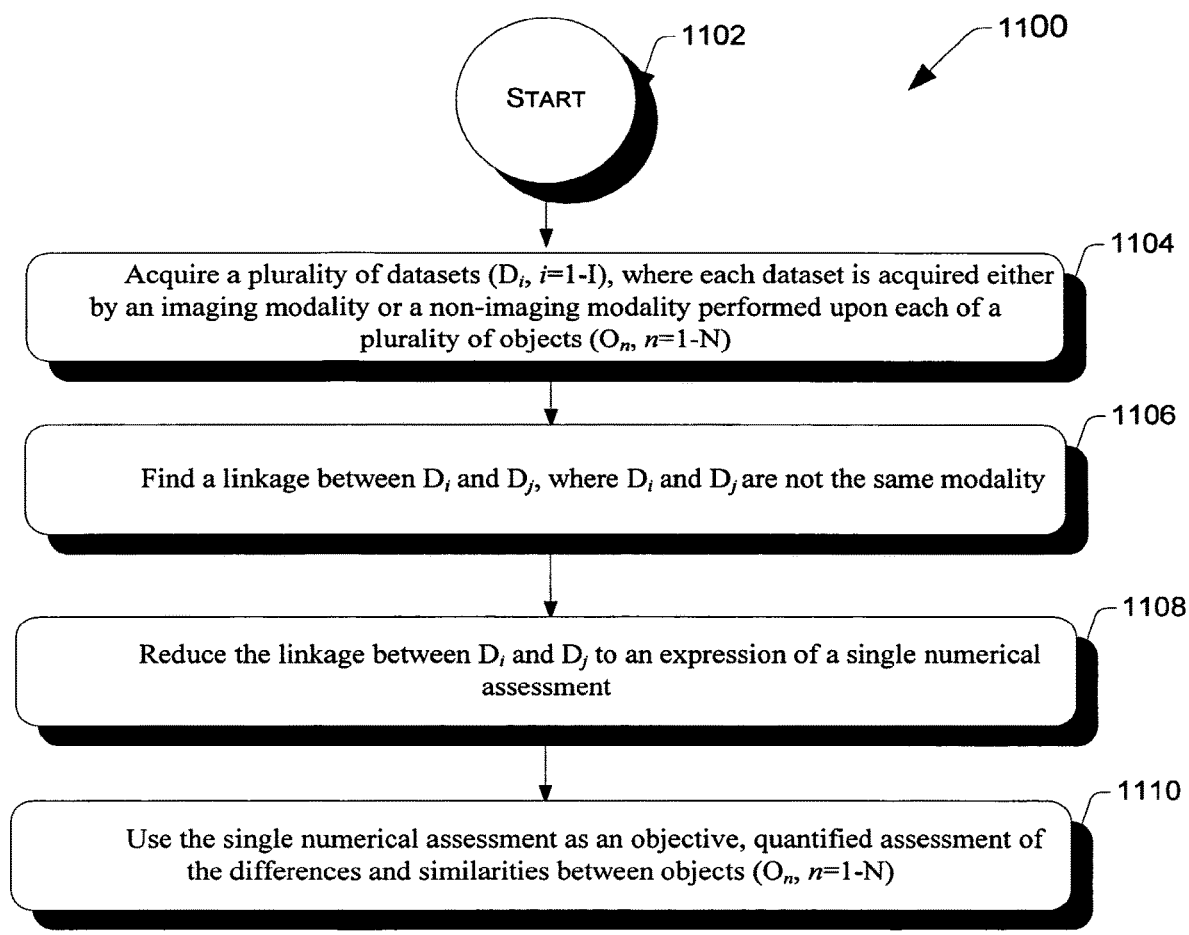
FIGS. 11-14 show respective exemplary processes for potential application of a proposed method.

FIG. 11 is a flowchart of an exemplary implementation of a process 1100 in which a link is made between datasets to accomplish a useful result. In step 1102, a plurality of datasets ($D_i$, i=1-I) are acquired. Each dataset is acquired either by an imaging modality or a non-imaging modality that are performed upon each of a plurality of objects ($O_n$, n=1-N). In step 1104, a linkage is found between $D_i$ and $D_j$, where $D_i$ and $D_j$ are not the same modality. In step 1106, the linkage between $D_i$ and $D_j$ is reduced to an expression of a single numerical assessment. In step 1108, the single numerical assessment is used as an objective, quantified assessment of the differences and similarities between objects ($O_n$, n=1-N).

The linkage found in step 1104 will preferably be found using a partial least squares (PLS) operation, such as a dual block (DB) PLS operation or a multi-block (MB) PLS operation. The objects ($O_n$) can be anatomical human parts such as finger prints, organs or tissues (e.g.; brain, breast), body fluids, facial features, etc. Alternatively, the objects ($O_n$) can be manmade, such as a manufactured electronic device. The measurements of these objects can be taken as indices, for example indices related to various aspects of performance or indices for measuring appearance.

Datasets ($D_i$) acquired in step 1102 can be an imaging modality or a non-imaging modality. Examples of an imaging modality include, but are not limited to, ultrasound, different PET and single photon emission tomography radiotracer methods, structural, functional, perfusion-weighted, or diffusion-weighted MRI, x-ray computed tomography, magnetic resonance spectroscopy measurements of N-acetyl aspartic acid, myoinositol, and other chemical compounds, electroencephalography, quantitative electroencephalography, event-related potentials, and other electrophysiological procedures, magnetoencephalography, and combinations of the foregoing imaging modality. Examples of a non-imaging modality include, but are not limited to, an electrophysiological measurement, a biochemical measurement, a molecular measurement, a transcriptomic measurement, a proteomic measurement, a cognitive measurement, a behavior measurement, and combinations of the foregoing.

Figure 12:
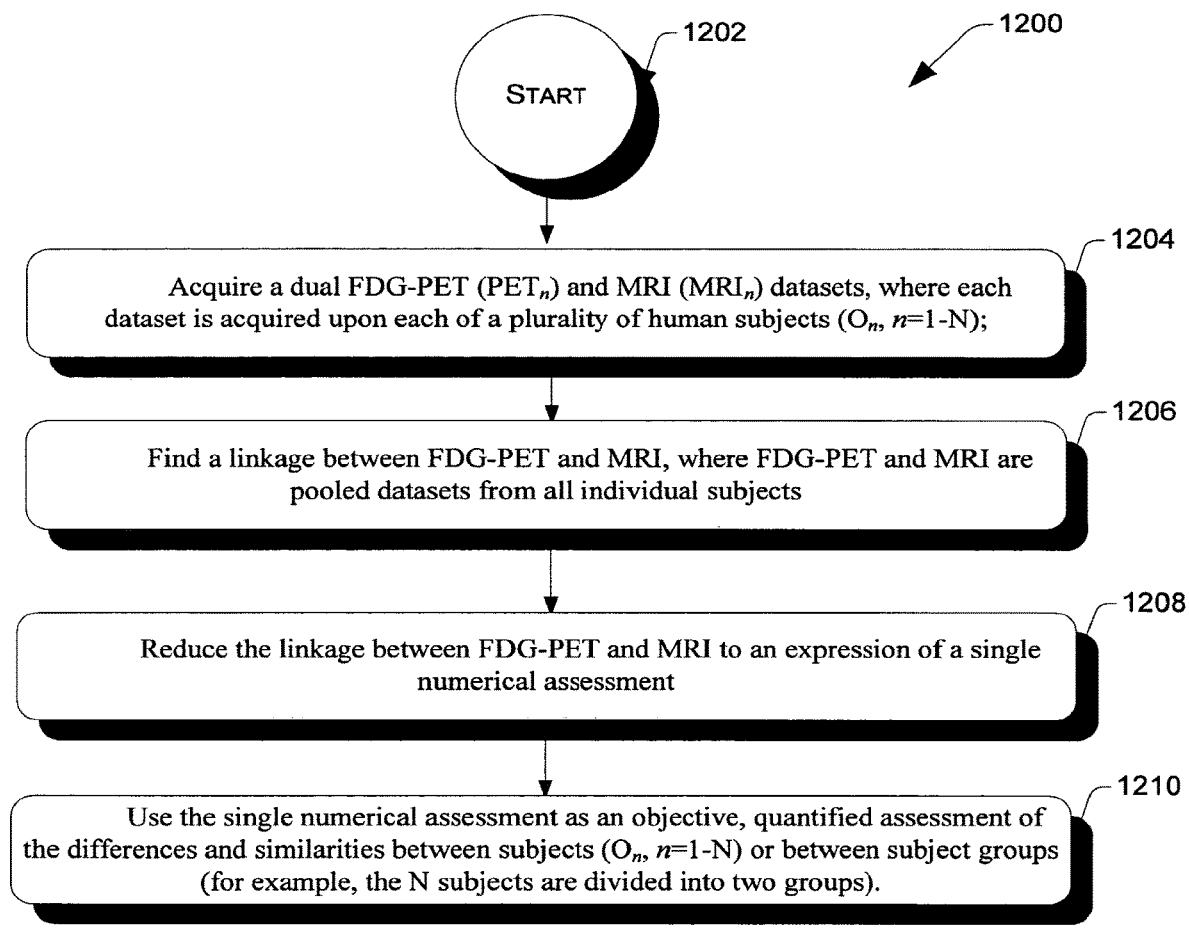

A more particular example of process 1100 is seen in FIG. 12 as process 1200. Process 1200 begins in step 1202 at which FDG-PET ($PET_n$) datasets and MRI ($MRI_n$) datasets are acquired, where each dataset is acquired upon each of a plurality of human subjects ($O_n$, n=1-N). In step 1204, a linkage is found between FDG-PET and MRI for their respective datasets $PET_n$ and $MRI_n$, where the FDG-PET datasets ($PET_n$) and the MRI datasets (MRI) are pooled into composite datasets from all of the individual human subjects. In step 1206, the linkage that was found in step 1204 between FDG-PET and MRI is reduced to an expression of a single numerical assessment. In step 1208, the single numerical assessment is used as an objective, quantified assessment of the differences and similarities between the human subjects ($O_n$, n=1-N) or between subject groups (for example, the N subjects are divided into two groups).

Figure 13:
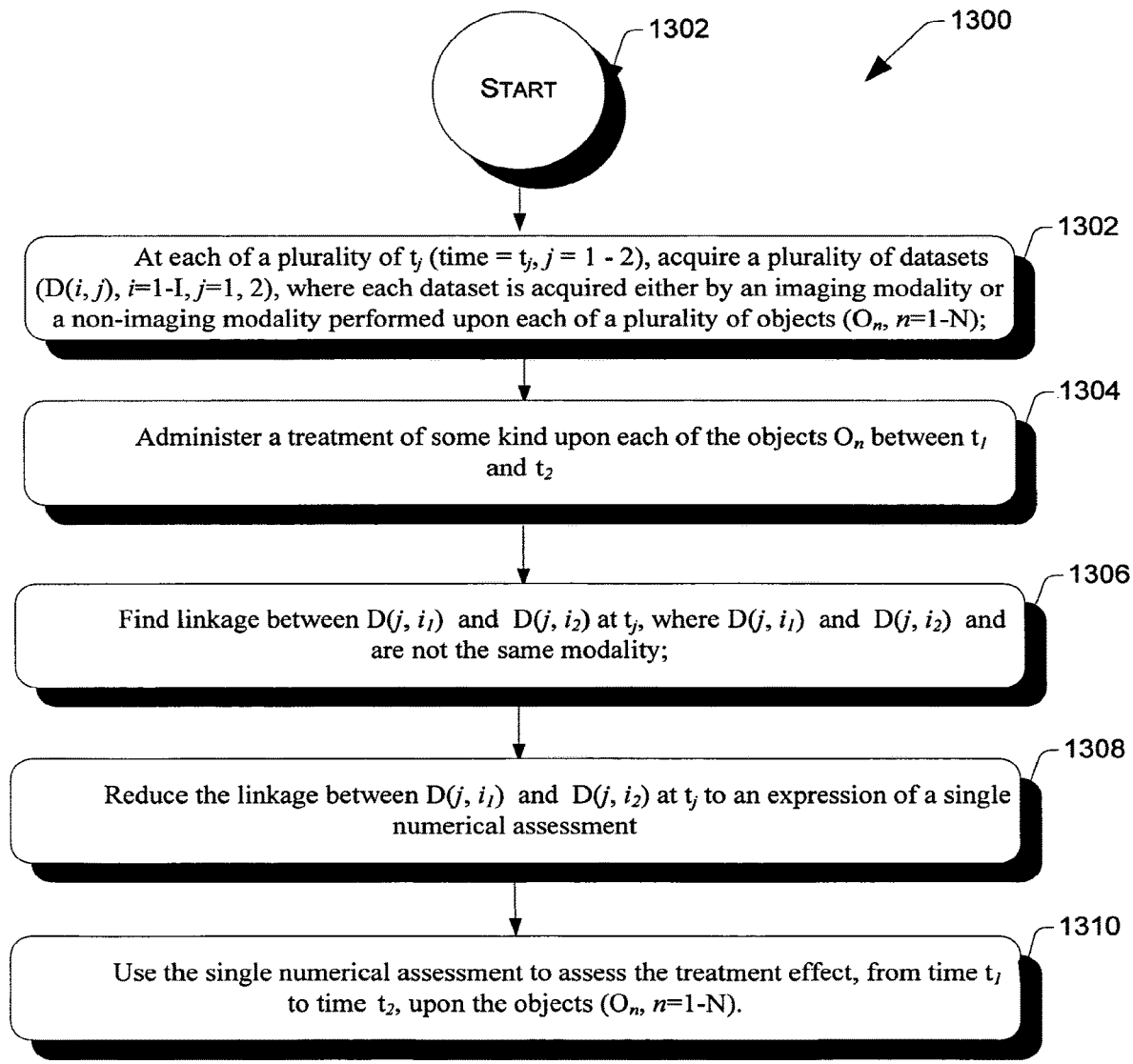

FIG. 13 is a flowchart of an exemplary implementation of a process 1300 in which a link is made between dataset to accomplish a useful result. In step 1302, at each of a plurality of $t_j$ (time=$t_j$, j=1-2), a plurality of datasets ($D_{i_1}^j$, i=1-I, j=1, 2) are acquired. Each dataset is acquired either by an imaging modality or a non-imaging modality performed upon each of a plurality of objects ($O_n$, n=1-N). In step 1304, a treatment of some kind is administered to each of the objects $O_n$ between time $t_1$ and time $t_2$. In step 1306, a linkage is found between $D_{i_1}^j$ and $D_{i_2}^j$ at time $t_j$, where $D_{i_1}^j$ and $D_{i_2}^j$ are not the same modality. In step 1308, the linkage between $D_{i_1}^j$ and $D_{i_2}^j$ at $t_j$ to is reduced to an expression of a single numerical assessment. In step 1310, the single numerical assessment is used as an objective, quantified assessment of the treatment effect, from time $t_1$ to time $t_2$, upon the objects ($O_n$, n=1-N).

Figure 14:
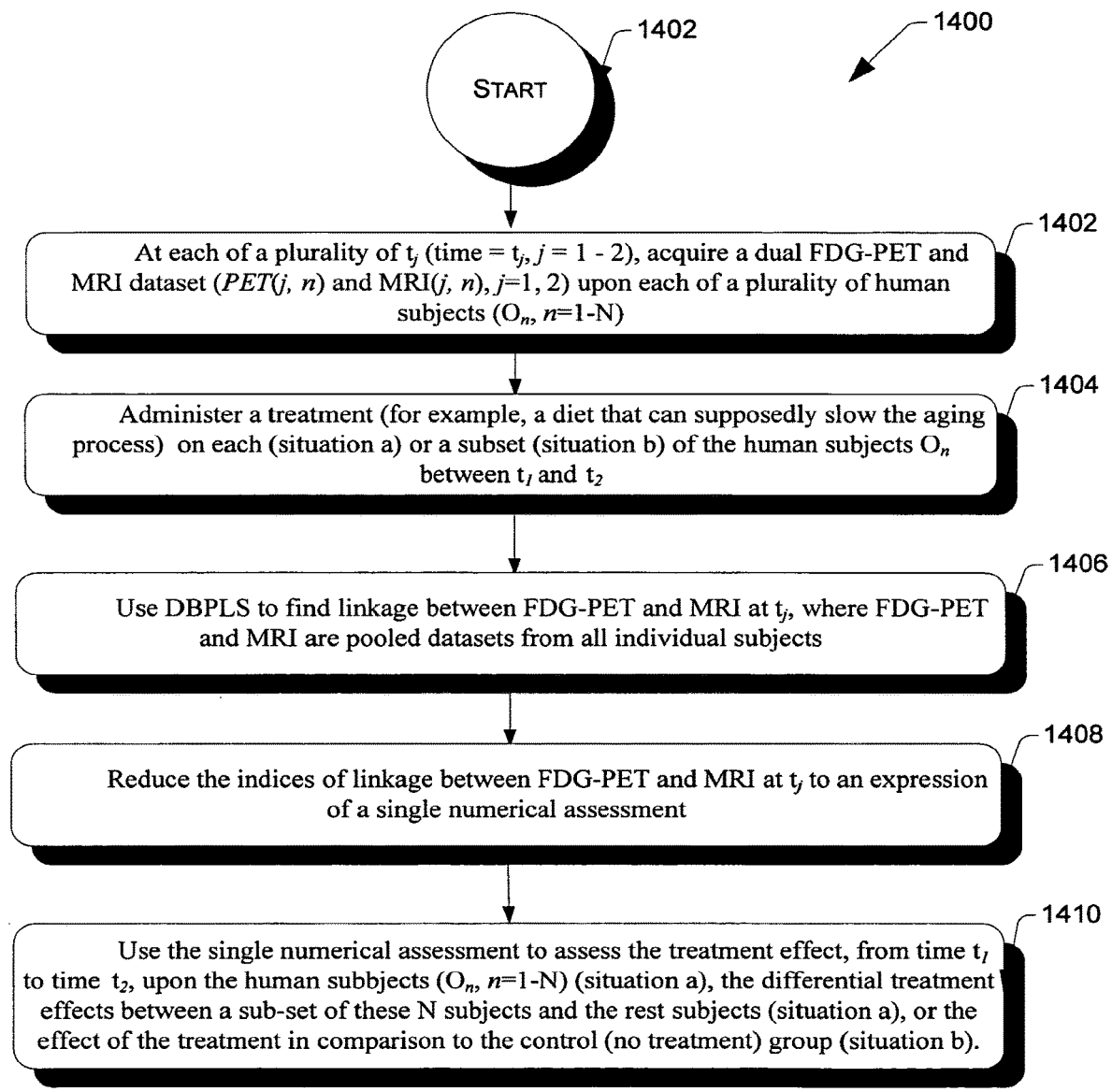

A more particular example of process 1300 is seen in FIG. 14 as process 1400. Process 1400 begins in step 1402 at which, for each of a plurality of $t_j$ (time=$t_j$, j=1-2), an acquisition is made of dual datasets (i) FDG-PET datasets ($PET_n^j$, j=1, 2), and (ii) MRI datasets ($MRI_n^j$, j=1, 2), where both datasets are acquired from a plurality of human subjects ($O_n$, n=1-N). In step 1404, there is an administration of a treatment (for example, a diet that is hypothesized as slowing the human aging process) on each of the human subjects $O_n$ between $t_1$ and $t_2$ (situation a), or on a subset of the human subjects $O_n$ (situation b) of the human subjects $O_n$ between $t_1$ and $t_2$. In step 1406, a linkage is found between FDG-PET and MRI for the dual respective datasets (i) FDG-PET datasets ($PET_n^j$, j=1, 2), and (ii) MRI datasets ($MRI_n^j$, j=1, 2), where the FDG-PET datasets ($PET_n^j$) and the MRI datasets ($MRI_n^j$) are pooled into composite datasets from all of the individual human subjects. In step 1408, indices of the linkage between FDG-PET and MRI at $t_j$ are reduced to a single numerical assessment. In step 1410, a use is made of the single numerical assessment to assess the treatment effect, from time $t_1$ to time $t_2$, upon the human subjects ($O_n$, n=1–N) (situation a), where the assessment represents a measurement of the differential treatment effects between a sub-set of the N human subjects and the rest of the human subjects (situation a), or the assessment represents a measurement of the effect of the treatment in comparison to a control group that received no treatment (situation b).

While preferred embodiments of this invention have been shown and described, modifications thereof can be made by one skilled in the art without departing from the spirit or teaching of this invention. The embodiments described herein are exemplary only and are not limiting. Many variations and modifications of the method and any apparatus are possible and are within the scope of the invention. One of ordinary skill in the art will recognize that the process just described may easily have steps added, taken away, or modified without departing from the principles of the present invention. Accordingly, the scope of protection is not limited to the embodiments described herein, but is only limited by the claims that follow, the scope of which shall include all equivalents of the subject matter of the claims.

APPENDIX

A: Iterative Power Algorithm Code, in Comparison to MATLAB svds.m

The MATLAB code for SVD calculation using power algorithm in comparison to MATLAB routine svds.m is given below. Note both the example power algorithm code and svds.m need the whole matrix to be in memory. In implementing power algorithm in our PLS analysis, all the matrix by vector, vector by scalar multiplications are done by reading in one sub-matrix a time.

MATLAB code for SVD Calculation Using Power:

```
m=1000; n=1000; %x and y dim of the matrix (you can change)
I=1; %only one singular value for demonstration purpose
A=randn(m,n); %randomly generated matrix to test
epsilon=1.0e-9; %convergence
numIte=5000; %number of iterations
%power algorithm below:
u=randn(m,1); v=randn(n,1); %initials for iteration
d=zeros(I);sigma=u'*A*v;
for k=1:numIte;
    z=u; u=A*v; u=u/norm(u,2); v=A'*z;
    v=v/norm(v,2); sigma=u'*A*v;
    error=norm(A*v-sigma*u,2);
        if sigma<0;u=-u;sigma=-sigma;end; %my own addition
    if rem(k,100)==0;
    disp(sprintf('%5d %9.7f %7.4f',k,error,sigma));
    end;
        if error<epsilon;break;end;
end
sigma=u'*A*v;norm(A*v-sigma*u,2);
norm(A'*u-sigma*v,2); %duplicate for fun :-)
[q,sig,r]=svds(A,2); %conventional SVD by matlab
%compare the power result with conventional SVD
if exist('h1')~=1;h1=figure; h2=figure;
set(h1,'unit','centimeters');set(h1,'pos',[2 12 15 10]);
set(h2,'unit','centimeters');set(h2,'pos',[18 12 15 10]);
set(h1, 'unit','pixels');set(h2,'unit','pixels');end;
figure(h1);
%linrfit(u,q(:,1));title('u against q'); %my own use
if (q(1,1)-q(100,1))/(u(1)-u(100))<0;
plot(u,-q(:,1),'o');title('u against q');
else;plot(u,q(:,1),'o');title('u against q');end;
figure(h2);
%linrfit(v,r(:,1));title('v against r'); %my own use
if (r(1,1)-r(100,1))/(v(1)-v(100))<0;
plot(v,-r(:,1),'o');title('v against r'); %45 degree line?
else;plot(v,r(:,1),'o');title('v against r');end;
disp(sprintf('%7.4f %7.4f',sigma,sig(1,1)));
```

B: Monte-Carlo Simulation Abstract

The abstract below was presented at the Nuclear Medicine annual meeting, June 2004. It reported our efforts in developing a Monte-Carlo simulation procedure to type-I error and statistical power calculation for some newly proposed indices for neuroimaging studies taking multiple comparison into consideration. This abstract described here is not specially designed for PLS, but can be easily adopted for PLS.

A Monte-Carlo Simulation Package For The Calculation Of Statistical Power, Familywise Type I Error Of Various Global Indices Associated With Neuroimaging Studies, by Kewei Chen, Ph.D, Eric M. Reiman, MD, Gene E. Alexander, Ph.D, Richard D. Gerkin, MD, MS, Daniel Bandy, MS, the Positron Emission Tomography Center, Banner Good Samaritan Medical Center, Phoenix, Ariz.; the Department of Mathematics and Statistics, Arizona State University; the Departments of Radiology and Psychiatry, University of Arizona; the Department of Psychology, Arizona State University; and the Arizona Alzheimer's Research Center and the Alzheimer's Disease Core Center, Phoenix, Ariz., USA.

Introduction:

To account for the familywise type I errors in neuroimaging studies, various approaches have been successfully applied. Revisiting the Monte-Carlo concept, we developed such a simulation package introducing various new global indices indicative of brain functional changes.

Methods:

Package description: The simulation is performed over MNI space taking various experimental designs into consideration. Characterizing the statistical parametric map as a whole, various new global indices were introduced that were related to conjunction of 'lack of deactivation' and map-wise histogram shape or symmetry etc. These indices can serve as an activation index relevant to the research hypothesis and whose type I error theoretical calculations (either exact or approximate) are yet to be realized. One example of the global indices is the ratio of the positive maxima to the (absolute) negative maxima of the t-scores over the brain volumes. Another is the kurtosis. In addition, the package can calculate the type I error of study-specific (unusual) observations such as the left/right symmetrical activation (not symmetry test), or activation occurring only within a sub-brain region (at least one voxel within this sub-region is above a height threshold u, and no voxel outside this region is higher than u1 (<<u)). This package is also helpful in examining the random field theorem (RFT) based p-value when needed (small sample size, low smoothness, etc.). Finally, this package can perform statistical power analysis taking the multiple comparisons into consideration. Example data: Oxygen-15 water PET data from 7 subjects in a study of right hand movement was used to illustrate the use of this computer package and the sensitivity of those global indices.

Results:

With the settings identical to the SPM analysis of the example PET data set, significant thresholds at p=0.05 as functions of the degree of freedoms (DF) were examined. It was found out, for example, the thresholds of the kurtosis of the map-wise histogram is a decrease function of DF, and behaves much like (3*DF-6)/(DF-4) plus a constant. To test the package ability for its power calculation, maximal effect size of 5, 10 and 15% respectively for two-sample t-test with 32 subjects in one group and 30 in another were introduced into the thalamus region with spatial variation. With multiple comparison corrected, the statistical powers were calculated to be 12, 68, and 98% respectively. For the example PET data set, it was found that the package performed equally well as or better than the RFT based approach. The hypothesized thalamus activation which did not survive the RFT corrected p=0.05 was detected by several of the proposed indices, post hoc.

Conclusion:

The global features and the simulation package provide an alternative to evaluate exact type-I errors/statistical powers for neuroimaging studies.

C: Preliminary Results of Alternative MBPLS

As stated in the Research Plan section, we assume there are m datasets, $X_1, X_2, \ldots, X_m$. $t_k$ is a latent variable representing $X_k$ (k=1, 2, \ldots, m), $t_k = \sum w_i^{(k)} x_i^{(k)}$ where $x_i^{(k)}$ is the ith column of matrix $X_k$ and $w_i^{(k)}$ is the corresponding weights (of unit norm). In this preliminary study, we tested the following object function for the calculation of the latent variables $\max(\min_{k<l}(\text{cov}(t_k, t_l)))$. MATLAB fmincon is used to optimize this object function for obtaining the MBPLS solution with the constrains that $\|t_k\|=1$. In this testing, we used m=5 with number of variables being [10 15 8 20 15] for datablock 1 to 2 separately. The number of measurements is 200. Multivariate Gaussian random numbers were generated for the five datasets as a whole with a zero vector as the mean and an arbitrary positive-definite matrix (diagonal elements all equal one) as the covariance matrix. Once the datasets are generated, the MBPLS procedure with the newly defined objected function was run 50 times each with different initial value (randomly generated).

We have the following conclusions from this preliminary numerical simulation procedure (See FIG. 1):

I, Existence:

there exist $t_k$'s that are with very strong linkage (defined as covariance) for all possible pairs as seen in FIG. 1. For example, the correlation coefficient between datablocks1 and 2 is 0.944 (the first subplot). In fact, the smallest absolute value among the pair-wise correlation coefficients is 0.929 (between datablocks 1 and 3). Furthermore, the existence was demonstrated by repeating the whole procedure many times with different number of datablocks and different number of variables in each datablock.

II, Conditional Uniqueness:

As it is, the object function given above does not guarantee a unique solution. This is evidenced that the optimization process converged to different solutions when different initial values were given. In fact, the partial uniqueness exists in that $m_1 t_k$'s are unique (regardless of the initial values) for $1<m_1<m$, and the rest $m-m_1 t_k$'s are not. To make the solution unique, additional constrains are posted for the $m-m_1$ datablocks. Let A be the index set for the datablock with unique $t_k$'s and $\Theta$ the one without. The optimization procedure is now to maximize:

$$\min_{k<l, k, l \in A \cup \Theta}(\text{abs}(\text{cov}(t_k, t_l))) + \min_{k \in \Theta} \text{var}(t_k).$$

Providing different initial values (randomly chosen) at each of many runs, we observed that the optimization procedure consistently converged to a unique solution.

Note, when m=2, the solution of this procedure is equivalent to the first latent pair of the ordinary DBPLS.

III. PLS Implementation Via Other Algorithms

The core complexity in the conventional PLS implementation lies in the computation of eigenvectors for the latent variables u and v of $\Omega$. To date, numerous eigen reduction methods have been developed, including Gauss-Jacobi iteration, QR reduction, Arnoldi iteration, Lanczos iteration, and Power algorithm, to name just a few. The Power iteration algorithm that we implanted was in a sub-matrix approach as the matrix size poses additional constrains. Every method has its own advantages and issues. In our analysis, we plan to explore the power and QR algorithms. In the power method a matrix whose eigenvalue needs to be computed is multiplied by a starting vector, till convergence is obtained which is close to the eigenvalue. The rate of convergence depends on the second larges eigenvalue. Since power iteration involves repeated matrix-vector products, which are easily implemented in parallel for dense or sparse matrix. While QR algorithm has been shown to be scalable for parallel computing machines, our objective would be to divide the matrix in to smaller units and compute at the node processor using the QR algorithm, review on the implementation is well documented [1,2,3]. In simplest form each iteration of QR method requires $O(n^3)$. It reduces to $O(n^2)$ if the matrix is in Hessenberg form, or $O(n)$ if symmetric matrix is in tri-diagonal form. Preliminary reduction is done by Householders or Givens transformation.

In addition to QR, we will also evaluate the use of the Rayleigh quotient. Assuming the X-Y covariance matrix is $C_{xy}$, the matrices, A and B, to define the Rayleigh quotient are, respectively, $$A = \begin{pmatrix} 0 & C_{xy} \\ C_{yx} & 0 \end{pmatrix} B = I,$$

where I is the identity matrix of the same size as matrix A. The Rayleigh quotient is defined as $$r(u) = \frac{u^T A u}{u^T B u}.$$

It is known [6] that the global maxima point, u, of the function r(u) corresponds to $$u = \begin{pmatrix} \mu_x w \\ \mu_y c \end{pmatrix}$$

where w and c are the DBPLS solution, or the first singular image pair (and $\mu_x$ and $\mu_y$ are scalars so that $\|u\|=\rho$, the covariance between t and u as defined in the DBPLS algorithm in the Background and Significance part). Operationally, there is no need to form matrix A, Cxy or Cyx in advance (which is extremely memory demanding). Instead and equivalently, we propose that the vectors u'X and Yu can be formal quickly at each iteration step.

NUMBERED REFERENCES

1. Abdi H (2003) Partial Least Squares (PLS) Regression. In: *Encyclopedia for research methods for the social sciences* (Lewis-Beck M et al., eds), Thousand Oaks (Calif.): Sage,
2. Alexander G et al. (2001) Regional reductions in gray matter density in cognitively normal apolipoprotein E e-4 homozygotes and heterozygotes using voxel-based MRI morphometry. 1st Annual meeting of Society for neuroscience, Nov. 10-15, 2001, San Diego.
3. Alexander G E, moeller J (1994) Application of the scaled subprofile model to functional imaging in neuropsychiatric disorders: A principal component approach to modeling brain function in disease. Human Brain Mapping 2:79-94
4. Alexander G E et al. (2002) Longitudinal PET Evaluation of Cerebral Metabolic Decline in Dementia: A Potential Outcome Measure in Alzheimer's Disease Treatment Studies. Am. J. Psychiatry 159:738-745
5. Alexander G, Moeller J (1994) Application of the Scaled Subprofile model: a statistical approach to the analysis of functional patterns in neuropsychiatric disorders: A principal component approach to modeling regional patterns of brain function in disease. Human Brain Mapping 79-94
6. Anderson N D et al. (2000) The effects of divided attention on encoding- and retrieval-related brain activity: A PET study of younger and older adults. J. Cogn Neurosci. 12:775-792
7. Arfanakis K et al. (2000) Combining independent component analysis and correlation analysis to probe interregional connectivity in fMRI task activation datasets. Magn Reson. Imaging 18:921-930
8. Beckmann C F, Smith S M (2004) Probabilistic independent component analysis for functional magnetic resonance imaging. IEEE Trans. Med. Imaging 23:137-152
9. Calhoun V D et al. (2001) Spatial and temporal independent component analysis of functional MRI data containing a pair of task-related waveforms. Hum. Brain Mapp. 13:43-53
10. Calhoun V D et al. (2003) Latency (in)sensitive ICA. Group independent component analysis of fMRI data in the temporal frequency domain. Neuroimage. 20:1661-1669
11. Chau W et al. (2004) Multi-modality imaging data analysis with partial least squares. Brain and Cognition 54:140-142
12. Chen H et al. (2002) [A method based on independent component analysis for processing fMRI data]. Sheng Wu Yi. Xue. Gong. Cheng Xue. Za Zhi. 19:64-66
13. Chen K et al. (2003) Linking Functional and Structural Brain Images with Multivariate Network Analyses: Description and Preliminary Application Using the Partial Least Square Method. World Congress on Medical Physics and Biomedical Engineering, Sydney, 2003
14. Chen K et al. (1998) Noninvasive quantification of the cerebral metabolic rate for glucose using positron emission tomography, 18F-fluoro-2-deoxyglucose, the Patlak method, and an image-derived input function. J. Cereb. Blood Flow Metab 18:716-723
15. Duann J R et al. (2002) Single-trial variability in event-related BOLD signals. Neuroimage. 15:823-835
16. Esbensen K et al. (2004) Fermentation monitoring using multisensor systems: feasibility study of the electronic tongue. Anal. Bioanal. Chem. 378:391-395
17. Esposito F et al. (2003) Real-time independent component analysis of fMRI time-series. Neuroimage. 20:2209-2224
18. Friston K J (1994) Functional and effective connectivity: A synthesis. Human Brain Mapping 2:56-78
19. Friston K J et al. (2003) Dynamic causal modeling. Neuroimage. 19:1273-1302
20. Gerlach R W, Kowalski B R (1979) Partial least squares path modeling with latent variables. Anal. Chim. Acta 112:417-421
21. Golub G, Van Loan C (1989) *Matrix Computations*, Baltimore, The Johns Hopkins University Press;
22. Habib R et al. (2003) Memory encoding and hippocampally-based novelty/familiarity discrimination networks. Neuropsychologia 41:271-279
23. Hammers A et al. (2002) Implementation and application of a brain template for multiple volumes of interest. Hum. Brain Mapp. 15:165-174
24. Horwitz B (1991) Functional Interactions in the Brain: Use of Correlations Between Regional Metabolic Rates. Journal of Cerebral Blood Flow and Metabolism 11: A114-A120
25. Horwitz B et al. (1995) Network analysis of PET-mapped visual pathways in Alzheimer type dementia. Neuroreport 6:2287-2292
26. Horwitz B et al. (1999) Neural modeling, functional brain imaging, and cognition. Trends Cogn Sci. 3:91-98
27. Höskuldsson A (2004) PLS Regression and the Covariance. Chemometrics http://www.acc.umu.se/~tnkjtg/Chemometrics/Editorial:
28. Hwang D et al. (2004) Inverse modeling using multi-block PLS to determine the environmental conditions that provide optimal cellular function. Bioinformatics. 20:487-499
29. Hyvarinen A et al. (2001) *Independent Component Analysis*, New York, John Wiley & Sons, Inc,
30. Ibanez V et al. (1998) Regional glucose metabolic abnormalities are not the results of atrophy in Alzheimer's disease. Neurology 50:1585-1593
31. Iidaka T et al. (2000) The effect of divided attention on encoding and retrieval in episodic memory revealed by positron emission tomography. J. Cogn Neurosci. 12:267-280
32. Keightley M L et al. (2003) An fMRI study investigating cognitive modulation of brain regions associated with emotional processing of visual stimuli. Neuropsychologia 41:585-596
33. Klunk W E et al. (2004) Imaging brain amyloid in Alzheimer's disease with Pittsburgh Compound-B. Ann. Neurol. 55:306-319

34. Lin F H et al. (2003) Multivariate analysis of neuronal interactions in the generalized partial least squares framework: simulations and empirical studies. Neuroimage. 20:625-642
35. Lobaugh N J et al. (2001) Spatiotemporal analysis of experimental differences in event-related potential data with partial least squares. Psychophysiology 38:517-530
36. Lopes J A et al. (2002) Multiblock PLS analysis of an industrial pharmaceutical process. Biotechnol. Bioeng. 80:419-427
37. McIntosh A R (1998) Understanding neural interactions in learning and memory using functional neuroimaging. Ann. N.Y. Acad. Sci. 855:556-571
38. McIntosh A R (1999) Mapping cognition to the brain through neural interactions. Memory. 7:523-548
39. McIntosh A R et al. (1996) Spatial pattern analysis of functional brain images using partial least squares. Neuroimage. 3:143-157
40. Mcintosh A R, Gonzalez-Lima F (1994) Structural equation moeling and its application to network anaylsis in functional brain imaging. Human Brain Mapping 2-22
41. McIntosh A R et al. (1999) Recruitment of unique neural systems to support visual memory in normal aging. Curr. Biol. 9:1275-1278
42. McKeown M J et al. (1998) Analysis of fMRI data by blind separation into independent spatial components. Hum. Brain Mapp. 6:160-188
43. Minoshima S et al. (1995) A diagnostic approach in Alzheimer's disease using three-dimensional stereotactic surface projections of fluorine-18-FDG PET. J. Nucl. Med. 36:1238-1248
44. Moritz C H et al. (2000) Whole-brain functional M R imaging activation from a finger-tapping task examined with independent component analysis. AJNR Am. J. Neuroradiol. 21:1629-1635
45. Nestor P G et al. (2002) A new statistical method for testing hypotheses of neuropsychological/MRI relationships in schizophrenia: partial least squares analysis. Schizophr. Res. 53:57-66
46. O'Donnell B F et al. (1999) Identification of neural circuits underlying P300 abnormalities in schizophrenia. Psychophysiology 36:388-398
47. Pietrini P et al. (1998) Abnormal metabolic patterns in Alzheimer's disease after correction for partial volume effects. Neurology 1585-1593
48. Rajah M N et al. (1999) Frontotemporal interactions in face encoding and recognition. Brain Res. Cogn Brain Res. 8:259-269
49. Reiman E M et al. (2001) Declining brain activity in cognitively normal apolipoprotein E epsilon 4 heterozygotes: A foundation for using positron emission tomography to efficiently test treatments to prevent Alzheimer's disease. Proc. Natl. Acad. Sci. U.S.A 98:3334-3339
50. Reiman E M et al. (1996) Preclinical evidence of Alzheimer's disease in persons homozygous for the epsilon 4 allele for apolipoprotein E. N. Engl. J. Med. 334:752-758
51. Reiman E M et al. (2004) Functional brain abnormalities in young adults at genetic risk for late-onset Alzheimer's dementia. Proc. Natl. Acad. Sci. U.S.A 101:284-289
52. Schmithorst V J, Holland S K (2004) Comparison of three methods for generating group statistical inferences from independent component analysis of functional magnetic resonance imaging data. J. Magn Reson. Imaging 19:365-368
53. Shoghi-Jadid K et al. (2002) Localization of neurofibrillary tangles and beta-amyloid plaques in the brains of living patients with Alzheimer disease. Am J Geriatr Psychiatry 10:24-35
54. Silverman D et al. (2001) Positron Emission Tomography in Evaluation of Dementia Regional Brain Metabolism and Long-term Outcome. JAMA 286:2120-2127
55. Westerhuis J A, Smilde A K (2001) Deflation in multiblock PLS. Journal of Chemometrics 15:485-493
56. Worsley K J et al. (1997) Characterizing the response of PET and fMRI data using multivariate linear models. Neuroimage. 6:305-319.

LETTERED REFERENCES

A. Alexander, G. and Moeller, J. 1994. Application of the Scaled Subprofile model: a statistical approach to the analysis of functional patterns in neuropsychiatric disorders: A principal component approach to modeling regional patterns of brain function in disease. Human Brain Mapping 79-94.
B. Anderson, N. D., Iidaka, T., Cabeza, R., Kapur, S., McIntosh, A. R., and Craik, F. I. 2000. The effects of divided attention on encoding- and retrieval-related brain activity: A PET study of younger and older adults. *J. Cogn Neurosci.* 12:775-792.
C. Ashburner, J. and Friston, K. 1997. Multimodal image coregistration and partitioning—a unified framework. *Neuroimage.* 6:209-217.
D. *Borga, M., Landelius, T., and Knutsson, H. 1997. A unified approach to PCA, PLS, MLR and CCA. *Report LiTH-ISY-R*-1992, *ISY, SE*-581 83
E. Calhoun, V. D., Adali, T., Pearlson, G. D., and Pekar, J. J. 2001. Spatial and temporal independent component analysis of functional MRI data containing a pair of task-related waveforms. *Hum. Brain Mapp.* 13:43-53.
F. Calhoun, V. D., Adali, T., Pekar, J. J., and Pearlson, G. D. 2003. Latency (in)sensitive ICA. Group independent component analysis of fMRI data in the temporal frequency domain. *Neuroimage.* 20:1661-1669.
G. Chen, H., Yao, D., Zhou, K., Zhou, T., Zhuo, Y., and Chen, L. 2002. [A method based on independent component analysis for processing fMRI data]. *Sheng Wu Yi. Xue. Gong. Cheng Xue. Za Zhi.* 19:64-66.
H. Chen, K., Bandy, D., Reiman, E., Huang, S. C., Lawson, M., Feng, D., Yun, L. S., and Palant, A. 1998. Noninvasive quantification of the cerebral metabolic rate for glucose using positron emission tomography, 18F-fluoro-2-deoxyglucose, the Patlak method, and an image-derived input function. *J. Cereb. Blood Flow Metab* 18:716-723.
I. DeCarli, C., Murphy, D. G., Gillette, J. A., Haxby, J. V., Teichberg, D., Schapiro, M. B., and Horwitz, B. 1994. Lack of age-related differences in temporal lobe volume of very healthy adults. *AJNR Am. J. Neuroradiol.* 15:689-696.
J. Esposito, F., Seifritz, E., Formisano, E., Morrone, R., Scarabino, T., Tedeschi, G., Cirillo, S., Goebel, R., and Di Salle, F. 2003. Real-time independent component analysis of fMRI time-series. *Neuroimage.* 20:2209-2224.
K. Friston, K. J. 1994. Functional and effective connectivity: A synthesis. *Human Brain Mapping* 2:56-78.
L. Friston, K. J., Harrison, L., and Penny, W. 2003. Dynamic causal modelling. *Neuroimage.* 19:1273-1302.
M. Golomb, J., Kluger, A., de Leon, M. J., Ferris, S. H., Convit, A., Mittelman, M. S., Cohen, J., Rusinek, H., De, S. S., and George, A. E. 1994. Hippocampal formation size in normal human aging: a correlate of delayed secondary memory performance. *Learn. Mem.* 1:45-54.

N. Golub, G H and Van Loan, C F. 1989. *Matrix Computations.* The Johns Hopkins University Press; Baltimore O. Good, C. D., Johnsrude, I. S., Ashburner, J., Henson, R. N., Friston, K. J., and Frackowiak, R. S. 2001. A voxel-based morphometric study of ageing in 465 normal adult human brains. *Neuroimage.* 14:21-36.

P. Habib, R., McIntosh, A. R., Wheeler, M. A., and Tulving, E. 2003. Memory encoding and hippocampally-based novelty/familiarity discrimination networks. *Neuropsychologia* 41:271-279.

Q. Hoegaerts, L., Suykens, J. A. K., Vandewalle, J., and De Moor, B. 2003. Kernel PLS variants for regression. *Proc. of the 11th European Symposium on Artificial Neural Networks* 203-208.

R. Horwitz, B. 1991. Functional Interactions in the Brain: Use of Correlations Between Regional Metabolic Rates. *Journal of Cerebral Blood Flow and Metabolism* 11:A114-A120.

S. Horwitz, B., McIntosh, A. R., Haxby, J. V., Furey, M., Salerno, J. A., Schapiro, M. B., Rapoport, S. I., and Grady, C. L. 1995. Network analysis of PET-mapped visual pathways in Alzheimer type dementia. *Neuroreport* 6:2287-2292.

T. Horwitz, B., Tagamets, M. A., and McIntosh, A. R. 1999. Neural modeling, functional brain imaging, and cognition. *Trends Cogn Sci.* 3:91-98.

U. Iidaka, T., Anderson, N. D., Kapur, S., Cabeza, R., and Craik, F. I. 2000. The effect of divided attention on encoding and retrieval in episodic memory revealed by positron emission tomography. *J. Cogn Neurosci.* 12:267-280.

V. Jernigan, T. L., Archibald, S. L., Berhow, M. T., Sowell, E. R., Foster, D. S., and Hesselink, J. R. 1991. Cerebral structure on MRI, Part I: Localization of age-related changes. *Biol. Psychiatry* 29:55-67.

W. Keightley, M. L., Winocur, G., Graham, S. J., Mayberg, H. S., Hevenor, S. J., and Grady, C. L. 2003. An fMRI study investigating cognitive modulation of brain regions associated with emotional processing of visual stimuli. *Neuropsychologia* 41:585-596.

X. Kiebel, S. J., Ashburner, J., Poline, J. B., and Friston, K. J. 1997. MRI and PET coregistration—a cross validation of statistical parametric mapping and automated image registration. *Neuroimage.* 5:271-279.

Y. Klunk, W. E., Engler, H., Nordberg, A., Wang, Y., Blomqvist, G., Holt, D. P., Bergstrom, M., Savitcheva, I., Huang, G. F., Estrada, S., Ausen, B., Debnath, M. L., Barletta, J., Price, J. C., Sandell, J., Lopresti, B. J., Wall, A., Koivisto, P., Antoni, G., Mathis, C. A., and Langstrom, B. 2004. Imaging brain amyloid in Alzheimer's disease with Pittsburgh Compound-B. *Annals of Neurology* 55:306-319.

Z. Lin, F. H., McIntosh, A. R., Agnew, J. A., Eden, G. F., Zeffiro, T. A., and Belliveau, J. W. 2003. Multivariate analysis of neuronal interactions in the generalized partial least squares framework: simulations and empirical studies. *Neuroimage.* 20:625-642.

AA. Lobaugh, N. J., West, R., and McIntosh, A. R. 2001. Spatiotemporal analysis of experimental differences in event-related potential data with partial least squares. *Psychophysiology* 38:517-530.

BB. Loessner, A., Alavi, A., Lewandrowski, K. U., Mozley, D., Souder, E., and Gur, R. E. 1995. Regional cerebral function determined by FDG-PET in healthy volunteers: normal patterns and changes with age. *J. Nucl. Med.* 36:1141-1149.

CC. Lopes, J. A., Menezes, J. C., Westerhuis, J. A., and Smilde, A. K. 2002. Multiblock PLS analysis of an industrial pharmaceutical process. *Biotechnol. Bioeng.* 80:419-427.

DD. McIntosh, A. R. 1999. Mapping cognition to the brain through neural interactions. *Memory.* 7:523-548.

EE. McIntosh, A. R. 1998. Understanding neural interactions in learning and memory using functional neuroimaging. Annals of the New York Academy of Sciences 855:556-571.

FF. McIntosh, A. R., Bookstein, F. L., Haxby, J. V., and Grady, C. L. 1996. Spatial pattern analysis of functional brain images using partial least squares. *Neuroimage.* 3:143-157.

GG. Mcintosh, A. R. and Gonzalez-Lima, F. 1994. Structural equation moeling and its application to network anaylsis in functional brain imaging. *Human Brain Mapping* 2-22.

HH. McIntosh, A. R., Sekuler, A. B., Penpeci, C., Rajah, M. N., Grady, C. L., Sekuler, R., and Bennett, P. J. 1999. Recruitment of unique neural systems to support visual memory in normal aging. *Curr. Biol.* 9:1275-1278.

II. McKeown, M. J., Makeig, S., Brown, G. G., Jung, T. P., Kindermann, S. S., Bell, A. J., and Sejnowski, T. J. 1998. Analysis of fMRI data by blind separation into independent spatial components. *Hum. Brain Mapp.* 6:160-188.

JJ. Meltzer, C. C., Cantwell, M. N., Greer, P. J., Ben-Eliezer, D., Smith, G., Frank, G., Kaye, W. H., Houck, P. R., and Price, J. C. 2000. Does cerebral blood flow decline in healthy aging? A PET study with partial-volume correction. *J. Nucl. Med.* 41:1842-1848.

KK. Moeller, J. R., Strother, S. C., Sidtis, J. J., and Rottenberg, D. A. 1987. Scaled subprofile model: a statistical approach to the analysis of functional patterns in positron emission tomographic data. *J. Cereb. Blood Flow Metab* 7:649-658.

LL. Moritz, C. H., Haughton, V. M., Cordes, D., Quigley, M., and Meyerand, M. E. 2000. Whole-brain functional M R imaging activation from a finger-tapping task examined with independent component analysis. *AJNR Am. J. Neuroradiol.* 21:1629-1635.

MM. Murphy, D. G., DeCarli, C., Schapiro, M. B., Rapoport, S. I., and Horwitz, B. 1992. Age-related differences in volumes of subcortical nuclei, brain matter, and cerebrospinal fluid in healthy men as measured with magnetic resonance imaging. *Arch. Neurol.* 49:839-845.

NN. Nestor, P. G., O'Donnell, B. F., McCarley, R. W., Niznikiewicz, M., Barnard, J., Jen, S. Z., Bookstein, F. L., and Shenton, M. E. 2002. A new statistical method for testing hypotheses of neuropsychological/MRI relationships in schizophrenia: partial least squares analysis. *Schizophr. Res.* 53:57-66.

OO. O'Donnell, B. F., McCarley, R. W., Potts, G. F., Salisbury, D. F., Nestor, P. G., Hirayasu, Y., Niznikiewicz, M. A., Barnard, J., Shen, Z. J., Weinstein, D. M., Bookstein, F. L., and Shenton, M. E. 1999. Identification of neural circuits underlying P300 abnormalities in schizophrenia. *Psychophysiology* 36:388-398.

PP. Pietrini, P., Alexander G E, and et al 1998. Abnormal metabolic patterns in Alzheimer's disease after correction for partial volume effects. *Neurology* 1585-1593.

QQ. Press, W H, Vetterling, W T, Teukolsky, S A, and Flannery, B P. 1992. *Numerical Recipes in C The Art of Scientific computing.* Press Syndicate of the University of Cambridge, N.Y.

RR. Rajah, M. N. and McIntosh, A. R. 2005. Overlap in the functional neural systems involved in semantic and episodic memory retrieval. *J. Cogn Neurosci.* 17:470-482.

SS. Rajah, M. N., McIntosh, A. R., and Grady, C. L. 1999. Frontotemporal interactions in face encoding and recognition. *Brain Res. Cogn Brain Res.* 8:259-269.

TT. Reiman, E. M., Caselli, R. J., Chen, K., Alexander, G. E., Bandy, D., and Frost, J. 2001. Declining brain activity in cognitively normal apolipoprotein E epsilon 4 heterozygotes: A foundation for using positron emission tomography to efficiently test treatments to prevent Alzheimer's disease. *Proc. Natl. Acad. Sci. U.S.A* 98:3334-3339.

UU. Reiman, E. M., Caselli, R. J., Yun, L. S., Chen, K., Bandy, D., Minoshima, S., Thibodeau, S. N., and Osborne, D. 1996. Preclinical evidence of Alzheimer's disease in persons homozygous for the epsilon 4 allele for apolipoprotein E. *New England Journal of Medicine* 334:752-758.

VV. Reiman, E. M., Chen, K., Alexander, G. E., Caselli, R. J., Bandy, D., Osborne, D., Saunders, A. M., and Hardy, J. 2004. Functional brain abnormalities in young adults at genetic risk for late-onset Alzheimer's dementia. *Proc. Natl. Acad. Sci. U.S.A* 101:284-289.

WW. Salmon, E., Maquet, P., Sadzot, B., Degueldre, C., Lemaire, C., and Franck, G. 1991. Decrease of frontal metabolism demonstrated by positron emission tomography in a population of healthy elderly volunteers. *Acta Neurol. Belg.* 91:288-295.

XX. Schmithorst, V. J. and Holland, S. K. 2004. Comparison of three methods for generating group statistical inferences from independent component analysis of functional magnetic resonance imaging data. *J. Magn Reson. Imaging* 19:365-368.

YY. Shoghi-Jadid, K., Small, G. W., Agdeppa, E. D., Kepe, V., Ercoli, L. M., Siddarth, P., Read, S., Satyamurthy, N., Petric, A., Huang, S. C., and Barrio, J. R. 2002. Localization of neurofibrillary tangles and beta-amyloid plaques in the brains of living patients with Alzheimer disease. *Am J Geriatr Psychiatry* 10:24-35.

ZZ. Westerhuis, J. A., Coenegracht, P. M. J., and Lerk, C. F. 1997. Multivariate modelling of the tablet manufacturing process with wet granulation for tablet optimization and in-process control. *Int. J. Pharmaceut.* 156:109-117.

AAA. Westerhuis, J. A., de Haan, P., Zwinkels, J., Jansen, W. T., Coenegracht, P. M. J., and Lerk, C. F. 1996. Optimisation of the composition and production of mannitol/microcrystalline cellulose tablets. *Int. J. Pharmaceut.* 143:151-162.

BBB. Westerhuis, J. A. and Smilde, A. K. 2001. Deflation in multiblock PLS. *Journal of Chemometrics* 15:485-493.

CCC. Worsley, K. J., Poline, J. B., Friston, K. J., and Evans, A. C. 1997. Characterizing the response of PET and fMRI data using multivariate linear models. *Neuroimage.* 6:305-319.

What is claimed is:

1. A computer-implemented method for assessing multimodality datasets in the evaluation of a treatment for a disease, the method comprising:

receiving at a first computing device a plurality of longitudinal datasets regarding each of a plurality of subjects, wherein a first longitudinal dataset $D_i$ of the plurality of longitudinal datasets is a dataset of an imaging modality captured by an imaging system and received from the imaging system over a communications network, and a second longitudinal dataset $D_j$ of the plurality of longitudinal datasets is a dataset of a non-imaging modality received from a second computing device over the network, the $D_i$ and $D_j$ datasets being independent datasets and forming respective square matrices; and executing instructions stored in memory of the first computing device, wherein execution of the instructions by a processor of the first computing device:

partitions each of the $D_i$ and $D_j$ datasets into a plurality of submatrices, computes a linkage between the $D_i$ and $D_j$ datasets, wherein computing the linkage includes reading the $D_i$ and $D_j$ submatrices into memory one by one and processing the read submatrices one by one as needed to iteratively compute a single numerical assessment, wherein the single numerical assessment represents a differential effect of a treatment for a disease between at least two subsets of the plurality of subjects, and reports the single numerical assessment to a user of the first computing device at a display interface of the first computing device.

2. The computer-implemented method of claim 1, wherein the imaging modality is selected from the group consisting of: ultrasound; positron emission tomography, single photon emission tomography radiotracer, or other nuclear medicine procedure; structural, functional, perfusion-weighted, or diffusion-weighted magnetic resonance imaging; x-ray computed tomography; magnetic resonance spectroscopy measurements of N-acetyl aspartic acid, myoinositol, or other chemical compounds; electroencephalography, quantitative electroencephalography, event-related potentials, or other electrophysiological procedures; magnetoencephalography; a medical imaging measurement procedure; and a non-medical imaging measurement procedure.

3. The computer-implemented method of claim 1, wherein the non-imaging modality is selected from the group consisting of: a set of biochemical measurements; a set of molecular measurements; a set of genetic measurements; a set of transcriptomic measurements; a set of proteomic measurements; a set of cognitive measurements or clinical ratings; a set of behavioral measurements; and a set of measurements from a non-medical non-imaging modality.

4. The computer-implemented method of claim 1, further comprising defining at least one of the $D_i$ and $D_j$ datasets based on a time interval.

5. The computer-implemented method of claim 1, wherein the method further comprises administering a treatment for the disease to a set of the subjects over a period of time.

6. The computer-implemented method of claim 1, further comprising generating, based on the single numerical assessment, a report on a severity level of a progression of the disease.

7. The computer-implemented method of claim 1, wherein computing the linkage between the $D_i$ and $D_j$ datasets comprises using a partial least squares analysis.

8. A computer-implemented method for assessing multimodality datasets in the evaluation of a treatment for a disease, the method comprising:

receiving at a computing device a plurality of longitudinal datasets regarding each of a plurality of subjects, wherein a first longitudinal dataset $D_i$ of the plurality of longitudinal datasets is a dataset of a first imaging modality captured by one or more imaging systems and received from the one or more imaging systems over a communications network, and a second longitudinal dataset $D_j$ of the plurality of longitudinal datasets is a dataset of a second imaging modality received from the one or more imaging systems over the network, the $D_i$ and $D_j$ datasets being independent datasets and forming respective square matrices; and executing instructions stored in memory of the computing device, wherein execution of the instructions by a processor of the computing device:

partitions each of the $D_i$ and $D_j$ datasets into a plurality of submatrices, computes a linkage between the $D_i$ and $D_j$ datasets, wherein computing the linkage includes reading the $D_i$ and $D_j$ submatrices into memory one by one and processing the read submatrices one by one as needed to iteratively compute a single numerical assessment, wherein the single numerical assessment represents a differential effect of a treatment for a disease between at least two subsets of the plurality of subjects, and reports the single numerical assessment to a user of the computing device at a display interface of the computing device.

9. The computer-implemented method of claim 8, wherein the first imaging modality is selected from the group consisting of: ultrasound; positron emission tomography, single photon emission tomography radiotracer, or other nuclear medicine procedure; structural, functional, perfusion-weighted, or diffusion-weighted magnetic resonance imaging; x-ray computed tomography; magnetic resonance spectroscopy measurements of N-acetyl aspartic acid, myoinositol, or other chemical compounds; electroencephalography, quantitative electroencephalography, event-related potentials, or other electrophysiological procedures; magnetoencephalography; a medical imaging measurement procedure; and a non-medical imaging measurement procedure.

10. The computer-implemented method of claim 8, wherein the second imaging modality is selected from the group consisting of: ultrasound; positron emission tomography, single photon emission tomography radiotracer, or other nuclear medicine procedure; structural, functional, perfusion-weighted, or diffusion-weighted magnetic resonance imaging; x-ray computed tomography; magnetic resonance spectroscopy measurements of N-acetyl aspartic acid, myoinositol, or other chemical compounds; electroencephalography, quantitative electroencephalography, event-related potentials, or other electrophysiological procedures; magnetoencephalography; a medical imaging measurement procedure; and a non-medical imaging measurement procedure.

11. The computer-implemented method of claim 8, wherein the method further comprises administering a treatment for the disease to a set of the subjects over a period of time.

12. The computer-implemented method of claim 8, further comprising generating, based on the single numerical assessment, a report on a severity level of a progression of the disease.

13. The computer-implemented method of claim 8, wherein computing the linkage between the $D_i$ and $D_j$ datasets comprises using a partial least squares analysis.

14. A computer-implemented method for assessing a linkage between multi-modality datasets, the method comprising:

receiving at a first computing device a plurality of longitudinal datasets regarding each of a plurality of subjects, wherein a first longitudinal dataset $D_i$ of the plurality of longitudinal datasets is a dataset of an imaging modality captured by an imaging system and received from the imaging system over a communications network, and a second longitudinal dataset $D_j$ of the plurality of longitudinal datasets is a dataset of a non-imaging modality received from a second computing device over the network, the $D_i$ and $D_j$ datasets being independent datasets and forming respective square matrices; and executing instructions stored in memory of the first computing device, wherein execution of the instructions by a processor of the first computing device:

partitions each of the $D_i$ and $D_j$ datasets into a plurality of submatrices, computes a linkage between the $D_i$ and $D_j$ datasets, wherein computing the linkage includes reading the $D_i$ and $D_j$ submatrices into memory one by one and processing the read submatrices one by one as needed to iteratively compute a single numerical assessment, wherein the single numerical assessment represents a differential effect of a presence of a specified characteristic between at least two subsets of the plurality of subjects, and reports the single numerical assessment to a user of the first computing device at a display interface of the first computing device.

15. The computer-implemented method of claim 14, wherein the characteristic is one or more of age, a weight measurement, a triglyceride measurement, or a body fat measurement.

16. The computer-implemented method of claim 14, wherein the characteristic is the possession of a specified gene.

17. The computer-implemented method of claim 16, wherein the gene is an apolipoprotein (APOE) gene.

18. The computer-implemented method of claim 14, wherein the characteristic is the possession of at least one ε4 allele of the APOE gene.

19. The computer-implemented method of claim 14, wherein the characteristic is the possession of two ε4 alleles of the APOE gene.

20. The computer-implemented method of claim 14, wherein computing the linkage between the $D_i$ and $D_j$ datasets comprises using a partial least squares analysis.

* * * * *